United States Patent
Klysner

(10) Patent No.: US 7,285,273 B1
(45) Date of Patent: *Oct. 23, 2007

(54) METHOD FOR DOWN-REGULATING IL5 ACTIVITY

(75) Inventor: Steen Klysner, Horsholm (DK)

(73) Assignee: Pharmexa A/S, Horsholm (DK)

(*) Notice: Subject to any disclaimer, the term of this patent is extended or adjusted under 35 U.S.C. 154(b) by 0 days.

This patent is subject to a terminal disclaimer.

(21) Appl. No.: 09/980,916

(22) PCT Filed: Apr. 19, 2000

(86) PCT No.: PCT/DK00/00205

§ 371 (c)(1),
(2), (4) Date: Feb. 19, 2002

(87) PCT Pub. No.: WO00/65058

PCT Pub. Date: Nov. 2, 2000

Related U.S. Application Data

(60) Provisional application No. 60/132,811, filed on May 6, 1999.

(30) Foreign Application Priority Data

Apr. 23, 1999 (DK) .............................. 1999 00552

(51) Int. Cl.
- A61K 39/00 (2006.01)
- A61K 45/00 (2006.01)
- C12P 21/04 (2006.01)
- C07K 1/00 (2006.01)

(52) U.S. Cl. ............... 424/185.1; 424/85.2; 435/39.52; 435/69.7; 530/351

(58) Field of Classification Search ............ 514/2
See application file for complete search history.

(56) References Cited

U.S. PATENT DOCUMENTS

| | | | |
|---|---|---|---|
| 5,096,704 A | 3/1992 | Coffman et al. | |
| 5,616,488 A | 4/1997 | Sullivan et al. | |
| 6,093,405 A | 7/2000 | Zagury et al. | |
| 2004/0141958 A1* | 7/2004 | Steinaa et al. | 424/93.21 |

FOREIGN PATENT DOCUMENTS

| WO | WO93/23076 A1 | 11/1993 |
|---|---|---|
| WO | WO95/05849 | 3/1995 |
| WO | WO95/05849 A | 3/1995 |
| WO | WO 95/07707 | 3/1995 |
| WO | WO95/07707 | 3/1995 |
| WO | WO95/26365 | 10/1995 |
| WO | WO95/26365 A | 10/1995 |
| WO | WO95/31480 | 11/1995 |
| WO | WO95/31480 A | 11/1995 |
| WO | WO95/35375 A1 | 12/1995 |
| WO | WO97/00321 A | 1/1997 |
| WO | WO97/00321 | 3/1997 |
| WO | WO 97/00321 | * 3/1997 |
| WO | WO97/45448 | 12/1997 |
| WO | WO97/45448 A | 12/1997 |
| WO | WO98/17799 | 4/1998 |
| WO | WO98/17799 A | 4/1998 |
| WO | WO98/23635 | 6/1998 |
| WO | WO 98/23635 | 6/1998 |
| WO | WO 98/31398 | 7/1998 |
| WO | WO98/31398 | 7/1998 |
| WO | WO98/47923 | 10/1998 |
| WO | WO98/47923 A | 10/1998 |

OTHER PUBLICATIONS

Mann et. al., Medical Hypotheses, In Press, Corrected Proof, Available online Oct. 14, 2004.*
Riley et al., Pharmacogenomics 2000, vol. 1(1): pp. 39-47.*
Luck et al., Molecular Endocrinology 1991, vol. 5(12): pp. 1880-1886, esp. p. 1881, table 1.*
Dalum et al., Mol Immunol. 1997, vol. 34(16-17): pp. 1113-1120.*
Elenkov et al., Ann N Y Acad Sci. 2002, vol. 966: pp. 290-303, esp. p. 291: paragraph 2.*
Sher. A., et al. 1990. Proc. Natl. Acad. Sci. USA. vol. 87, pp. 61-65.*
Mori, A., et al. 1997. J. Allergy Clin. Immunol. vol. 100(6 Pt. 2), pp. S56-S64.*
Lee, N.A., et al. 1997. J. Immunol. vol. 158, pp. 1332-1344.*
Lee N.A. et al. Expression of IL-5 in thymocytes/T cells leads to the development of a massive eosinophilia, extramedullary eosinophilopoiesis, and uniquie histopathologies. 1997. J. Immunol. vol. 158, p. 1332-1344.*
K. Takatsu, "Interleukin 5 and B cell differentiation," Cytokine and Growth Factor Reviews, vol. 9, No. 1, pp. 25-35 (Mar. 1998).
J. Weltman et al., "Interleukin-5: a proeosinophil cytokine mediator of imflammation in asthma and a target for antisense therapy", Allergy and Asthma Proceedings, vol. 19, No. 5, pp. 257-261 (Sep. 1998).
D. Broide et al., "Intradermal gene vaccination down-regulates both arms of the allergic response", Journal of Allergy and Clinical Immunology, vol. 99, No. 1, part 2, p. S129 (Jan. 1997).
The Journal of Immunology 160((1998) 3363-73 Southwood et al "Several common."
Scand J Immunol 47(1998) 596-602 Ohashi et al "Allergen-induced synthesis . . . ".
J Exp Med 185(12) (Jun. 16, 1997) 2143-56 Lee et al "Interleukin-5 . . . ".
The Journal of Immunology 158(1997) 1332-44 Lee et al "Expression of IL-5 . . . ".

(Continued)

Primary Examiner—Robert S. Landsman
Assistant Examiner—Bruce D. Hissong
(74) Attorney, Agent, or Firm—Birch, Stewart, Kolasch & Birch, LLP

(57) ABSTRACT

Improvements in therapy and prevention of conditions characterized by an elevated level of eosinophil leukocytes, i.e. conditions such as asthma and other chronic allergic diseases are disclosed. A method is provided for down-regulating interleukin 5 (IL5) by enabling the production of antibodies against IL5 thereby reducing the level of activity of eosinophils.

17 Claims, 7 Drawing Sheets

OTHER PUBLICATIONS

Figure 2A:
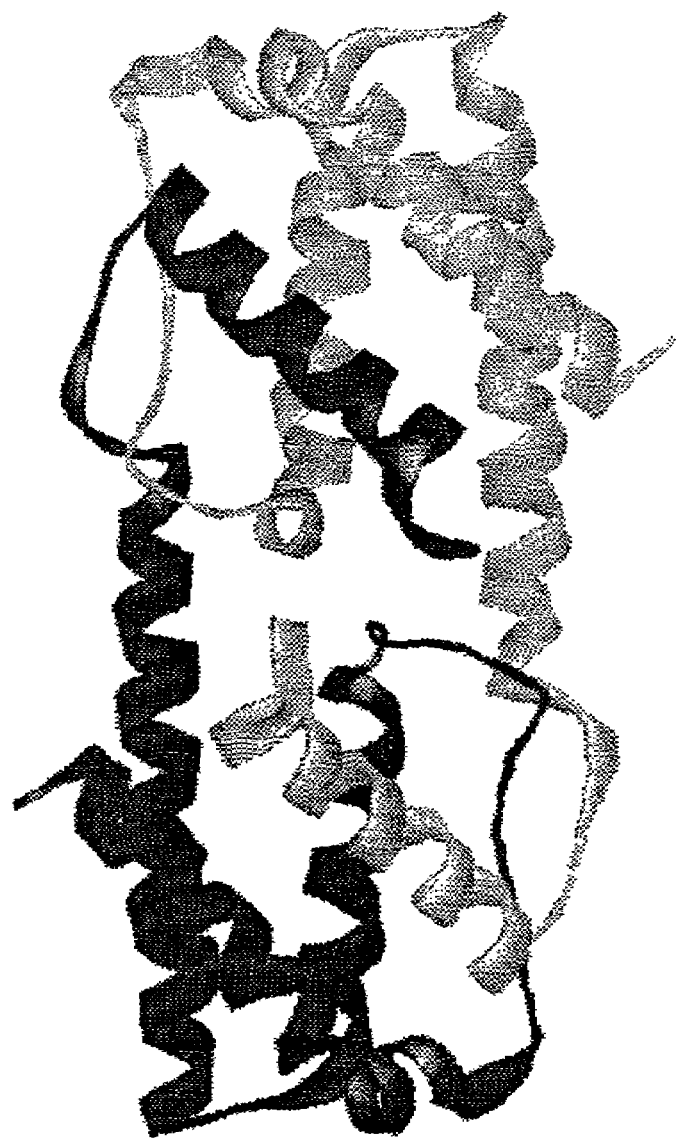
Figure 2B:
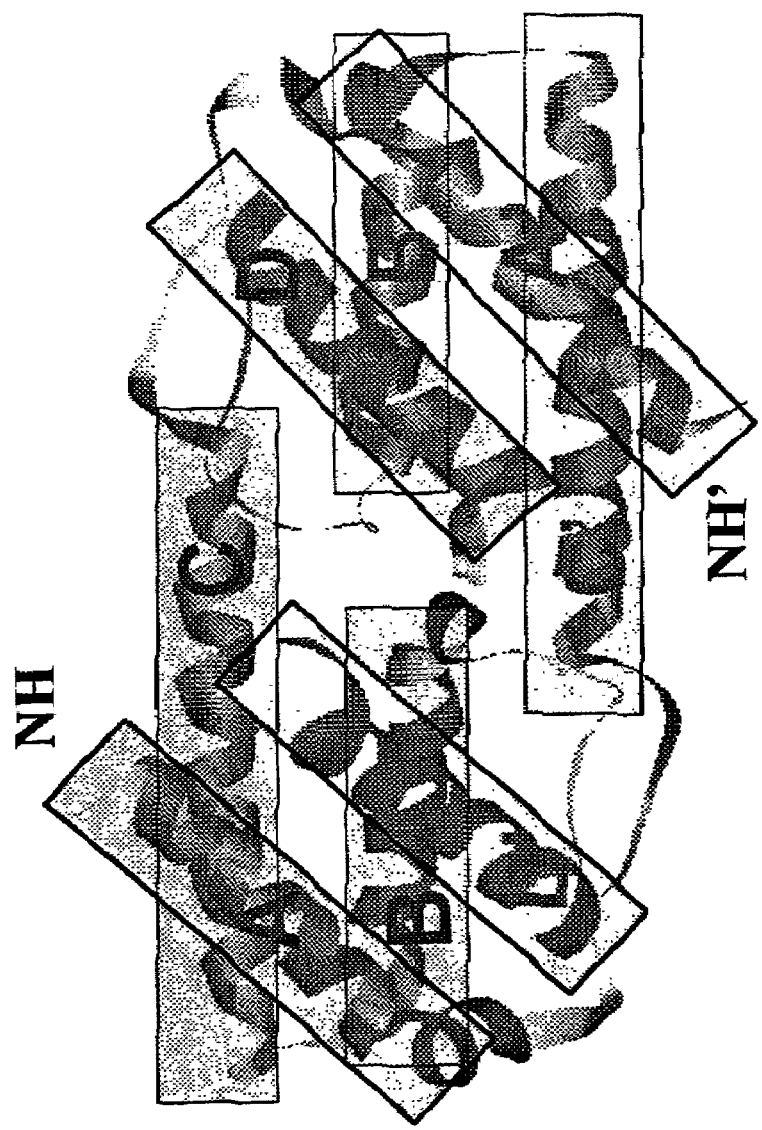
Figure 2C:
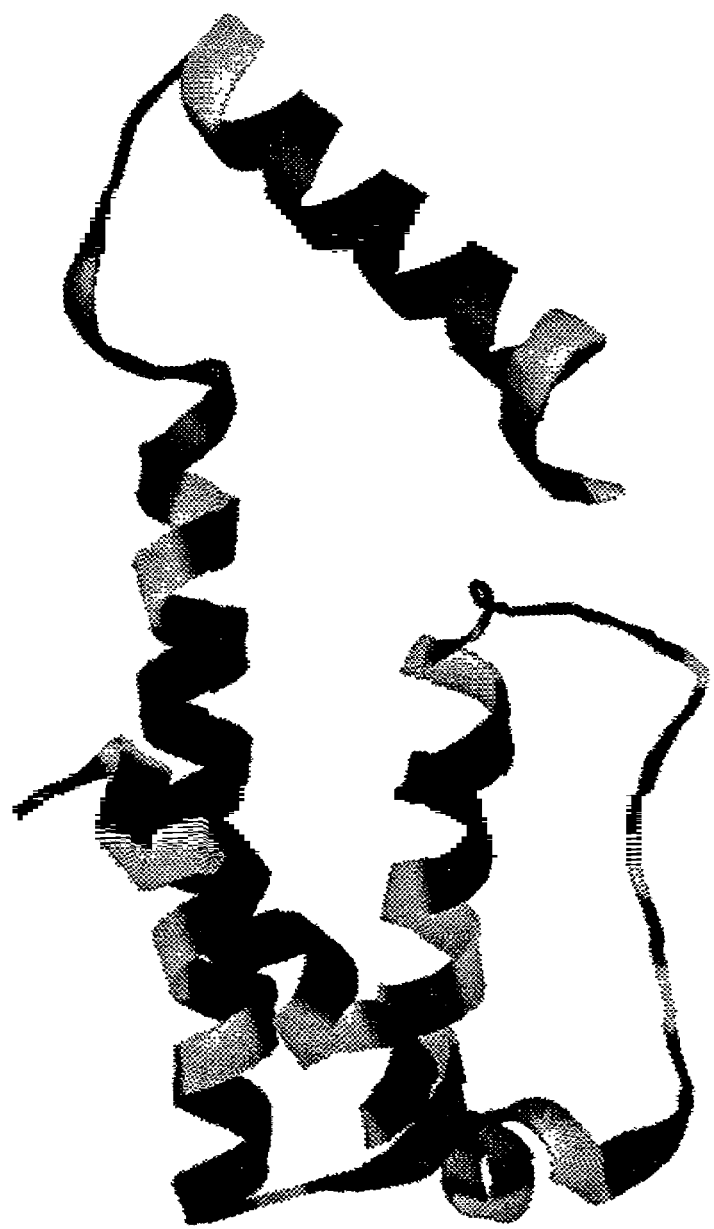

Am J Respir Crit Care Med 154 (1996) 850-7 Underwood et al "Persistent . . . ".
J Exp Med 183 (Jan. 1996) 195-201 Foster et al "Interleukin 5 deficiency."
Am J Respir Cell Mol Biol 13(1995) 360-65 Kung et al "Involvement of IL-5 . . . ".
Am J Respir Crit Care Med 151(1995) 177-83 van Oosterhout et al "Antibody . . . ".
The Journal of Immunology 155(1995) 3946-54 Villinger et al "Comparative . . . ".
Am J Respir Crit Care Med 150(1994) S50-S53 Cousins et al "Regulation . . . ".
Am Rev Respir Dis 147(1993) 548-552 van Oosterhout et al "Effect of Anti-IL . . . ".
Am Rev Respir Dis 148(1993) 1623-27 Mauser et al "Inhibitory effect of the . . . ".
J Exp Med 178(Jul. 1993) 27-47 Chiez et al "Specificity and promiscuity . . . ".
Life Sciences 53(1993) PL 243-47 Nagai et al "Effect of anti-IL-5 . . . ".
Immunology Today 13(12 (1992) 495-500 Lopez et al "GM-CSF, IL-3 and IL-5 . . . ".
Blood 78(10) (Nov. 15, 1991) 2542-47 Yamaguchi et al "Analysis of the . . . ".
The Journal of Immunology 144(4) (Feb. 15, 1990) 1345-52 Tominaga et al.
DNA 8(7) (1989) Tavernier et al "Expression of human and murine . . . ".
Nature 336(Dec. 22-29, 1988) 778-80 Sinigaglia et al "A malaria t-cell . . . ".
The Journal of Biological Chemistry 262(34) (Dec. 5, 1987) 16580-4 Tanabe.
Nucleic Acids Research 14(22) (1986) Azuma et al "Cloning of cDNA for . . . ".
Cytokine and Growth Factor Reviews, 9(1) 25-35 (1998) Takatsu "Interleukin . . . ".
Allergy and Asthma Proc. (Sep./Oct. 1998) 19(5) 257-61 Weltman et al.
J. of Allergy and Clinical Immunology, 99(1), Part 2 Broide et al.
Hertz et al. "Active Vaccination Against IL-5 Bypasses Immunological Tolerance and Ameliorates Experimental Asthma" The Journal of Immunology, 2001, 167: 3792-3799.
Nature Biotechnology 17(Jul. 1999) 666-9 Dalum et al "Therapeutic antibodies."
Intern Rev Immunol 16(1998) 227-47 Karlen et al "Biological and molecular . . . ".
J Allergy Clin Immunol 101(1998) 222-30 Barata et al "IL-4-and IL-5-positive."
The Journal of Immunology 160(1998) 4427-32 Wang et al "Selective inhibition ."
Allergy, Ed: Kaplan, AP (1997) Orgega et al Chapter 28, "Asthma".
Allergy 52(1997) 787-94 Danzig et al "Inhibition of interleukin-5 . . . ".
PubMed Abstract 9117011, Am J Respir Crit Care Med 155(3) (Mar. 1997) 819-25.
J Allergy Clin Immunol 100(1997) S56-64 Mori et al "Cellular and molecular . . . ".
J Exp Med 185(12) (Jun. 16, 1997) 2143-56 Lee et al "Interleukin-5 . . . ".
Methods: A companion ot Methods in Enzymology 11(1997) 88-97 Baumann et al.
Eur Respir J 9(Suppl 22) (1996) 72s-78s Corrigan et al "T-cell/eosinophil . . . ".
Immunity 4(Jan. 1996) 15-24 Kopf et al "IL-5 Deficient mice have . . . ".
Journal of Immunology 156(1996) 1392-1401 Huston et al "Human B cells . . . ".
Am J Respir Crit Care Med 154 (1996)850-7 Underwood et al "Persistent . . . ".
J Exp Med 183(Jan. 1996) 195-201 Foster et al "Interleukin 5 deficiency ."
The Journal of Immunology 157 (1996) 4796-4804 Dalum et al "Breaking of B . . . ".
J Mol Med 74(1996) 535-546 Dickason et al "Engineering of a functional . . . ".
Journal of Protein Chemistry 15(5) (1996) 491-99 Proudfoot et al "The carboxy ."
Nature 379 (Feb. 15, 1996) 652-55 Dickason et al "Creation of a . . . ".
Am J Respir Crit Care Med 152(1995) 467-72 Mauser et al "Effects of an . . . ".
Immunology Letters 45(1995) 109-116 Akutsu et al "Antibody against . . . ".
Int Arch Allergy Immunol 107(1995) 321-22 Egan et al "Inhibition of . . . ".
The Journal of Biological Chemistry 270(26) (Jun. 30, 1995) 15762-15769 Graber.
B J Pharmacol 113(1994) 749-56 Coeffier et al "Role of interleukin-5 . . . ".
Cytokine 6(6) (Nov. 1994) 647-56 Dickason et al "Enhanced detection . . . ".
Immunogenetics 39 (1994) 230-242 Falk et al "Pool sequencing of natural . . . ".
Thorax 49 (1994) 1231-33 Alexander et al "Serum interleukin 5 . . . ".
Am Rev Respir Dis 148 (1993) 1623-27 Mauser et al "Inhibitory effect of the . . . ".
Annals of NY Acad Sci (1993) 91-6 Nagai et al "The role of interleukin-5 . . . ".
Cell 74 (Jul. 16, 1993) 197-203 Hammer et al "Promiscuous and allele . . . ".
Eur J Biochem 212 (1993) 751-55 Graber et al "Purification, . . . ".
Eur J Biochem 211 (1993) 903-08 Kodama et al "Role of sugar chains in . . . ".
J Exp Med 178(Jul. 1993) 27-47 Chicz et al "Specificity and promiscuity . . . ".
Nature 363(May 13, 1993) 172-76 Milburn et al "A novel dimer configuration . . . ".
Biochem J 286(1992) 825-28 Rose et al "Human interleukin-5 expressed in . . . ".
European Jounal of Pharmacology 211 (1992) 121-23 Chand et al "Anti-IL-5 . . . ".
Blood 79(12) (Jun. 15, 1992) 3101-09 Sanderson "Interleukin-5, eosinophils . . . ".
Immunology Today 13(12(1992) 495-500 Lopez et al "GM-CSF, IL-3 and IL-5 . . . ".
J Exp Med 173(Feb. 1991) 429-37 Tominaga et al "Transgenic mice . . . ".
Textbook of Medicine, 1990 Ed:Souhami and Moxham, Chap 14 "Respiratory Disease".
Biochem J 270(1990) 357-61 Proudfoot et al "Preparation and . . . ".
The Journal of Immunology 145(11) (Dec. 1990) 3911-16 Sher et al "Ablation".
Science 245(Jul. 21, 1989) 308-10 Coffman et al "Antibody to interleukin-5 . . . ".
Eur J Biochem 174(1988) 345-52 Campbell et al "Isolation, structure . . . ".
Lee, James L. et al.; "Interleukin-5.." J. Exp. Med.vol. 185, No. 12, Jun. 16, 1997 2143-2156.
Danzig, M. et al; "Inhibition.." Allergy 1997: 52: 787-794.
Ortega, D. et al.; Asthma:Pathogenesis and Treatement, Chapter 28, "Allergy", W.B. Saunders Company 1997, pp. 480-505, Ed. Kaplan A.P.
Mori, A. et al; "Cellular and molecular.." J Allergy Clin Immunol vol. 100, No. 6, Part 2.
Karlin, S. et al.; "Biological and Molecular Characteristics . . . " Intern, Rev, Immunol., vol. 16, 1998, pp. 227-247.

* cited by examiner

Ile-Pro-Thr-Glu-Ile-Pro-Thr-Ser-Ala-Leu-Val-Lys-Glu-Thr-Leu-Ala-Leu-Leu-Ser-Thr-
\*   \*   Met        Met   Thr Val                                 Thr Gln   Ala

His-Arg-Thr-Leu-Leu-Ile-Ala-Asn-Glu-Thr-Leu-Arg-Ile-Pro-Val-His-Lys-Asn-
        Ala       Thr Ser           Met   Leu                 Thr

His-Gln-Leu-Cys-Thr-Glu-Glu-Ile-Phe-Gln-Gly-Ile-Gly-Thr-Leu-Glu-Ser-Gln-Thr-Val-
                    Ile Gly                       Leu Asp Ile       Lys Asn

Gln-Gly-Gly-Thr-Val-Glu-Arg-Leu-Phe-Lys-Asn-Leu-Ser-Leu-Ile-Lys-Lys-Tyr-Ile-Asp-
Arg                         Met   Gln

Gly-Gln-Lys-Lys-Lys-Cys-Gly-Glu-Glu-Arg-Arg-Arg-Val-Asn-Gln-Phe-Leu-Asp-Tyr-Leu-
Arg                 Glu                               Thr Arg

Gln-Glu-Phe-Leu-Gly-Val-Met-Asn-Thr-Glu-Trp-Ile-Ile-Glu-Ser
                    Ser                       Ala Met   Gly

Fig. 1 hIL-5  IPTEIPTSALVKETLALLSTHRTLLIANETLRIPVPVHKNHQLCTEEIFQGIGTLES  57
        *  *----***--**--  **--*---
mIL-5  MEIPMSTVVKETLTQLSAHRALLTSNETMRLPVPTKNHQLCIGEIFQGLDILKN   55

Helix A                    Loop 1    Helix B hIL-5  QTVQGGTVERLFKNLSLIKKYIDGQKKKCGEERRRVNQFLDYLQEFLGVMNTEWIIES  115
        *-*---************  -**-********--
mIL-5  QTVRGGTVEMLFQNLSLIKKYIDRQKEKCGEERRRTRQFLDYLQEFLGVMSTEWAMEG  113

Loop 2    Helix C        Loop 3    Helix D

Fig. 3

METHOD FOR DOWN-REGULATING IL5 ACTIVITY

FIELD OF THE INVENTION

The present invention relates to improvements in therapy and prevention of conditions characterized by an elevated level of eosinophil leukocytes, i.e. conditions such as asthma and other chronic allergic diseases. More specifically, the present invention provides a method for down-regulating interleukin 5 (IL5) by enabling the production of antibodies against IL5 thereby reducing the level of activity of eosinophils. The invention also provides for methods of producing modified IL5 useful in this method as well as for the modified IL5 as such. Also encompassed by the present invention are nucleic acid fragments encoding modified IL5 as well as vectors incorporating these nucleic acid fragments and host cells and cell lines transformed therewith. The invention also provides for a method for the identification of IL5 analogues which are useful in the method of the invention as well as for compositions comprising modified IL5 or comprising nucleic acids encoding the IL5 analogues.

BACKGROUND OF THE INVENTION

Asthma is a common disease of the airways, affecting about 10% of the population. The present treatments is primarily based on the administration of steroids and represents a market value exceeding well over a billion dollars. For yet unknown reasons the incidence and morbidity of asthmatics have increased worldwide over the past two decades. Today, an improved understanding of the immunological mechanisms involved in asthmatic conditions combined with an explosive development in biotechnology provides a new basis for the development of alternative and perhaps better strategies for treatment.

A general feature in the pathogenesis of asthma and other chronic allergic diseases has proven to be elevated numbers of eosinophils, especially in the bronchial mucosa of the lungs. Upon activation eosinophils secrete a number of mediators that are actively involved in the inflammatory airway response. In the activation of eosinophils, interleukin 5 (IL5) plays an important role.

IL5 is a cytokine found in many mammalian species and among others both the human and the murine gene for IL5 have been cloned (Tanabe et al., 1987, Campbell et al., 1988). The human gene consists of four exons with three introns positioned at chromosome 5 and codes for a 134 amino acid residue precursor, including a 19 amino acid N-terminal leader sequence which has the amino acid sequence set forth in SEQ ID NO: 62. Posttranslational cleavage generates the mature 115 amino acid residue protein (SEQ ID NO: 1). The murine IL5 (mIL5) gene similarly codes for a 133 amino acid residue pre-cursor with a 20 amino acid leader sequence which has the amino acid sequence set forth in SEQ ID NO: 64. The processed mature mIL5 is thus 113 amino acid residues long (SEQ ID NO: 12), missing two N-terminal amino acid residues by alignment with human IL5. The amino acid sequences of hIL5 and mIL5 are 70% identical compared to 77% at nucleotide level of the coding regions (Azuma et al., 1986). Higher similarity was reported within human primates; 99% identity is reported for the coding regions of the human and the Rhesus monkey nucleotide sequences (Villinger et al., 1995).

The human amino acid sequence has two potential N-glycosylation sites and the murine three. Human IL5 has been shown to be both N-glycosylated as well as O-glycosylated at Thr 3. Studies of hIL5 has demonstrated that the glycosylation is not necessary for the biological activity even though the stability seems to be affected by de-glycosylation (Tominaga et al., 1990; Kodama et al., 1993).

Structure of IL5

The active IL5 is a homo-dimer and the 3-dimensional structure of recombinant hIL5 has been determined by X-ray crystallography (Milburn et al., 1993). The 2 monomers are organised in an antiparallel manner and covalently bound by two interchain disulfide bridges (44-87' and 87-44'), thus engaging all 4 cysteines of the 2 monomers.

The secondary structure of the monomers consists of 4 α-helices (A-D) intermitted by 3 linking regions (loops) including two short stretches of β-sheets. This 4α helix bundle is known as the "common cytokine fold", which has also been reported for IL-2, IL-4, GM-CSF, and M-CSF. But all these are monomers and the homodimer-structure in which the D-helix completes the 4α helix motif of the opposite monomer is unique to IL5.

The native monomers alone has been shown to be biologically inactive (for reviews see Callard & Gearing, 1994; Takutsu et al., 1997). It is nevertheless possible to produce a modified recombinant biologically active monomer by inserting 8 additional amino acid residues in loop 3, connecting the helices C and D. This enables helix D to complete the 4 helix structure within one polypeptide chain and thus enable the monomer to interact with its receptor (Dickason & Huston, 1996; Dickason et al., 1996).

The IL5 receptor is primarily present on eosinophils and it is composed of an α-chain and a β-chain. The α-chain of the receptor is specific for IL5 and the β-chain, which assure high-affinity binding and signal transduction, is shared with the hetero-dimer receptors for IL-3 and GM-CSF. The sharing of a receptor component could be the reason for the cross-competition seen between IL5, IL-3 and GM-CSF (for review, see Lopez et al., 1992). However, it was recently demonstrated that the regulation of the IL5R is distinct from the regulation of the IL-3R and the GM-CSFR, further indicating a highly specialised role of IL5 in the regulation of the eosinophilic response (Wang et al., 1998).

The C-terminal part of IL5 seems to be important in both binding to the IL5R and for the biological activity, since removal of more than two C-terminal amino acid residues results in a decline in both the binding affinity to the IL5 R and in the biological activity in an IL5 bioassay (Proudfoot et al., 1996). Other residues have also been found to be important for binding to the receptor, such as Glu12, which is involved in binding to the β-chain, while the Arg90 and Glu109 residues are involved in the binding to the α-chain of the receptor. In general, binding to the IL5R seems to occur in regions overlapping helices A and D, where helix D is primarily responsible for the binding to the specific IL5R α-chain (Graber et al., 1995; Takastsu et al., 1997).

IL5's Homology to Other Proteins

The two 4-helix domain motifs seen in the homodimer has strikingly similar secondary and tertiary structure as compared to the cytokine fold found in GM-CSF and M-CSF, IL-2, IL-4 and human and porcine growth hormone (Milburn et al., 1993). However, even though striking similarities are also observed in the intron/exon organisation and position of cysteines (Tanabe et al., 1987; Cambell et al., 1988) suggesting a phylogenetic relationship with IL-2, IL-4 and GM-CSF, no significant homology with any of these or other cytokines is observed from the amino acid sequence.

Biological Activity of IL5

IL5 is mainly secreted by fully differentiated Th2 cells, mast cells and eosinophils (Cousins et al., 1994; Takutsu et al., 1997). It has been shown to act on eosinophils, basophiles, cytotoxic T lymphocytes and on murine B cells (Callard & Gearing, 1994; Takutsu et al., 1997). The effects of IL5 on human B cells are still a matter of controversy. Augmentation of immunoglobulin synthesis under certain circumstances and binding to a variety of human B cell lines have been demonstrated. Even though mRNA for the hIL5R has been found in human B-cells, the actual presence of the receptor on these cells has still to be verified (Baumann & Paul, 1997; Huston et al., 1996).

The actions of IL5 on eosinophils include chemotaxis, enhanced adhesion to endothelial cells, activation and terminal differentiation of the cells. Furthermore it has been demonstrated that IL5 prevents mature eosinophils from apoptosis (Yamaguchi et al., 1991). These findings have contributed to the present concept of IL5 as being the most important cytokine for eosinophil differentiation (Corrigan & Kay, 1996; Karlen et al., 1998).

Physiologically, IL5 and its associated eosinophil activation is considered to serve a protective role against helminthic infections and possibly against certain tumours, since these diseases are typically accompanied by peripheral blood eosinophilia (Takutsu et al., 1997; Sanderson et al., 1992). It is, however, somewhat speculative as in two studies the authors failed to show any effect beside eosinophil down-regulation following administration of antibodies against IL5 on the immunity (e.g. IgE levels) against *Nippostrongylus braziliensis* or *Schistosoma mansoni* in mice infected with these parasites (Sher et al., 1990; Coffman et al., 1989).

IL5 Transgenic and "Knock-Out" Animals

Studies of transgenic mice expressing IL5 or knock-out mice deficient for IL5 have given further knowledge of the physiological role of IL5.

Several IL5 transgenic mice have been reported:

A transgenic mouse expressing the IL5 gene in T cells was reported to have an increased white blood cell level characterised by expansion of B220+ B lymphocytes and profound eosinophilia. This was accompanied by a massive peritoneal cavity cell exudate dominated by eosinophils and infiltration of eosinophils in nearly all organ systems (Lee et al., 1997a).

Another transgenic mouse, expressing the IL5 gene under control of a metallothionin promoter was characterised by an increase in the serum levels of IgM and IgA, a massive eosinophilia in peripheral blood and many other organs accompanied by the expansion of a distinctive CD5+ B cell population, which produce auto-antibodies (Tominaga et al., 1991).

A third study involved a transgenic mouse constitutively expressing IL5 in the lungs. These animals developed pathophysiological changes resembling those of human asthma, including eosinophil invasion of peribronchial spaces, epithelial hypertrophy and increased mucus production. Furthermore, development of airway hyper responsiveness was seen in the absence of antigens (Lee et al., 1997b)

IL5-deficient mice ('knock-out' mice) have also been studied. These mice (C57BL/6) have no obvious signs of disease and are fertile. The immunoglobulin levels and the specific antibody responses to DNP-OVA were normal. Basal levels of eosinophils are produced, but are 2-3 times lower than in control animals, indicating that eosinophils can be produced in the complete absence of IL5. When these mice were infected with Mesocestoides corti the eosinophilia normally seen was abolished and this absence of eosinophilia did not affect the worm burden produced by this parasite (Kopf et al., 1996).

In a study by Foster et al. (1996), the effect of IL5 knock-out on a common model of atopic airway inflammation was investigated. Sensitisation and aerosol challenge of mice with ovalbumin normally result in airway eosinophilia, airway hyperreactivity to β-methacholin and extensive lung damage analogous to that seen in asthma. In the IL5 deficient mice the eosinophilia, airway hyperreactivity and lung damage were abolished. When IL5 expression in these mice was reconstituted, the aero-allergen induced eosinophilia and airway dysfunction were restored.

Pathophysiologic Role of IL5

Asthma affect about 10% of the population worldwide and for yet unknown reasons the incidence and morbidity have increased over the past two decades (Ortega & Busse, 1997). It is a chronic airway disease characterised by recurrent and usually reversible air flow obstruction, inflammation and hyper responsiveness (Moxam and Costello, 1990). This produces symptoms of wheezing and breathlessness, which in severe cases can be fatal.

The animal experiments referred to above using transgenic mice constitutively expressing IL5 in the lungs (Lee et al.,. 1997a) and the IL5 deficient "knock-out" mice (Foster et al., 1996) strongly implicate a crucial role of IL5 in the pathogenesis of asthma. Further evidence supporting this can be deduced from several studies including asthmatic individuals.

Eosinophilia has been identified in bronchoalveolar lavage (BAL) fluid and in bronchial mucosal biopsies of subjects with asthma and correlates with disease severity. Several eosinophil products have been identified in the BAL fluid of patients with asthma and numbers of peripheral blood eosinophils correlate with asthma severity (Ortega & Busse 1997).

IL5 serum concentration was found to be elevated (median concentration 150 pg/ml) in 15 out of 29 patients with chronic severe asthma as compared to control subjects (Alexander et al., 1994).

In another study involving both non-atopic and atopic asthmatics, it was found that an enhanced IL5 production by helper T cells seems to cause the eosinophilic inflammation of both atopic and non-atopic asthma (Mori et al., 1997).

Other results also indicate that IL5 has a distinct role in other atopic diseases. Allergen induced systemic episodes in individuals with allergic rhinitis has recently been shown to correlate to allergen induced IL5 synthesis rather than IgE (Ohashi et al., 1998). The correlation of atopic reactions is also demonstrated in a study by Barata et al. (1998) in which a significant expression of IL5 by T-cells in a cutaneous late phase reaction is demonstrated.

These and other results have led several authors as Corrigan & Kay (1996), Danzig & Cuss (1997) to identify and recommend IL5 as a primary target in the development of a better treatment for asthma and atopic diseases involving eosinophilic inflammation. Chronic tissue damaging hypereosinophilia induced by parasitic infection, topical pulmonary eosinophilia and hypereosinophilic syndrome are examples of other pathogenic conditions that could be addressed by IL5 down regulation.

In Vivo Demonstration of the Role of IL5

In several studies with rodent models of asthma it has been shown that treatment with monoclonal antibodies against IL5 (anti-IL5 mAb) results in dose-related inhibition of eosinophilia, as compared to non-treated controls (Nagai et al., 1993a & b; Chand et al., 1992; Coeffier et al., 1994; Kung et al., 1995; Underwood et al., 1996). In the study by Nagai et al. (1993a) the effect was also observed by treating the sensitised Balb/c mice with soluble IL5 receptor α.

In one study with Balb/c mice (Hamelmann et al., 1997) and four studies with guinea pigs it was additionally shown that anti-IL5 mAb could inhibit airway hyperreactivity elicited with various substances in antigen sensitised animals (Mauser et al., 1993; Akutsu et al., 1995; van Oosterhout et al., 1995 & 1993). In some of the studies beneficial effects (cf. table 1) of the anti-IL5 mAb treatment were also observed microscopically (Mauser et al., 1993; Akutsu et al., 1995; Kung et al., 1995). Importantly, in the study by Kung et al. (1995) a reduction of pulmonary inflammation in B6D2F1 mice was seen both when anti-IL5 mAb was administered hours before antigen challenge and also when administered up to five days after antigen challenge, indicating that the effect of anti-IL5 mAb may be both prophylactic and therapeutic for airway inflammation. This effect, however, was not observed by Underwood et al. when guinea pigs were given anti-IL5 mAb two hours after antigen challenge (Underwood et al., 1996).

In a study using a monkey model of asthma, Mauser et al. (1995) reported an inhibition of airway hyper reactivity after antigen challenge, when rat anti mouse-IL5 mAb was given 1 hour before antigen challenge. In addition, there was 75% reduction in the number of eosinophils in bronchoalveolar lavage (BAL) of antibody treated animals, as compared to non-treated controls. The effects on eosinophilia and hyperresponsiveness of anti-IL5 mAb was seen for up to three months after treatment (Mauser et al., 1995). Regarding allergic hyperresponsiveness, the results from studies by Nagai et al. (1993a and 1993b) document no reduction in hyperresponsiveness in conjunction to a reduction of eosinophil numbers in BAL.

All anti-IL5 mAb in vivo experiments mentioned so far have been done with rat-anti-mouse monoclonal antibodies. Egan et al. (1995) have reported experiments using humanised rat-anti-human IL5 monoclonal antibodies, called Sch 55700. These mAbs, inhibited lung lavage eosinophilia by 75% at a dose of 0,3 mg/kg when administered to sensitised monkeys. When Sch 55700 was given at 1 mg/kg in allergic mice, inhibition of airway eosinophilia was also observed.

Treatment of Asthma at Present and in the Future

The current treatment of asthma is, as mentioned, corticosteproids which, by their anti-inflammatory action, are the most powerful drugs. Besides this, $\beta_2$ agonists and methyl xanthine derivatives which all cause bronchodilation, and disodium chromoglycate which 'stabilises' mast cells, thereby preventing mediator release, all have proven beneficial in asthma patients (Ortega & Busse 1997).

Future treatment of asthma may as discussed above include anti-IL5 mAbs. Celltech in corporation with Schering Plough have anti-IL5 mAb in phase I clinical trial for treatment of asthma. However, treatment with monoclonal antibodies entails a number of drawbacks. First of all, the development and production costs for a safe mAB (e.g. a humanised mAB) are very high, resulting in an expensive therapeutic product for the end user. Second, mABs have the disadvantageous characteristic seen from a patient point of view that they have to be administered with relatively short intervals. Third, by nature mABs exhibit a narrow specificity against one single epitope of the antigen. And, finally, mABs (even humanised) are immunogenic, leading to an increasingly fast inactivation of administered antibodies as treatment progresses over time.

Also use of antisense IL5 oligonucleotides for antisense therapy has been suggested by the company Hybridon for the treatment of asthma, allergies and inflammation. However, the antisense technology has proven to be technically difficult and, in fact, conclusive evidence of the feasibility of antisense therapy in humans has not yet been established.

Finally, WO 97/45448 (Bresagen Limited/Medvet Science) proposes the use of "modified and variant forms of IL5 molecules capable of antagonising the activity of IL5" in ameliorating, abating or otherwise reducing the aberrant effects caused by native or mutant forms of IL5. The antagonizing effect is reported to be the result of the variant forms of IL5 binding to the low affinity a chain of IL5R but not to the high affinity receptors; in this way the variants compete with IL5 for binding to its receptors without exerting the physiological effects of IL5.

Other atopic diseases involving eosinophilic inflammation are treated with either the symptomatica mentioned for asthma or immune therapy (IT) using hyposensitization with allergen extracts. The latter type of treatment is known to be effective against allergies against one or a few antigens, whereas IT is not feasible in the treatment of multiple allergies. Furthermore, the time scale for obtaining clinical improvement in patients susceptible to treatment is very long for conventional IT.

Thus, in spite of existing and possible future therapies for chronic allergic diseases such as asthma, there is a definite need for alternative ways of treating and ameliorating this and other chronic allergic diseases.

OBJECT OF THE INVENTION

The object of the present invention is to provide novel therapies against chronic allergic conditions (such as asthma) characterized by eosinophilia. A further object is to develop an autovaccine against IL5, in order to obtain a novel treatment for asthma and for other pathological disorders involving chronic airway inflammation.

SUMMARY OF THE INVENTION

The T-cell derived cytokine IL5 has, as mentioned above, a crucial role in orchestrating the eosinophilic response, affecting both the production, the localisation and the activation of eosinophils. As IL5 has not otherwise been reported to have a central role in the development of a protective immune response, this particular cytokine is in the opinion of the inventors an attractive therapeutic target for the treatment of asthma.

The general aim according to the present invention is to decrease the pathogenic levels of eosinophils in the airways of the asthma patient by down-regulating of the IL5 levels, since eosinophils depend on IL5 for attraction and activation. The result of a decreased eosinophil number in the airway mucosa would be a concomitant decrease in the airway inflammation, corresponding to a clinical improvement in the asthmatic patient.

The potential effect of such an approach has already been demonstrated in studies using anti IL5 monoclonal antibodies in animal models of airway inflammation, cf. the "PREAMBLE TO EXAMPLES".

This current invention, however, takes the results obtained through passive immunisation one step further by using the approach of generating an active immune response through the concept of autovaccination. To the best of the inventor's knowledge, such an approach has never been suggested before.

The advantage of treating asthmatics with an IL5 autovaccine, as compared to current treatment with corticosteroids etc., is a reduction and/or elimination of side effects and most likely a better effect in terms of duration. When compared to anti-IL5 mAbs, the effect of an induced polyclonal Ab response is expected to be superior to passively injected monoclonal immunoglobulins since the polyclonal response has a broader specificity. Improvements with respect to administration regimen are also expected (since effective autovaccines described herein typically would require a maximum of 2-6 administrations per year).

When compared to hyposensitization, the present invention offers the attractive aspect of being non-specific; this is especially relevant when dealing with multi-allergic patients.

Thus, in its broadest and most general scope, the present invention relates to a method for in vivo down-regulation of interleukin 5 (IL5) activity in an animal, including a human being, the method comprising effecting presentation to the animal's immune system of an immunologically effective amount of

- at least one IL5 polypeptide or subsequence thereof which has been formulated so that immunization of the animal with the IL5 polypeptide or subsequence thereof induces production of antibodies against the IL5 polypeptide, and/or
- at least one IL5 analogue wherein is introduced at least one modification in the IL5 amino acid sequence which has as a result that immunization of the animal with the analogue induces production of antibodies against the IL5 polypeptide.

The most attractive aspect of this approach is that e.g. asthma can be controlled by periodic but not very frequent immunizations, in contrast to a therapeutic approach which involves administration of anti-IL5 or molecules having a binding affinity to IL5 analogous therewith. It is expected that 1-4 annual injections with an immunogenic composition according to the invention will be sufficient to obtain the desired effect, whereas administration of other inhibitors of IL5 activity does or will require daily, or at least weekly, administrations.

The invention also relates to IL5 analogues as well as to nucleic acid fragments encoding a subset of these. Also immunogenic compositions comprising the analogues or the nucleic acid fragments are part of the invention.

The invention also relates to a method of identifying analogues of IL5 as well as a method for preparing a composition comprising the IL5 analogues.

LEGENDS TO THE FIGURES

FIG. 1: The amino acid sequence of the mature human IL5 (SEQ ID NO: 1). The aligned murine sequence is included (SEQ ID NO: 12), but only positions that differ from the human sequence are displayed. The two "+"s indicate the missing N-terminal residues of the murine IL5. The N-glycosylation positions are marked with double underlining, the O-glycosylated threonines of human IL5 are given in italics, and the cysteines in bold.

FIG. 2: The dimer and monomer structures of human IL5.

- A: Dimer structure of hIL5. The structure has only been obtained for residues 5-112, which means that the O-glycosylation site at Thr3 is not included.
- B: The same structure as in A, with the assignment of the helices (A-D and A'-D').
- C: The monomer hIL5 with the amino acid residues differing from the mIL5 shown in light grey.

FIG. 3: The aligned mature human IL5 (hIL5) and murine IL5 (mIL5) amino acid sequences (SEQ ID NOs: 1 and 12) with indications of suitable substitution regions. The 4 α-helices A-D are surrounded by solid-line boxes, the β-sheets are double underlined and the positions of the two cysteines are marked with "▼". Identical residues in the two sequences are marked with "-" and non-identical residues with "*". Loop 1 spans between helices A and B, Loop 2 spans between helices B and C, and loop 3 spans between loops C and D. Amino acid sequences to be substituted with foreign $T_H$ epitope containing peptides are marked in bold; one such sequence is surrounded by a dot-lined box because of residues overlapping with those substituted in a different construct. The amino acid sequences of 10 constructs (5 derived from human and 5 derived from murine IL5) are set forth in SEQ ID NOs: 2-11 and 13-22.

FIG. 4: ELISA results of DNA immunization testing two mILS autovaccine DNA vaccines.

Mice were DNA vaccinated with naked plasmid DNA encoding either ovalbumin, mIL5wt, mIL5.1 or mIL5.5. Sera obtained at day 77 were tested for reactivity against ovalbumin and murine IL5. Polystyrene microtiter plates (Maxisorp, Nunc) were coated with ovalbumin (1 μg/well, Sigma) or purified recombinant murine IL5 (0.1 μg/well, E1320). The reactivities of diluted sera added to the wells were visualised using a goat anti-mouse secondary antibody. OD490 readings of the pre-bleeds were subtracted from the OD490 readings of the test samples, and the resulting values were presented for each individual mouse as bars. The OD490 readings of the pre-bleeds (in 1:25 dilution) were ranging from 0.025-0.034. Crucifixes indicate dead animals.

FIG. 5: Schematic representation of murine IL5 based autovaccine constructs.

The top figure represents murine wild-type IL5 monomer with helices A-C, loops 1-3 and the flexible C-terminal region. Remaining figures represent different autovaccine constructs having in-substitutions of the tetanus toxoid epitopes P2 and P30 in various positions. Specific constructs are detailed in the Examples.

DETAILED DISCLOSURE OF THE INVENTION

Definitions

In the following, a number of terms used in the present specification and claims will be defined and explained in detail in order to clarify the metes and bounds of the invention.

The terms "T-lymphocyte" and "T-cell" will be used interchangeably for lymphocytes of thymic origin which are responsible for various cell mediated immune responses as well as for helper activity in the humeral immune response. Likewise, the terms "B-lymphocyte" and "B-cell" will be used interchangeably for antibody-producing lymphocytes.

An "IL5 polypeptide" is herein intended to denote polypeptides having the amino acid sequence of the above-discussed IL5 proteins derived from humans and mice (or truncates thereof sharing a substantial amount of B-cell epitopes with intact IL5), but also polypeptides having the amino acid sequence identical to xeno-analogues of these two proteins isolated from other species are embraced by the term. Also unglycosylated forms of IL5 which are prepared in prokaryotic system are included within the boundaries of the term as are forms having varying glycosylation patterns due to the use of e.g. yeasts or other non-mammalian eukaryotic expression systems. It should, however, be noted that when using the term "an IL5 polypeptide" it is intended that the polypeptide in question is normally non-immunogenic when presented to the animal to be treated. In other words, the IL5 polypeptide is a self-protein or is a xeno-analogue of such a self-protein which will not normally give rise to an immune response against IL5 of the animal in question.

An "IL5 analogue" is an IL5 polypeptide which has been subjected to changes in its primary structure. Such a change can e.g. be in the form of fusion of an IL5 polypeptide to a suitable fusion partner (i.e. a change in primary structure exclusively involving C- and/or N-terminal additions of amino acid residues) and/or it can be in the form of insertions and/or deletions and/or substitutions in the IL5 polypeptide's amino acid sequence. Also encompassed by the term are derivatized IL5 molecules, cf. the discussion below of modifications of IL5.

It should be noted that the use as a vaccine in a human of e.g. a canine analogue of human IL5 can be imagined to produce the desired immunity against IL5. Such use of an xeno-analogue for immunization is also considered to be an "IL5 analogue" as defined above.

When using the abbreviation "IL5" herein, this is intended as a reference to the amino acid sequence of mature, wildtype IL5 (also denoted "IL5 m" and "IL5 wt" herein). Mature human IL5 is denoted hIL5, hIL5m or hIL5wt, and murine mature IL5 is denoted mIL5, mIL5m, or mIL5 wt. In cases where a DNA construct includes information encoding a leader sequence or other material, this will normally be clear from the context.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring IL5 amino acid sequence or nucleic acid sequence, respectively.

The term "animal" is in the present context in general intended to denote an animal species (preferably mammalian), such as Homo sapiens, Canis domesticus, etc. and not just one single animal. However, the term also denotes a population of such an animal species, since it is important that the individuals immunized according to the method of the invention all harbour substantially the same IL5 allowing for immunization of the animals with the same immunogen(s). If, for instance, genetic variants of IL5 exists in different human population it may be necessary to use different immunogens in these different populations in order to be able to break the autotolerance towards IL5 in each population. It will be clear to the skilled person that an animal in the present context is a living being which has an immune system. It is preferred that the animal is a vertebrate, such as a mammal.

By the term "in vivo down-regulation of IL5 activity" is herein meant reduction in the living organism of the number of interactions between IL5 and its receptors (or between IL5 and other possible biologically important binding partners for this molecule). The down-regulation can be obtained by means of several mechanisms: Of these, simple interference with the active site in IL5 by antibody binding is the most simple. However, it is also within the scope of the present invention that the antibody binding results in removal of IL5 by scavenger cells (such as macrophages and other phagocytic cells).

The expression "effecting presentation . . . to the immune system" is intended to denote that the animal's immune system is subjected to an immunogenic challenge in a controlled manner. As will appear from the disclosure below, such challenge of the immune system can be effected in a number of ways of which the most important are vaccination with polypeptide containing "pharmaccines" (i.e. a vaccine which is administered to treat or ameliorate ongoing disease) or nucleic acid "pharmaccine" vaccination. The important result to achieve is that immune competent cells in the animal are confronted with the antigen in an immunologically effective manner, whereas the precise mode of achieving this result is of less importance to the inventive idea underlying the present invention.

The term "immunogenically effective amount" has its usual meaning in the art, i.e. an amount of an immunogen which is capable of inducing an immune response which significantly engages pathogenic agents which share immunological features with the immunogen.

When using the expression that the IL5 has been "modified" is herein meant a chemical modification of the polypeptide which constitutes the backbone of IL5. Such a modification can e.g. be derivatization (e.g. alkylation, acylation, esterification etc.) of certain amino acid residues in the IL5 sequence, but as will be appreciated from the disclosure below, the preferred modifications comprise changes of (or additions to) the primary structure of the IL5 amino acid sequence.

When discussing "autotolerance towards IL5" it is understood that since IL5 is a self-protein in the population to be vaccinated, normal individuals in the population do not mount an immune response against IL5; it cannot be excluded, though, that occasional individuals in an animal population might be able to produce antibodies against native IL5, e.g. as part of an autoimmune disorder. At any rate, an animal will normally only be autotolerant towards its own IL5, but it cannot be excluded that IL5 analogues derived from other animal species or from a population having a different IL5 phenotype would also be tolerated by said animal.

A "foreign T-cell epitope" (or: "foreign T-lymphocyte epitope") is a peptide which is able to bind to an MHC molecule and which stimulates T-cells in an animal species. Preferred foreign T-cell epitopes in the invention are "promiscuous" epitopes, i.e. epitopes which bind to a substantial fraction of a particular class of MHC molecules in an animal species or population. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same IL5 analogue or 2) prepare several IL5 analogues wherein each analogue has a different promiscuous epitope inserted. It should be noted also that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope which binds an MHC Class II molecule and can be presented on the surface of an antigen presenting cell (APC) bound to the MHC Class II molecule.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention. For instance it is possible to use certain other cytokines as a modifying moiety in IL5 (cf. the detailed discussion below), and in such a case, the issue of stability may be irrelevant since the coupling to IL5 provides the stability necessary.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combination of vaccination with immunogen and adjuvant induces an immune response against the immunogen which is stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the molecule in a composition facilitating targeting or by introduction in the molecule of groups which facilitates targeting. These issues will be discussed in detail below.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen Preferred Embodiments of IL5 Activity Down-Regulation It is preferred that the IL5 polypeptide used as an immunogen in the method of the invention is a modified molecule wherein at least one change is present in the IL5 amino acid sequence, since the chances of obtaining the all-important breaking of autotolerance towards IL5 is greatly facilitated that way. It should be noted that this does not exclude the possibility of using such a modified IL5 in formulations which further facilitate the breaking of autotolerance against IL5, e.g. formulations containing certain adjuvants discussed in detail below.

It has been shown (in Dalum I et al., 1996, J. Immunol. 157: 4796-4804) that potentially self-reactive B-lymphocytes recognizing self-proteins are physiologically present in normal individuals. However, in order for these B-lymphocytes to be induced to actually produce antibodies reactive with the relevant self-proteins, assistance is needed from cytokine producing T-helper lymphocytes ($T_H$-cells or $T_H$-lymphocytes). Normally this help is not provided because T-lymphocytes in general do not recognize T-cell epitopes derived from self-proteins when presented by antigen presenting cells (APCs). However, by providing an element of "foreignness" in a self-protein (i.e. by introducing an immunologically significant modification), T-cells recognizing the foreign element are activated upon recognizing the foreign epitope on an APC (such as, initially, a mononuclear cell). Polyclonal B-lymphocytes (which are also specialised APCs) capable of recognising self-epitopes on the modified self-protein also internalise the antigen and subsequently presents the foreign T-cell epitope(s) thereof, and the activated T-lymphocytes subsequently provide cytokine help to these self-reactive polyclonal B-lymphocytes. Since the antibodies produced by these polyclonal B-lymphocytes are reactive with different epitopes on the modified polypeptide, including those which are also present in the native polypeptide, an antibody cross-reactive with the non-modified self-protein is induced. In conclusion, the T-lymphocytes can be led to act as if the population of polyclonal B-lymphocytes have recognised an entirely foreign antigen, whereas in fact only the inserted epitope(s) is/are foreign to the host. In this way, antibodies capable of cross-reacting with non-modified self-antigens are induced.

Several ways of modifying a peptide self-antigen in order to obtain breaking of autotolerance are known in the art. Hence, according to the invention, the modification can include that at least one foreign T-cell epitope is introduced, and/or at least one first moiety is introduced which effects targeting of the modified molecule to an antigen presenting cell (APC), and/or at least one second moiety is introduced which stimulates the immune system, and/or at least one third moiety is introduced which optimises presentation of the modified IL5 polypeptide to the immune system.

However, all these modifications should be carried out while maintaining a substantial fraction of the original B-lymphocyte epitopes in IL5, since the B-lymphocyte recognition of the native molecule is thereby enhanced.

In one preferred embodiment, side groups (in the form of foreign T-cell epitopes or the above-mentioned first, second and third moieties) are covalently or non-covalently introduced. This is intended to mean that stretches of amino acid residues derived from IL5 are derivatized without altering the primary amino acid sequence, or at least without introducing changes in the peptide bonds between the individual amino acids in the chain.

An alternative, and preferred, embodiment utilises amino acid substitution and/or deletion and/or insertion and/or addition (which may be effected by recombinant means or by means of peptide synthesis; modifications which involves longer stretches of amino acids can give rise to fusion polypeptides). One especially preferred version of this embodiment is the technique described in WO 95/05849, which discloses a method for down-regulating self-proteins by immunising with analogues of the self-proteins wherein a number of amino acid sequencers) has been substituted with a corresponding number of amino acid sequence(s) which each comprise a foreign immunodominant T-cell epitope, while at the same time maintaining the overall tertiary structure of the self-protein in the analogue. For the purposes of the present invention, it is however sufficient if the modification (be it an amino acid insertion, addition, deletion or substitution) gives rise to a foreign T-cell epitope and at the same time preserves a substantial number of the B-cell epitopes in IL5. However, in order to obtain maximum efficacy of the immune response induced, it is preferred that the overall tertiary structure of IL5 is maintained in the modified molecule.

The following formula describes the IL5 constructs generally covered by the invention:

$$(MOD_1)_{s1}(IL5_{e1})_{n1}(MOD_2)_{s2}(IL5_{e2})_{n2} \ldots (MOD_x)_{sx}(IL5_{ex})_{nx} \quad (I)$$

where $IL5_{e1}$-$IL5_{ex}$ are x B-cell epitope containing subsequences of IL5 which independently are identical or non-identical and which may contain or not contain foreign side groups, x is an integer$\geq 3$, n1–nx are x integers$\geq 0$ (at least one is $\geq 1$), $MOD_1$-$MOD_x$ are x modifications introduced between the preserved B-cell epitopes, and $s_1$-$s_x$ are x integers$\geq 0$ (at least one is $\geq 1$ if no side groups are introduced in the IL5e sequences). Thus, given the general functional restraints on the immunogenicity of the constructs, the invention allows for all kinds of permutations of the original IL5 sequence, and all kinds of modifications therein. Thus, included in the invention are modified IL5 obtained by omission of parts of the IL5 sequence which e.g. exhibit adverse effects in vivo or omission of parts which could give rise to undesired immunological reactions.

Maintenance of a substantial fraction of B-cell epitopes or even the overall tertiary structure of a protein which is subjected to modification as described herein can be achieved in several ways. One is simply to prepare a polyclonal antiserum directed against IL5 (e.g. an antiserum prepared in a rabbit) and thereafter use this antiserum as a test reagent (e.g. in a competitive ELISA) against the modified proteins which are produced. Modified versions (analogues) which react to the same extent with the antiserum as does IL5 must be regarded as having the same overall tertiary structure as IL5 whereas analogues exhibiting a limited (but still significant and specific) reactivity with such an antiserum are regarded as having maintained a substantial fraction of the original B-cell epitopes.

Alternatively, a selection of monoclonal antibodies reactive with distinct epitopes on IL5 can be prepared and used as a test panel. This approach has the advantage of allowing 1) an epitope mapping of IL5 and 2) a mapping of the epitopes which are maintained in the analogues prepared.

Of course, a third approach would be to resolve the 3-dimensional structure of IL5 or of a biologically active truncate thereof (cf. above) and compare this to the resolved three-dimensional structure of the analogues prepared. Three-dimensional structure can be resolved by the aid of X-ray diffraction studies and NMR-spectroscopy. Further information relating to the tertiary structure can to some extent be obtained from circular dichroism studies which have the advantage of merely requiring the polypeptide in pure form (whereas X-ray diffraction requires the provision of crystallized polypeptide and NMR requires the provision of isotopic variants of the polypeptide) in order to provide useful information about the tertiary structure of a given molecule. However, ultimately X-ray diffraction and/or NMR are necessary to obtain conclusive data since circular dichroism can only provide indirect evidence of correct 3-dimensional structure via information of secondary structure elements.

One preferred embodiment of the invention utilises multiple presentations of B-lymphocyte epitopes of IL5 (i.e. formula I wherein at least one B-cell epitope is present in two positions). This effect can be achieved in various ways, e.g. by simply preparing fusion polypeptides comprising the structure $(IL5)_m$, where m is an integer$\geq 2$ and then introduce the modifications discussed herein in at least one of the IL5 sequences, or alternatively, inserted between at least two of the IL5 amino acid sequences. It is preferred that the modifications introduced includes at least one duplication of a B-lymphocyte epitope and/or the introduction of a hapten.

As mentioned above, the introduction of a foreign T-cell epitope can be accomplished by introduction of at least one amino acid insertion, addition, deletion, or substitution. Of course, the normal situation will be the introduction of more than one change in the amino acid sequence (e.g. insertion of or substitution by a complete T-cell epitope) but the important goal to reach is that the IL5 analogue, when processed by an antigen presenting cell (APC), will give rise to such a foreign immunodominant T-cell epitope being presented in context of an MCH Class II molecule on the surface of the APC. Thus, if the IL5 amino acid sequence in appropriate positions comprises a number of amino acid residues which can also be found in a foreign $T_H$ epitope then the introduction of a foreign $T_H$ epitope can be accomplished by providing the remaining amino acids of the foreign epitope by means of amino acid insertion, addition, deletion and substitution. In other words, it is not necessary to introduce a complete $T_H$ epitope by insertion or substitution.

It is preferred that the number of amino acid insertions, deletions, substitutions or additions is at least 2, such as 3, 4, 5, 6, 7, 8, 9, 10, 11, 12, 13, 14, 15, 16, 17, 18, 19, 20, and 25 insertions, substitutions, additions or deletions. It is furthermore preferred that the number of amino acid insertions, substitutions, additions or deletions is not in excess of 150, such as at most 100, at most 90, at most 80, and at most 70. It is especially preferred that the number of substitutions, insertions, deletions, or additions does not exceed 60, and in particular the number should not exceed 50 or even 40. Most preferred is a number of not more than 30. With respect to amino acid additions, it should be noted that these, when the resulting construct is in the form of a fusion polypeptide, is often considerably higher than 150.

Preferred embodiments of the invention includes modification by introducing at least one foreign immunodominant $T_H$ epitope. It will be understood that the question of immune dominance of a $T_H$ epitope depends on the animal species in question. As used herein, the term "immunodominance" simply refers to epitopes which in the vaccinated individual gives rise to a significant immune response, but it is a well-known fact that a $T_H$ epitope which is immunodominant in one individual is not necessarily immunodominant in another individual of the same species, even though it may be capable of binding MHC-II molecules in the latter individual.

Another important point is the issue of MHC restriction of TH epitopes. In general, naturally occurring $T_H$ epitopes are MHC restricted, i.e. a certain peptide constituting a $T_H$ epitope will only bind effectively to a subset of MHC Class II molecules. This in turn has the effect that in most cases the use of one specific $T_H$ epitope will result in a vaccine component which is effective in a fraction of the population only, and depending on the size of that fraction, it can be necessary to include more $T_H$ epitopes in the same molecule, or alternatively prepare a multi-component vaccine wherein the components are IL5 variants which are distinguished from each other by the nature of the $T_H$ epitope introduced.

If the MHC restriction of the T-cells used is completely unknown (for instance in a situation where the vaccinated animal has a poorly defined MHC composition), the fraction of the animal population covered by a specific vaccine composition can be determined by means of the following formula:

$$f_{population} = 1 - \prod_{r=1}^{n} (1 - p_j) \quad (II)$$

where $p_i$ is the frequency in the population of responders to the $i^{th}$ foreign T-cell epitope present in the vaccine composition, and n is the total number of foreign T-cell epitopes in the vaccine composition. Thus, a vaccine composition containing 3 foreign T-cell epitopes having response frequencies in the population of 0.8, 0.7, and 0.6, respectively, would give

1−0.2×0.3×0.4=0.976 i.e. 97.6 percent of the population will statistically mount an MHC-II mediated response to the vaccine.

The above formula does not apply in situations where a more or less precise MHC restriction pattern of the peptides used is known. If, for instance a certain peptide only binds the human MHC-II molecules encoded by HLA-DR alleles DR1, DR3, DR5, and DR7, then the use of this peptide together with another peptide which binds the remaining MHC-II molecules encoded by HLA-DR alleles will accomplish 100% coverage in the population in question. Likewise, if the second peptide only binds DR3 and DR5, the addition of this peptide will not increase the coverage at all. If one bases the calculation of population response purely on MHC restriction of T-cell epitopes in the vaccine, the fraction of the population covered by a specific vaccine composition can be determined by means of the following formula:

$$f_{population} = 1 - \prod_{j=1}^{3} (1 - \varphi_j)^2 \quad (III)$$

wherein $\phi_j$ is the sum of frequencies in the population of allelic haplotypes encoding MHC molecules which bind any one of the T-cell epitopes in the vaccine and which belong to the $j^{th}$ of the 3 known HLA loci (DP, DR and DQ); in practice, it is first determined which MHC molecules will recognize each T-cell epitope in the vaccine and thereafter these MHC molecules are listed by type (DP, DR and DQ)—then, the individual frequencies of the different listed allelic haplotypes are summed for each type, thereby yielding $\phi_1$, $\phi_2$, and $\phi_3$.

It may occur that the value $p_i$ in formula II exceeds the corresponding theoretical value $\pi_i$:

$$\pi_i = 1 - \prod_{j=1}^{3} (1 - v_j)^2 \quad (IV)$$

wherein $v_j$ is the sum of frequencies in the population of allelic haplotypes encoding MHC molecules which bind the $i^{th}$ T-cell epitope in the vaccine and which belong to the $j^{th}$ of the 3 known HLA loci (DP, DR and DQ). This means that in $1-\pi_i$ of the population there is a frequency of responders of $f_{residual\_i}=(p_i-\pi_i)/(1-\pi_i)$. Therefore, formula III can be adjusted so as to yield formula V:

$$f_{population} = 1 - \prod_{j=1}^{3} (1 - \varphi_i)^2 + \left(1 - \prod_{r=1}^{n} (1 - f_{residual\_i})\right) \quad (V)$$

where the term $1-f_{residual_i}$ is set to zero if negative. It should be noted that formula V requires that all epitopes have been haplotype mapped against identical sets of haplotypes.

Therefore, when selecting T-cell epitopes to be introduced in the IL5 analogue, it is important to include all knowledge of the epitopes which is available: 1) The frequency of responders in the population to each epitope, 2) MHC restriction data, and 3) frequency in the population of the relevant haplotypes.

There exists a number of naturally occurring "promiscuous" T-cell epitopes which are active in a large proportion of individuals of an animal species or an animal population and these are preferably introduced in the vaccine, thereby reducing the need for a very large number of different IL5 analogues in the same vaccine.

The promiscuous epitope can according to the invention be a naturally occurring human T-cell epitope such as epitopes from tetanus toxoid (e.g. the P2 and P30 epitopes), diphtheria toxoid, Influenza virus hemagluttinin (HA), and *P. falciparum* CS antigen.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in the IL5 analogues used according to the present invention. Cf. also the epitopes discussed in the following references which are hereby all incorporated by reference herein: WO 98/23635 (Frazer I H et al., assigned to The University of Queensland); Southwood S et. al, 1998, J. Immunol. 160: 3363-3373; Sinigaglia F et al., 1988, Nature 336: 778-780; Chicz R M et al., 1993, J. Exp. Med 178: 27-47; Hammer J et al., 1993, Cell 74: 197-203; and Falk K et al., 1994, Immunogenetics 39: 230-242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope which is capable of binding a large proportion of MHC Class II molecules. In this context the pan DR epitope peptides ("PADRE") described in WO 95/07707 and in the corresponding paper Alexander J et al., 1994, Immunity 1: 751-761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the modified IL5 which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE peptide is the one having the amino acid sequence AKFVAAWTLKAAA (SEQ ID NO: 65) or an immunologically effective subsequence thereof. This, and other epitopes having the same lack of MHC restriction are preferred T-cell epitopes which should be present in the IL5 analogues used in the inventive method. Such super-promiscuous epitopes will allow for the most simple embodiments of the invention wherein only one single modified IL5 is presented to the vaccinated animal's immune system.

As mentioned above, the modification of IL5 can also include the introduction of a first moiety which targets the modified IL5 to an APC or a B-lymphocyte. For instance, the first moiety can be a specific binding partner for a B-lymphocyte specific surface antigen or for an APC specific surface antigen. Many such specific surface antigens are known in the art. For instance, the moiety can be a carbohydrate for which there is a receptor on the B-lymphocyte or on the APC (e.g. mannan or mannose). Alternatively, the second moiety can be a hapten.

Also an antibody fragment which specifically recognizes a surface molecule on APCs or lymphocytes can be used as a first moiety (the surface molecule can e.g. be an FCγ receptor of macrophages and monocytes, such as FCγRI or, alternatively any other specific surface marker such as CD40 or CTLA-4). It should be noted that all these exemplary targeting molecules can be used as part of an adjuvant also, cf. below.

As an alternative or supplement to targeting the modified IL5 polypeptide to a certain cell type in order to achieve an enhanced immune response, it is possible to increase the level of responsiveness of the immune system by including the above-mentioned second moiety which stimulates the immune system. Typical examples of such second moieties are cytokines, and heat-shock proteins or molecular chaperones, as well as effective parts thereof.

Suitable cytokines to be used according to the invention are those which will normally also function as adjuvants in a vaccine composition, i.e. for instance interferon γ (IFN-γ), Flt3L, interleukin 1 (IL-1), interleukin 2 (IL-2), interleukin 4 (IL-4), interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below. It should be noted that use of both IL-4 and IL-13 should be exercised very carefully, if at all, as both molecules are known as key effector molecules in the pathophysiology of atopy and asthma.

According to the invention, suitable heat-shock proteins or molecular chaperones used as the second moiety can be HSP70, HSP90, HSC70, GRP94 (also known as gp96, cf. Wearsch P A et al. 1998, Biochemistry 37: 5709-19), and CRT (calreticulin). Alternatively, the second moiety can be a toxin, such as listeriolycin (LLO), lipid A and heat-labile enterotoxin. Also, a number of mycobacterial derivatives such as MDP (muramyl dipeptide) and the trehalose diesters TDM and TDE are interesting possibilities.

Also the possibility of introducing a third moiety which enhances the presentation of the modified IL5 to the immune system is an important embodiment of the invention. The art has shown several examples of this principle. For instance, it is known that the palmitoyl lipidation anchor in the Borrelia burgdorferi protein OspA can be utilised so as to provide self-adjuvating polypeptides (cf. e.g. WO 96/40718). It seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a myristyl group, a farnesyl group, a geranyl-geranyl group, a GPI-anchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for the modified IL5 polypeptide. Another possibility is use of the C3d fragment of complement factor C3 or C3 itself (cf. Dempsey et al., 1996, Science 271, 348-350 and Lou & Kohler, 1998, Nature Biotechnology 16, 458-462).

An alternative embodiment of the invention which also results in the preferred presentation of multiple (e.g. at least 2) copies of the important epitopic regions of IL5 to the immune system is the covalent or non-covalent coupling of IL5, subsequence or variants thereof to certain carrier molecules. For instance, polymers can be used, e.g. carbohydrates such as dextran, cf. e.g. Lees A et al., 1994, Vaccine 12: 1160-1166; Lees A et al., 1990, J. Immunol. 145: 3594-3600, but also mannose and mannan are useful alternatives. Integral membrane proteins from e.g. E. coli and other bacteria are also useful conjugation partners. The traditional carrier molecules such as keyhole limpet hemocyanin (KLH), tetanus toxoid, diphtheria toxoid, and bovine serum albumin (BSA) are also preferred and useful conjugation partners.

Certain areas of native IL5 are believed to be superiorly suited for performing modifications. It is predicted that modifications in at least one of loops 1-3 or in the amino acid residues C-terminal to helix D (said loops and said helix D corresponding to those shown in FIG. 3 for human and murine IL5) will be most likely to produce the desired constructs and vaccination results. Considerations underlying these chosen areas are a) preservation of known and predicted B-cell epitopes, b) preservation of tertiary and quaternary structures etc, cf. also the discussion in the preamble to the examples. At any rate, as discussed above, it is fairly easy to screen a set of modified IL5 molecules which have all been subjected to introduction of a T-cell epitope in different locations.

Since the most preferred embodiments of the present invention involves down-regulation of human IL5, it is consequently preferred that the IL5 polypeptide discussed above is a human IL5 polypeptide. In this embodiment, it is especially preferred that the human IL5 polypeptide has been modified by substituting at least one amino acid sequence in SEQ ID NO: 1 with at least one amino acid sequence of equal or different length and containing a foreign $T_H$ epitope, wherein substituted amino acid residues are selected from the group consisting of residues 87-90, residues 32-43, residues 59-64, residues 86-91, and residues 110-113. The rationale behind such constructs is discussed in detail in the examples.

Formulation of IL5 and Modified IL5 Polypeptides

When effecting presentation of the IL5 polypeptide or the modified IL5 polypeptide to an animal's immune system by means of administration thereof to the animal, the formulation of the polypeptide follows the principles generally acknowledged in the art.

Preparation of vaccines which contain peptide sequences as active ingredients is generally well understood in the art, as exemplified by U.S. Pat. Nos. 4,608,251; 4,601,903; 4,599, 231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, buccal, sublinqual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10-95% of active ingredient, preferably 25-70%. For oral formulations, cholera toxin is an interesting formulation partner (and also a possible conjugation partner).

The polypeptides may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 2,000 µg (even though higher amounts in the 1-mg range are contemplated), such as in the range from about 0.5 µg to 1,000 µg, preferably in the range from 1 µg to 500 µg and especially in the range from about 10 µg to 100 µg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein.

It is especially preferred to use an adjuvant which can be demonstrated to facilitate breaking of the autotolerance to autoantigens; in fact, this is essential in cases where unmodified IL5 is used as the active ingredient in the autovaccine. Non-limiting examples of suitable adjuvants are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; γ-inulin; and an encapsulating adjuvant. In general it should be noted that the disclosures above which relate to compounds and agents useful as first, second and third moieties in the analogues also refer mutatis mutandis to their use in the adjuvant of a vaccine of the invention.

The application of adjuvants include use of agents such as aluminium hydroxide or phosphate (alum), commonly used as 0.05 to 0.1 percent solution in buffered saline, admixture with synthetic polymers of sugars (e.g. CARBOPOL®) used as 0.25 percent solution, aggregation of the protein in the vaccine by heat treatment with temperatures ranging between 70° to 101° C. for 30 second to 2 minute periods respectively and also aggregation by means of cross-inking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and γ-inulin, but also Freund's complete and incomplete adjuvants as well as quillaja saponins such as QuilA and QS21 are interesting as is RIBI. Further possibilities are monophosphoryl lipid A (MPL), the above mentioned C3 and C3d, and muramyl dipeptide (MDP).

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from Quillaja saponaria, cholesterol, and phospholipid. When admixed with the immunogenic protein, the resulting particulate formulation is what is known as an ISCOM particle where the saponin constitutes 60-70% w/w, the cholesterol and phospholipid 10-15% w/w, and the protein 10-15% w/w. Details relating to composition and use of immunostimulating complexes can e.g. be found in the above-mentioned text-books dealing with adjuvants, but also Morein B et al., 1995, Clin. Immunother. 3: 461-475 as well as Barr IG and Mitchell GF, 1996, Immunol. and Cell Biol. 74: 8-25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fcγ receptors on monocytes/macrophages. Especially conjugates between antigen and anti-FcγRI have been demonstrated to enhance immunogenicity for the purposes of vaccination.

Other possibilities involve the use of the targeting and immune modulating substances (i.a. cytokines) mentioned above as candidates for the first and second moieties in the modified versions of IL5. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer such as; and latex such as latex beads.

Yet another interesting way of modulating an immune response is to include the IL5 immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15 1998, Seascape Resort, Aptos, Califormia".

It is expected that the vaccine should be administered at least once a year, such as at least 1, 2, 3, 4, 5, 6, and 12 times a year. More specifically, 1-12 times per year is expected, such as 1, 2, 3, 4, 5, 6, 7, 8, 9, 10, 11, or 12 times a year to an individual in need thereof. It has previously been shown that the memory immunity induced by the use of the preferred autovaccines according to the invention is not permanent, and therefor the immune system needs to be periodically challenged with the analogues.

Due to genetic variation, different individuals may react with immune responses of varying strength to the same polypeptide. Therefore, the vaccine according to the invention may comprise several different polypeptides in order to increase the immune response, cf. also the discussion above concerning the choice of foreign T-cell epitope introductions. The vaccine may comprise two or more polypeptides, where all of the polypeptides are as defined above.

The vaccine may consequently comprise 3-20 different modified or unmodified polypeptides, such as 3-10 different polypeptides. However, normally the number of polypeptides will be sought kept to a minimum such as 1 or 2 polypeptides.

Nucleic Acid Vaccination

As an alternative to classic administration of a peptide-based vaccine, the technology of nucleic acid vaccination (also known as "nucleic acid immunisation", "genetic immunisation", and "gene immunisation") offers a number of attractive features.

First, in contrast to the traditional vaccine approach, nucleic acid vaccination does not require resource consuming large-scale production of the immunogenic agent (e.g. in the form of industrial scale fermentation of microorganisms producing modified IL5). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum posttranslational processing of the expression product is expected to occur; this is especially important in the case of autovaccination, since, as mentioned above, a significant fraction of the original IL5 B-cell epitopes should be preserved in the modified molecule, and since B-cell epitopes in principle can be constituted by parts of any (bio)molecule (e.g. carbohydrate, lipid, protein etc.). Therefore, native glycosylation and lipidation patterns of the immunogen may very well be of importance for the overall immunogenicity and this is expected to be ensured by having the host producing the immunogen.

Hence, a preferred embodiment of the invention comprises effecting presentation of modified IL5 to the immune system by introducing nucleic acid(s) encoding the modified IL5 into the animal's cells and thereby obtaining in vivo expression by the cells of the nucleic acid(s) introduced.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, DNA encapsulated in a polymer, e.g. in PLGA (cf. the microencapsulation technology described in WO 98/31398) or in chitin or chitosan, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply mutatis mutandis to their use in nucleic acid vaccination technology.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can suitably be administered intraveneously and intraarterially. Furthermore, it is well-known in the art that nucleic acid vaccines can be administered by use of a so-called gene gun, and hence also this and equivalent modes of administration are regarded as part of the present invention. Finally, also the use of a VLN in the administration of nucleic acids has been reported to yield good results, and therefore this particular mode of administration is particularly preferred.

Furthermore, the nucleic acid(s) used as an immunization agent can contain regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitope is produced as a fusion partner to the immunomodulator. Alternatively, two distinct nucleotide fragments can be used, but this is less preferred because of the advantage of ensured co-expression when having both coding regions included in the same molecule.

Accordingly, the invention also relates to a composition for inducing production of antibodies against IL5, the composition comprising a nucleic acid fragment or a vector of the invention (cf. the discussion of vectors below), and a pharmaceutically and immunologically acceptable vehicle and/or carrier and/or adjuvant as discussed above.

Under normal circumstances, the IL5 variant-encoding nucleic acid is introduced in the form of a vector wherein expression is under control of a viral promoter. For more detailed discussions of vectors and DNA fragments according to the invention, cf. the discussion below. Also, detailed disclosures reating to the formulation and use of nucleic acid vaccines are vailable, cf. Donnelly J J et al, 1997, Annu. Rev. Immunol. 15: 617-648 and Donnelly J J et al., 1997, Life Sciences 60: 163-172. Both of these references are incorporated by reference herein.

Live Vaccines

A third alternative for effecting presentation of modified IL5 to the immune system is the use of live vaccine technology. In live vaccination, presentation to the immune system is effected by administering, to the animal, a non-pathogenic microorganism which has been transformed with a nucleic acid fragment encoding a modified IL5 or with a vector incorporating such a nucleic acid fragment. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae, Shigella*, etc. Reviews dealing with preparation of state-of-the-art live vaccines can e.g. be found in Saliou P, 1995, Rev. Prat. 45: 1492-1496 and Walker PD, 1992, Vaccine 10: 977-990, both incorporated by reference herein. For details about the nucleic acid fragments and vectors used in such live vaccines, cf. the discussion below.

As an alternative to bacterial live vaccines, the nucleic acid fragment of the invention discussed below can be incorporated in a non-virulent viral vaccine vector such as a vaccinia strain or any other suitable pox virus.

Normally, the non-pathogenic microorganism or virus is administered only once to the animal, but in certain cases it may be necessary to administer the microorganism more than once in a lifetime in order to maintain protective immunity. It is even contemplated that immunization schemes as those detailed above for polypeptide vaccination will be useful when using live or virus vaccines.

Alternatively, live or virus vaccination is combined with previous or subsequent polypeptide and/or nucleic acid vaccination. For instance, it is possible to effect primary immunization with a live or virus vaccine followed by subsequent booster immunizations using the polypeptide or nucleic acid approach.

The microorganism or virus can be transformed with nucleic acid(s) containing regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitopes are produced as fusion partners to the immunomodulator. Alternatively, two distinct nucleotide fragments can be used as transforming agents. Of course, having the $1^{st}$ and/or $2^{nd}$ and/or $3^{rd}$ moieties in the same reading frame can provide as an expression product, an analogue of the invention, and such an embodiment is especially preferred according to the present invention.

Use of the Method of the Invention in Disease Treatment

As will be appreciated from the discussions above, the provision of the method of the invention allows for control of diseases characterized by eosinophilia. In this context, asthma is the key target for the inventive method but also other chronic allergic conditions such as multiple allergy and allergic rhinitis are feasible targets for treatment/amelioration. Hence, an important embodiment of the method of the invention for down-regulating IL5 activity comprises treating and/or preventing and/or ameliorating asthma or other chronic allergic conditions characterized by eosinophilia, the method comprising down-regulating IL5 activity according to the method of the invention to such an extent that the number of eosinophil cells is significantly reduced.

In the present context such a significant reduction in eosinophil cell numbers is at least 20% compared to the eosinophil number prior to treatment, but higher percentages are contemplated, such as at least 30%, at least 40%, at least 50%, at least 60%, at least 70%, at least 80% and even at least 90%. The reduction may be systemic or, more often, locally in e.g. the lungs.

Eosinophil cell numbers are determined by methods known in the art, typically using microscopy of a suitable sample (such as a BAL fluid) and counting the number of eosinophil cells manually under microscope. Alternatively, eosinophil numbers can be counted using flow cytometric methods or any other convenient method of cytometry capable of distinguishing eosinophils.

Peptides, Polypeptides, and Compositions of the Invention

As will be apparent from the above, the present invention is based on the concept of immunising individuals against the IL5 antigen in order to indirectly obtain a reduction in eosinophil cell numbers. The preferred way of obtaining such an immunization is to use modified versions of IL5, thereby providing molecules which have not previously been disclosed in the art.

It is believed that the modified IL5 molecules discussed herein are inventive in their own right, and therefore an important part of the invention pertains to an IL5 analogue which is derived from an animal IL5 wherein is introduced a modification which has as a result that immunization of the animal with the analogue induces production of antibodies cross-reacting with the unmodified IL5 polypeptide. Preferably, the nature of the modification conforms with the types of modifications described above when discussing various embodiments of the method of the invention when using modified IL5. Hence, any disclosure presented herein pertaining to modified IL5 molecules are relevant for the purpose of describing the IL5 analogues of the invention, and any such disclosures apply *mutatis mutandis* to the description of these analogues.

It should be noted that preferred modified IL5 molecules comprise modifications which results in a polypeptide having a sequence identity of at least 70% with IL5 or with a subsequence thereof of at least 10 amino acids in length. Higher sequence identities are preferred, e.g. at least 75% or even at least 80% or 85%. The sequence identity for proteins and nucleic acids can be calculated as $(N_{ref}-N_{dif})\cdot 100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8).

The invention also pertains to compositions useful in exercising the method of the invention. Hence, the invention also relates to an immunogenic composition comprising an immunogenically effective amount of an IL5 polypeptide which is a self-protein in an animal, said IL5 polypeptide being formulated together with an immunologically acceptable adjuvant so as to break the animal's autotolerance towards the IL5 polypeptide, the composition further comprising a pharmaceutically and immunologically acceptable vehicle and/or carrier. In other words, this part of the invention pertains to the formulations of naturally occurring IL5 polypeptides which have been described in connection with embodiments of the method of the invention.

The invention also relates to an immunogenic composition comprising an immunologically effective amount of an IL5 analogue defined above, said composition further comprising a pharmaceutically and immunologically acceptable diluent and/or vehicle and/or carrier and/or excipient and optionally an adjuvant. In other words, this part of the invention concerns formulations of modified IL5, essentially as described hereinabove. The choice of adjuvants, carriers, and vehicles is accordingly in line with what has been discussed above when referring to formulation of modified and unmodified IL5 for use in the inventive method for the down-regulation of IL5.

The polypeptides are prepared according to methods well-known in the art. Longer polypeptides are normally prepared by means of recombinant gene technology including introduction of a nucleic acid sequence encoding the IL5 analogue into a suitable vector, transformation of a suitable host cell with the vector, expression of the nucleic acid sequence, recovery of the expression product from the host cells or their culture supernatant, and subsequent purification and optional further modification, e.g. refolding or derivatization.

Shorter peptides are preferably prepared by means of the well-known techniques of solid- or liquid-phase peptide synthesis. However, recent advances in this technology has rendered possible the production of full-length polypeptides and proteins by these means, and therefore it is also within the scope of the present invention to prepare the long constructs by synthetic means.

Nucleic Acid Fragments and Vectors of the Invention

It will be appreciated from the above disclosure that modified IL5 polypeptides can be prepared by means of recombinant gene technology but also by means of chemical synthesis or semisynthesis; the latter two options are especially relevant when the modification consists in coupling to protein carriers (such as KLH, diphtheria toxoid, tetanus toxoid, and BSA) and non-proteinaceous molecules such as carbohydrate polymers and of course also when the modification comprises addition of side chains or side groups to an IL5 polypeptide-derived peptide chain.

For the purpose of recombinant gene technology, and of course also for the purpose of nucleic acid immunization, nucleic acid fragments encoding modified IL5 are important chemical products. Hence, an important part of the invention pertains to a nucleic acid fragment which encodes an IL5 analogue, i.e. an IL5 derived polypeptide which either comprises the natural IL5 sequence to which has been added or inserted a fusion partner or, preferably an IL5 derived polypeptide wherein has been introduced a foreign T-cell epitope by means of insertion and/or addition, preferably by means of substitution and/or deletion. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of a vector of the invention comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or integration into the membrane of the polypeptide fragment, the nucleic acid fragment of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is not incapable of being integrated in the host cell genome; typically, naked DNA or non-integrating viral vectors are used, the choices of which are well-known to the person skilled in the art.

The vectors of the invention are used to transform host cells to produce the modified IL5 polypeptide of the invention. Such transformed cells, which are also part of the invention, can be cultured cells or cell lines used for propagation of the nucleic acid fragments and vectors of the invention, or used for recombinant production of the modified IL5 polypeptides of the invention. Alternatively, the transformed cells can be suitable live vaccine strains wherein the nucleic acid fragment (one single or multiple copies) have been inserted so as to effect secretion or integration into the bacterial membrane or cell-wall of the modified IL5.

Preferred transformed cells of the invention are microorganisms such as bacteria (such as the species *Escherichia* [e.g. *E. coli], Bacillus* [e.g. *Bacillus subtilis], Salmonella*, or *Mycobacterium* [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Most preferred are cells derived from a human being, cf. the discussion of cell lines and vectors below. Recent results have shown great promise in the use of a commercially available *Drosophila melanogaster* cell line (the Schneider 2 ($S_2$)cell line and vector system available from Invitrogen) for the recombinant production of IL5 analogues of the invention, and therefore this expression system is particularly preferred.

For the purposes of cloning and/or optimized expression it is preferred that the transformed cell is capable of replicating the nucleic acid fragment of the invention. Cells expressing the nucleic fragment are preferred useful embodiments of the invention; they can be used for small-scale or large-scale preparation of the modified IL5 or, in the case of non-pathogenic bacteria, as vaccine constituents in a live vaccine.

When producing the modified IL5 of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the modified IL5. Preferably, this stable cell line secretes or carries the IL5 analogue of the invention, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in prokaryotic recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used, and here the promoter should be capable of driving expression. *Saccharomyces cerevisiase*, or common baker's yeast is the most commonly used among eukaryotic microorganisms, although a number of other strains are commonly available. For expression in *Saccharomyces*, the plasmid $YR_p7$, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 31 of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), and MDCK cell lines. In the present invention, an especially preferred cell line is $S_2$ available from Invitrogen, PO Box 2312, 9704 CH Groningen, The Netherlands.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with N the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Identification of Useful IL5 Analogues

It will be clear to the skilled person that not all variants or modifications of native IL5 will have the ability to elicit antibodies in an animal which are cross-reactive with the native form. It is, however, not difficult to set up an effective standard screen for modified IL5 molecules which fulfill the minimum requirements for immunological reactivity discussed herein. Hence, another part of the invention concerns a method for the identification of a modified IL5 polypeptide which is capable of inducing antibodies against unmodified IL5 in an animal species where the unmodified IL5 polypeptide is a self-protein, the method comprising preparing, by means of peptide synthesis or by molecular biological means, a set of mutually distinct modified IL5 polypeptides wherein amino acids have been added to, inserted in, deleted from, or substituted into the amino acid sequence of an IL5 polypeptide of the animal species thereby giving rise to amino acid sequences in the set which comprise T-cell epitopes which are and foreign to the animal species, or preparing a set of nucleic acid fragments encoding the set of mutually distinct modified IL5 polypeptides, testing members of the set for their ability to induce production of antibodies by the animal species against the unmodified IL5, and identifying and optionally isolating the member(s) of the set which significantly induces antibody production against unmodified IL5 in the animal species, or identifying and optionally isolating the polypeptide expression products encoded by members of the set of nucleic acid fragments which significantly induces antibody production against unmodified IL5 polypeptide in the animal species.

In this context, the "set of mutually distinct modified IL5 polypeptides" is a collection of non-identical modified IL5 polypeptides which have e.g. been selected on the basis of the criteria discussed above (e.g. in combination with studies of circular dichroism, NMR spectra, and/or X-ray diffraction patterns). The set may consist of only a few members but it is contemplated that the set may contain several hundred members. Likewise, the set of nucleic acid fragments is a collection of non-identical nucleic acid fragments, each encoding a modified IL5 polypeptide selected in the same manner.

The test of members of the set can ultimately be performed in vivo, but a number of in vitro tests can be applied which narrow down the number of modified molecules which will serve the purpose of the invention.

Since the goal of introducing the foreign T-cell epitopes is to support the B-cell response by T-cell help, a prerequisite is that T-cell proliferation is induced by the modified IL5. T-cell proliferation can be tested by standardized proliferation assays in vitro. In short, a sample enriched for T-cells is obtained from a subject and subsequently kept in culture. The cultured T-cells are contacted with APCs of the subject which have previously taken up the modified molecule and processed it to present its T-cell epitopes. The proliferation of T-cells is monitored and compared to a suitable control (e.g. T-cells in culture contacted with APCs which have processed intact, native IL5). Alternatively, proliferation can be measured by determining the concentration of relevant cytokines released by the T-cells in response to their recognition of foreign T-cells.

Having rendered highly probable that at least one modified IL5 of the set is capable of inducing antibody production against IL5, it is possible to prepare an immunogenic composition comprising at least one modified IL5 polypeptide which is capable of inducing antibodies against unmodified IL5 in an animal species where the unmodified IL5 polypeptide is a self-protein, the method comprising admixing the member(s) of the set which significantly induces production of antibodies in the animal species which are reactive with IL5 with a pharmaceutically and immunologically acceptable carrier and/or vehicle and/or diluent and/or excipient, optionally in combination with at least one pharmaceutically and immunologically acceptable adjuvant.

Likewise, it is also possible to prepare an immunogenic composition which as an immunogen contains a nucleic acid fragment encoding a immunogenic IL5 analogue, cf. the discussion of nucleic acid vaccination above.

The above aspects of the invention are conveniently carried out by initially preparing a number of mutually distinct nucleic acid sequences or vectors of the invention, inserting these into appropriate expression vectors, transforming suitable host cells with the vectors, and expressing the nucleic acid sequences of the invention. These steps can be followed by isolation of the expression products. It is preferred that the nucleic acid sequences and/or vectors are prepared by methods comprising exercise of a molecular amplification technique such as PCR or by means of nucleic acid synthesis.

PREAMBLE TO EXAMPLES

Vaccine Design

The exemplary candidates for an IL5 autovaccine are constructed according to the AutoVac™ concept (described in detail in WO 95/05849) by substitution with known promiscuous T cell epitopes into the human IL5 wild type protein. The substitutions are peptide substitutions, where the inserted peptide may be of the same or different length than the deleted peptide in the wild-type sequence.

For initial proof of concept by in vivo testing and screening, it was decided to prepare the constructs in the murine IL5 sequence. By way of example, the tetanus toxoid epitopes P2 (SEQ ID NO: 23) and P30 (SEQ ID NO: 24) are used as substituting peptides, but any other suitable peptide containing or constituting a promiscuous $T_H$ epitope could, according to the present invention, be used.

It should be emphasized that the size of the molecule (115 res.) compared to the size of the substitutions (15 or 21 residues for P2 and P30, respectively) strongly limits the possible sites of structural non-destructive inserts. As the disulfide bridges are important, but not imperative, for the dimerization, some variants are made in pairs +/− elimination of the cysteines.

In the construction of the candidate molecules, two basic parameters have been considered. First, it is attempted to conserve a maximum fraction of the three-dimensional structure of the wild type hIL5, thereby conserving the native B-cell epitope repertoire. This is supported by Dickason et al., (1994) who demonstrated that IL5 B-cell epitopes known to be neutralising are conformational. Conservation of the tertiary structure is sought achieved by introducing the modifications at structurally "neutral" sites, such as loops or separate segments. The fact that the N-terminal helix "A" together with the helices "B" and "C" are able to fold into a quaternary structure with a second molecule, indicates that these 3 helices constitute a stable folding-scaffold.

Second, the biological activity in relation to the vaccine concept has been considered. In general, an inactive construct is preferable with a view to reducing putative toxic effects of the molecules and in general for evaluating the immune response. On the other hand, the optimum neutralising antibodies should theoretically exhibit specificity for the part of IL5 that interacts with the IL5R. This is most likely achieved by immunising with an active variant. Finally, it is not impossible that the biological effect of IL5 on the immune system might act as an enhancer on the immune response, thus improving the overall effect. Based on Applicant's previous experiences with other molecules, however, the majority of "theoretically possible active" constructs is expected to have low or no activity.

Therefore, all variants suggested are potentially active but can, if desirable, with relative ease be rendered inactive by hindering the formation of the active dimer or by alterations in the areas of the "A"-and "D"-helices that are involved in the receptor binding/activation.

In summary, the above considerations of structure conservation and biological activity defines the target areas as any one of loops 1-3 as well as the C-terminal flexible area.

Loop 3 is selected as the primary target area since it is structurally separated from the assumed tri-helical folding scaffold. As it is furthermore possible to produce a biologically active monomer, by elongation of loop 3 (Dickason, 1996), this area holds the possibilities for generating all types of variants: monomer/dimer and active/inactivated.

"Loop 1" is a second area containing a non-helical stretch of a suitable length for substitutions. Variants from this region would theoretically be active only if capable of dimerising, but since the length of the wild-type loop makes it rather flexible it is reasonable to expect a correct folding of the protein after substitution.

Variants containing substitutions in the "loop 2" area will also only be active as dimers. The area that can be substituted is short compared to the inserts and has a central position in the assumed folding scaffold, two characteristics of loop 2 which might be of hindrance to the correct folding of the protein after substitution. On the other hand, loop 2 is situated opposite to the area interacting with the IL5R, resulting in an expected optimum presentation of the wild-type neutralising epitopes if the modified protein is correctly folded.

Finally, inserts in the C-terminal flexible region following "helix D" are proposed. From a protein structure point of view this concept appears fairly safe, but it is likely that modifications in this region will affect both dimerization and biological activity (if the modified protein is dimerized) since the C-terminal is located in the area of both receptor binding and in the dimer interface.

The amino acid sequence of 10 variants initially constructed according to the above considerations are set forth as SEQ ID NOs: 2-11 and 13-22. Further variants constructed at a later stage are set forth in SEQ ID NOs: 27-59 (including both DNA nucleic acid sequences and amino acid sequences).

It should be noted, that all inserts except from the ones according to Example 2 are prepared so as to include flanking amino acid residues that are conserved from hIL5 to mIL5 in order to promote the process of successful transfer of positive constructs from mice to man.

In the following examples, positions for substitution are indexed according to the murine amino acid residue sequence numbers; the corresponding human positions are given in parentheses.

Example 1

Variants with P2 Substituting Positions in Loop 3 while Preserving Cys84(86)

The P2 epitope (SEQ ID NO: 23) is substituted into loop 3 while avoiding elimination of Cys84 (86). These variants (SEQ ID NOs: 2 and 28 (human), where amino acids 87-90 or 88-91 are substituted and 13 and 46 (murine) where amino acids 85-88 pr 86-89 are substituted) are potentially active as both monomers (due to the elongation of loop 3) and as dimers. SEQ ID Nos: 28 and 46 are also denoted hIL5.1 and mIL5.1, respectively.

Example 2

Variants with P2 Substituting Positions in Loop 1 while Preserving Cys42(44)

The P2 epitope (SEQ ID NO: 23) is substituted into loop 1 while avoiding elimination of Cys42(44). These variants (SEQ ID NOs: 3 and 36 (human) where amino acids 32-43 or 33-43 are substituted and 14 and 56 (murine) where amino acids 30-41 or 31-41 are substituted) are potentially active as diners only. SEQ ID Nos: 36 and 56 are also denoted hIL5.5 and mIL5.5, respectively.

Example 3

Variants with P2 Substituting Positions in Loop 2

The P2 epitope (SEQ ID NO: 23) is substituted into loop 2. These variants (SEQ ID NOs: 4 and 34 (human) where amino acids 59-64 are substituted and 15 and 50 (murine) where amino acids 57-62 are substituted) are potentially active as dimers only. SEQ ID Nos: 34 and 50 are also denoted hIL5.4 and mIL5.4, respectively.

Example 4

Variants with P2 Substituting Positions in Loop 3 while Eliminating Cys84(86)

The P2 epitope (SEQ ID NO: 23) is substituted into loop 3 while eliminating Cys84 (86). These variants (SEQ ID NOs: 5 and 38 (human) where amino acids 86-91 are substituted and 16 and 54 (murine) where amino acids 84-89 are substituted) are in principle similar to the variants of type #1 (SEQ ID NOs: 2 and 28 and 13 and 46), but the generation of monomer products has been facilitated by inhibiting the formation of disulfide bridging and adjusting the length of loop 3. SEQ ID Nos: 38 and 54 are also denoted hIL5.6 and mIL5.6, respectively.

EXAMPLE 5

Variants with P2 Substituting Positions 108-111 (110-113) in the C-terminus

The P2 epitope (SEQ ID NO: 23) is substituted into the C-terminal area succeeding helix D. These variants (SEQ ID NOs: 6 and 17) are potentially active as a dimer only.

Example 6

Variants with P30 Substituting Positions in Loop 3 while Preserving Cys84(86)

The P30 epitope (SEQ ID NO: 24) is substituted into loop 3 avoiding elimination of Cys84(86). These variants (SEQ ID NOs: 7 and 40 (human) where amino acids 88-91 or 87-90 are substituted and 18 and 58 (murine) where amino acids 85-88 or 86-89 are substituted) are potentially active both as monomers (due to the elongation of loop 3) and as dimers. SEQ ID Nos: 40 and 58 are also denoted hIL5.7 and mIL5.7, respectively.

Example 7

Variants with P30 Substituting Positions in Loop 1 while Preserving Cys42(44)

The P30 epitope (SEQ ID NO: 24) is substituted into loop 1, avoiding elimination of Cys42(44). These variants (SEQ ID NOs: 8 and 30 (human) where amino acids 32-43 are substituted and 19 and 48 (murine) where amino acids 30-41 are substituted) are potentially active as dimers only. SEQ ID Nos: 30 and 48 are also denoted hIL5.2 and mIL5.2, respectively.

Example 8

Variants with P30 Substituting Positions in Loop 2

The P30 epitope (SEQ ID NO: 24) is substituted into loop 2. These variants (SEQ ID NOs: 9 and 20 where amino acids 59-64 and 57-62 are substituted, respectively) are potentially active as dimers only.

Example 9

Variants with P30 Substituting Positions in the C Terminus

The P30 epitope (SEQ ID NO: 24) is substituted into the C-terminal area succeeding helix D. These variants (SEQ ID NOs: 10 and 21 where amino acids 110-113 and 108-111 are substituted, respectively) are potentially active as dimers only.

Example 10

Variants with P2 Substituting Positions 84-89 (86-91) and P30 Substituting Positions 110-113

The P2 epitope (SEQ ID NO: 23) is substituted into loop 3 eliminating Cys84(86) and the P30 epitope (SEQ ID NO: 24) is substituted into the C-terminal area succeeding helix-D. These variants (SEQ ID NOs: 11 and 22) are together with variants of type #12 the only ones containing both epitopes and are potentially active monomers.

Example 11

Variants with P30 Substituting Positions in Loop 3 while Eliminating Cys84(86)

The P2 epitope (SEQ ID NO: 24) is substituted into loop 3 while eliminating Cys84 (86). These variants (SEQ ID NOs: 42 (human) where amino acids 86-91 are substituted and 58 (murine) where amino acids 84-89 are substituted) are in principle similar to the variants of type #6, but the generation of monomer products has been facilitated by inhibiting the formation of disulfide bridging and adjusting the length of loop 3. SEQ ID Nos: 42 and 58 are also denoted hIL5.12 and mIL5.12, respectively.

Example 12

Variants with P2 and P30 Substituting Positions in Loop 3

The P2 (SEQ ID NO: 23) and P30 (SEQ ID NO: 24) epitopes are substituted into loop 3 while preserving Cys84 (86). These variants (SEQ ID NOs: 44 and 60 where amino acids 88-91 and 86-89 are substituted, respectively) contain both epitopes and are potentially active monomers. SEQ ID NOs: 44 and 60 are also denoted hIL5.13 and mIL5.13, respectively.

Example 13

Choise of Expression System

Recombinant IL5 has been expressed in a number of different expression systems including yeast, insect cells and CHO cells (Tavernier et al., 1989).

According to the present invention, one suitable expression system is *E. coli*, based on previous studies reporting the use of this host for production hIL5 (Proudfoot et al., 1990, Graber et al., 1993). The recombinant protein is expressed as inclusion bodies that are converted into the biologically active dimer upon purification and re-folding (e.g. using the generally applicable refolding methods disclosed in U.S. Pat. No. 5,739,281). The speed and simplicity of *E. coli* expression allows immediate initiation of the production of protein when the genetic constructs are ready, thus facilitating rapid generation of material to establish an in vivo proof of the IL5 autovaccine concept.

If for some reason the feasibility is found to be to low (e.g. low yield following re-folding, instability of the products or improved pharmacokinetical parameters related to glycosylation etc), production in yeast could be considered in a further development of the autovaccine.

Recently, promising results have been obtained using the *Drosophila melanogaster* expression system using $S_2$ cells (available from Invitrogen) and at present this system is the preferred embodiment for expression of the IL5 analogues of the invention.

IL5 variant protein was produced from S2 *drosophila* cells stably expressing the IL5 constructs. Several different transfection methods were tested, and both $Ca_2PO_4$ and Lipofectin were chosen. Two different subclones of S2 cells were used and transfected with $Ca_2PO_4$ and Lipofectin, respectively. The two clones were obtained from ATCC and Lars Søndergaard of the University of Copenhagen, respectively. Using both methods suitable stable lines were selected expressing mIL5 and mIL5.1 proteins in the 2-10 mg/L range.

Materials & Methods

S2 cells were grown and maintained in Schneider's medium (Sigma) containing 5-10% fetal calf serum (FCS), 0.1% pluronic F68 (Sigma)$_1$ penicillin/streptomycin (Life Technologies) grown in shake flasks at 25° C. and 120 rpm.

Lipofectin transfections were performed in 250 ml or 1 l shake flasks. S2 cells were split to $2.5-3\times10^6$/ml into 50 ml Excell 420 (JRH Biosciences) without antibiotics, and grown overnight in a 250 ml shake flask. The next morning the Lipofectin reagents were prepared: tube 1) 300-1200 μg plasmid DNA containing the gene of interest, plus 15-60 μg pCoHYGRO hygromycin selection plasmid (20:1 ratio of plasmids) in 15-45 ml serum and supplement-free medium; tube 2) 1 ml Lipofectin in 5 ml serum and supplement-free medium. After 1 hour at room temperature, tubes 1 and 2 were mixed and rested for 15 minutes at room temperature before gently adding to S2 cells. After growing cells overnight new media was added containing full supplements plus 150-300 μg/ml Hygromycin.

Transient and stable lines were induced with either 500 M copper sulfate or 10 μM cadmium chloride for 48-72 hours in serum-free Ex-cell 420 medium (JRH Biosciences).

Results 33 stable lines were generated by $Ca_2PO_4$ and 23 by Lipofectin. The expression yields varied from non-detectable up to 11 mg/L. The following table summarizes a few of the lines used for protein production.

Expression result summary from best mIL5 S2 cell transfections.

| Plasmid | Construct | S2 cells | Transfection Method | Yield |
|---|---|---|---|---|
| p612 | IL5/His15/mIL5wt | ATCC | $Ca_2PO_4$ | 3.5 mg/L |
| p767 | Bip/His15/mIL5wt | LS | Lipofectin | 11 mg/L |
| p613 | IL5/His15/mIL5.1 | ATCC | $Ca_2PO_4$ | 2.6 mg/L |
| p768 | Bip/His15/mIL5.1 | ATCC | $Ca_2PO_4$ | 0* |
| p614 | IL5/His15/mIL5.5 | LS | Lipofectin | 0* |

*Expression plasmid contained sequence mutations.

Hence, S2 cells can be transfected by either calcium phosphate precipitation or Lipofectin. Due to the difference in expression level between plasmids p612 and p767, it seems that the Bip signal peptide is a more efficient leader sequence than the endogenous mIL5 leader in S2 cells.

Example 14

Screening and Selection of the Modified Molecules

Following expression, the recombinant protein is purified and characterised. The characterisation of the autovaccine candidates will include analytical chromatography, iso-electric focussing (IEF), SDS-PAGE, amino acid composition analysis, N-terminal sequence analysis, mass spectrometry, low angle laser light scattering, standard spectroscopy, and Circular Dichroism to an extent that precisely document the relevant parameters defining the intended protein product.

The His tagged proteins have been purified using a two-step procedure until recently. However, the yield and purity were not as high as expected after the final chelate-step. A new one-step purification procedure has been implied with 3 major advantages achieved: higher yield, higher through-put and higher purity of the final product. Cleavage conditions for removal of the histag have also been established.

The Two-Step IL5 Purification Procedure:

Expression of the protein is induced by addition of metal ions to the media. These metal-ions have to be removed before application of the protein to the chelate column. Thus, a total of 20 mM EDTA is added to complex the metal-ions and the supernatant is then passed over a SP-sepharose column to capture the protein. After washing to remove unbound protein, bound protein is eluted by a step-gradient of NaCl. This step serves two purposes: a concentrating step reducing the volume by a factor of 30, and buffer-exchange.

Relevant fractions (as determined by SDS-PAGE) are pooled and further purified on the metal chelate column.

The protein is applied to a $Ni^{2+}$-charged chelate column and unbound protein washed off. Bound protein is then eluted using an Imidazole gradient. All fractions, flow-through and EDTAwashes of the column, are then checked by both SDS-PAGE and dot-blot.

Relevant fractions (as determined by SDS-PAGE and dot-blot) are pooled and dialyzed twice against 10× volume of PBS, pH adjusted to 6.9.

After filtration, the dialyzed material is concentrated until a suitable concentration is achieved (preferably 1 mg/ml). Finally, the protein is aliqouted and stored at −20° C.

The following specific protocol has been applied:

1) The received supernatant is centrifuged at 2500×g for 15 min (if infection has occurred, it needs centrifugation at 22000×g for 30 min. The supernatant is then filtered using a 0.45 μm filter followed by a 0.22 μm filter (sometimes it is necessary to filter through a 5 μm filter first).

The supernatant is then mixed 1:1 with buffer A (see step 2) containing 40 mM EDTA, resulting in a final buffer composition of 0.2 M $NaH_2PO_4$, 10% glycerol, 20 mM EDTA, pH 6.0

2) The filtered supernatant is subsequently applied to a SP-Sepharose column equilibrated in buffer A. A total of 1-2 L (depending on protein concentration, the above holds for 1-10 mg IL5/L) can be applied to an 80 ml column. Flow during application: 1-2 ml/min (usually over night), the flow-through is collected and saved for later analysis. Following application, the column is washed with 2-3 column volumes (CV) of A-buffer until a stable baseline is achieved. Bound protein is eluted using a step gradient: 0-100-500-1000 mM NaCl, fractions of 10 ml are collected, flow is 10 ml/min. Purification is performed at 5° C.

The column is cleaned with 2 CV 1 M NaOH, flow 5 ml/min after each run and re-equilibrated in buffer A.

Buffer A: 0.2 M NaH$_2$PO$_4$, 10% glycerol, pH 6.0
Buffer B: 0.2 M NaH$_2$PO$_4$, 1 M NaCl, 40 mM Imidazole, 10% glycerol, pH 6.0
The same procedure is used for both wt and variants.
All fractions, starting material and flow-through are tested in dot-blot and SDS-PAGE. The fractions containing IL5 are pooled and further purified using a chelate-column.

The One-Step IL5 Purification Procedure:

The supernatant is applied directly to a 70-ml chelate-column charged with ZnCl$_2$. After removal of the unbound material by washing, bound protein (IL5 and contaminants) is eluted by applying a gradient of Imidazole. This method takes full advantage of the His tag giving a one-step purification procedure with a high degree of purity of the final product (>95%). Relevant fractions (as determined by SDS-PAGE and dot-blot) are pooled and dialyzed twice against 10× volume of PBS, pH adjusted to 6.9 and concentration of NaCl adjusted to 400 mM.

After filtration, the dialyzed material is concentrated until a suitable concentration is achieved (preferably 1 mg/ml). Finally, the protein is aliqouted and stored at −20° C. A specific protocol follows the following steps 1) The supernatant is filtered through a 0.45 μm filter to remove impurities and diluted 1:1 with buffer A.
   A 70-ml Fast Flow chelate column is rinsed with 5 CV water and then charged with 10 CV 10 mM ZnCl$_2$, pH 7. After equilibration with 5 CV A-buffer, the sample is applied using the pump (flow 10 ml/min). The flow-through is collected and saved for later analysis. Bound protein is eluted using an Imidazole-gradient going from 0 to 250 mM Imidazole over 30 CV. Finally, the column is stripped by 5 CV of buffer C.
   Fractions of 10 ml are collected.
   Buffers:
   A: 20 mM NaH$_2$PO$_4$, 0.5 M NaCl, 10% glycerol, pH 7.
   B: 20 nM NaH$_2$PO$_4$, 0.5 M NaCl, 10% glycerol, pH 7, 0.25 M imidazole
   C: 20 mM NaH$_2$PO$_4$, 0.5 M NaCl, 0.1 M EDTA pH 7.0.
   All fractions, flow-through and starting material is tested in SDS-PAGE.
2) The purest fractions (as determined by SDS-PAGE) containing IL5 are pooled (50 μl are saved for later analysis) and dialyzed twice against 10× volume of PBS, pH adjusted to 6.9. at 6° C., MWCO 12-14 kDa. The dialysate is filtered through a 0.22 μm filter (50 μl is saved for later analysis) and A$_{280}$ is measured using dialysis-buffer (filtered through 0.45 μm) as reference. The volume before and after dialysis is measured and samples showing the dialysis/concentrating step are saved for later analysis by SDS-PAGE (after step 3).
3) NaCl is added to the dialyzed protein until a total concentration of 400 mM and it is then concentrated using either an Amicon apparatus (for volumes larger than 50 ml) or Vivaspin concentrating device (for 10-50 ml). In both cases, the membrane is saturated with 10 ml PBS-buffer buffer before the sample is applied. The sample should be concentrated until a concentration of preferably 1 mg/ml is achieved (as measured by A$_{280}$). The dialyzed, concentrated sample is filtered through a 0.22 μm filter and marked with an E-nr. The A$_{280}$ is measured using the flow-through as reference.
   All samples from the dialysis and concentrating step are analyzed by SDS-PAGE and Coomassie-stained. The purified protein is stored frozen in aliquots and a sheet describing the sample is filed in the "IL5-protein"-folder.

The above-described procedure gives a protein with a purity of approximately 90-95%, still containing the His Tag. When sequenced, both IL5 wt and variant IL5.1 gave the expected N-terminal sequences including the His Tag.

The purification procedure referred to above has been implemented in the following specific setup:

1) The pooled fractions from the SP-sepharose column are filtered through a 0.45 μm filter to remove impurities.
   A 5-ml HiTrap chelate column(use only dedicated columns) is rinsed with 15 ml water (using a syringe) and then charged with ml 0.1 M NiSO$_4$ and washed with 15 ml water. The column is connected to the Akta-system and equilibrated with 2-3 CV A-buffer. The sample is applied using either the loop or pump—depending on the volume (flow 4 ml/min), the flow-through is collected and saved for later analysis. Bound protein is eluted using an Imidazole-gradient going from 0 to 500 μM Imidazole over 20 CV. Fractions of 5 ml are collected. Finally, the column is stripped using 5 CV of buffer B2.

| Buffer A: | 0.2 M NaH$_2$PO$_4$, 0.5 M NaCl, 10% glycerol, pH 5.0 |
|---|---|
| Buffer B1: | 0.2 M NaH$_2$PO$_4$, 0.5 M NaCl, 0.5 M Imidazole, 10% glycerol, pH 5.0 |
| Buffer B2: | 50 mM Na-acetate, 0.5 M NaCl, 0.1 M EDTA, 10% glycerol, pH 4.5 |

All fractions, flow-through and starting material are tested in dot-blot, all relevant fractions are tested in SDS-PAGE.

2) The purest fractions (as determined by SDS-PAGE) containing IL5 are pooled (save 50 μl for later analysis) and dialyzed twice against 10× volume of PBS, pH adjusted to 6.9. at 6° C., MWCO 12-14 kDa. The dialysate is filtered through a 0.22 μm filter (save 50 μl for later analysis) and A$_{280}$ is measured using filtered dialysis-buffer as reference. The volume before and after dialysis is measured and samples showing the dialysis/concentrating step are saved for later analysis by SDS-PAGE (after step 3).
3) After addition of extra NaCl up to a final concentration of 400 mM, the dialyzed protein is concentrated using either an Amicon apparatus (for volumes larger than 50 ml) or Vivaspin concentrating device (for 10-50 ml). In both cases, the membrane is saturated with 10 ml PBS buffer before the sample is applied. The sample should be concentrated until a concentration of preferably 1 mg/ml is achieved (as measured by A$_{280}$). The A$_{280}$ is measured using the flow-through as reference. The dialyzed, concentrated sample is filtered through a 0.22 μm filter and marked with an E-nr.

All samples from the dialysis and concentrating step are analyzed by SDS-PAGE and Coomassie-stained. The purified protein is stored frozen in aliquots.

Other purification procedures that have been evaluated are:

Zn$^{2+}$-chelate purification: Elution of the protein using an increasing Imidazole gradient has proved very efficient as the wt-protein binds strongly to the column. The *Drosophila* supernatant can be directly applied and after washing, the IL5 wt can be eluted by Imidazole. The column is charged with 10 CV 10 mM ZnCl$_2$, and washed with water. The pH of the binding and elution buffers has to be above 6.5 as otherwise the ZnCl$_2$ will precipitate.

Con A affinity chromatography is under investigation. The possibility of using the glycosylation present on IL5 as an affinity-tag and elute by application of a monosaccharide-analog would be interesting since it could be applied to the non-His tagged constructs as well.

Removal of Histag:

Removal of the 15 aa His tag (SEQ ID NO: 25) has been performed according to suppliers (Unizyme) instructions:

The purified and dialyzed/concentrated His tagged IL5 is de-His tagged by the sequential addition of two enzymes, DAP1 and Glutamine cyclotransferase. DAP1 removes two amino acids from the free N-terminus while the QCT The enzyme needs to be activated first:

9 µl HT-DAPL (10 U/ml) is mixed with 9 µl 20 mM cysteamine-HCl. After 5 min incubation at room temperature, a total 108 μl HP-GCT (100 U/ml) and 54 μl TAGZyme buffer is added. This must be used within 15 min.

This portion will digest 1 mg of His tagged protein.

The His tagged protein is mixed with 150 μl activated enzyme and incubated at 37° C. for 120 min. Samples are withdrawn for SDS-PAGE analysis (10 μl) after 0, 10, 30, 60 and 120 min. The samples are put on ice to stop the digestion.

Buffers:

1. TAGZyme buffer: 20 mM $NaPO_4$ buffer, pH 7.5; 150 mM NaCl
2. 20 mM Cysteamine-HCl The digested protein (as determined from SDS-PAGE analysis or N-terminal sequencing) is applied to a 1-ml Ni-chelate column equilibrated in PBS. Everything is collected.

The flow-through from the application is saved for later analysis. The column is eluted by addition of 3 CV PBS, fractions of 0.5 ml are collected. The column is cleaned by washing with 2 CV 0.5 M1 m Imidazole, and fractions are saved for analysis.

All fractions are tested in SDS-PAGE, and fractions containing IL5 are pooled and $A_{280}$ is measured using PBS as reference. Finally, the protein is concentrated using a Vivaspin concentrating device until a concentration of 1 mg/ml is achieved.

Removal of His tag has been performed in small-scale experiments (0,1-1 mg) and has not been up-scaled. It should be noted that removal of the tag requires an unblocked and non-modified N-terminus.

The His tagged protein is incubated with two enzymes, a dipeptidyl amino peptidase which removes two amino acids at a time and a glutamic acid cyclotransferase which catalyze the conversion of a glutamic acid into a pyro-glutamic acid. This conversion blocks further degradation by the dipeptidyl amino peptidase. The digestion mixture is then passed through a chelate column which should retain the enzymes (which are His tagged), contaminating proteins binding to the column and non-degraded or partially degraded protein. The de-tagged protein passes the column and is collected in the flow-through. After a second digestion with an enzyme that removes the pyro-glutamic acid, the protein is again passed over a chelate-column to remove the second enzyme. It is expected that the protein needs to be concentrated again at this final stage.

General Observations:

The pI of UniHis-IL5 wt is 9.5 and the optimum pH-value for the protein seems to be 6.5-7.0 (has not been investigated thouroughly). A NaCl-concentration of 400 mM seems to stabilize the protein during concentration.

Example 15

In Vitro Screening

The primary in vitro screening will be in the form of an enzyme-linked immunosorbent assay (ELISA): A competitive ELISA towards wild-type IL5 provides an estimate of the presence of relevant B-cell epitopes in the modified IL5 constructs before introduction thereof into animals.

A conventional ELISA assay can be used to measure titres of auto-antibodies in the serum of vaccinated animals. Antibodies (both mono-specific and monoclonal) towards the human as well as towards the murine IL5 are commercially available from R&D Systems, 614 McKinley Place NE, Minneapolis, Minn. 55413, USA.

The biological activity of the product and/or the neutralising capacity of induced auto-antibodies can be tested in an IL5 bioassay. Previously reported examples of such bioassays are: Assessment of IL5 induced proliferation of TF1 cells (for human IL5) and assessment of IL5 induced proliferation of BCL1 cells or B13 B cells (for murine IL5) (Callard & Gearing 1994, Dickason et al., 1994).

The effect on airway responsiveness of the autovaccine can also be tested in an in vitro assay wherein the trachea from vaccinated mice are removed and placed on a hook in an organ bath. The tension of the trachea after histamine challenge is measured (van Oosterhout et al., 1995).

Consequently, in order to be able to determine the biological activity of recombinant mIL5 (and mIL5 AutoVac) protein samples, a cellular bioactivity assay for murine IL5 is being established. The assay is based on the ability of the B cell lymphoma line BCL1 to proliferate in response to mIL5 added to the culture medium. Two different BCL1 clones were obtained from ATCC, BCL1 clone 5B1b (ATCC CRL-1669) and BCL1 clone CW13.20.3B3 (ATCC TIB-197).

In a typical BCL1 proliferation experiment, the cells are plated in complete RPMI medium supplemented with fetal calf serum (FCS) in microtiter plates and incubated with dilution series of murine IL5. Proliferation of the BCL1 cells is measured by incorporation of tritiated thymidine. Several optimization experiments have been performed using dilution series of purchased recombinant mIL5 (R&D Systems) for stimulation. The variable parameters include: incubation intervals, $^3$Hthymidine pulsing intervals, numbers of cells plated per well, fetal calf serum (FCS) concentrations and concentrations of added mIL5. Dose-dependent proliferation of the BCL1 cells with a maximal proliferation of about 3 times the background (BCL1 cells with no mIL5 added) has been obtained. The BCL1 assay has been used to determine the biological α-tivity of the following samples expressed from *Drosophila* S2 cells and purified as described above: HIS-mIL5wt material (E1320), HIS-mIL5 wt material (E1422), HIS-mIL5.1 material (E1396) and an "S2-background-preparation" (E0016). The proliferation in response to one HIS-mIL5 wt (E1320) preparation was significantly higher than the proliferation in response to the "S2-background-preparation", whereas the mIL5.1 variant and one wild type preparation (E1422) were determined as biologically inactive.

Ongoing work includes inhibition of the BCL1 proliferation with anti-mIL5, and the anti-mIL5 monoclonal antibody TRFK5 is used for optimization studies. This is done in order to use this assay to determine the ability of anti-mIL5 antisera from immunised mice to inhibit the biological activity of mIL5.

Example 16

In Vivo Models

For measuring the in vivo effect of the autovaccine, well-known animal models for asthma exists. Normally, the animal is sensitised with a compound (allergen/antigen) and after challenge with the aerosolised compound, bronchoconstriction (airway conduction) is measured using a body plethysmograph.

The eosinophil cell counts in the BAL fluid are also determined.

Several of the studies investigating the effect of anti-IL5 mAb's have been successfully performed in mice. Against use of the murine model speaks the fact the IL5 acts as a B-cell growth factor, rendering possible interference with the murine antibody response. However, as shown in a study using IL5 knock-out mice, the T-cell dependent antibody response against ovalbumin as well as cytotoxic T-cell development appeared normal (Kopf et al., 1996). As the mouse is also the most practical and economical model in comparison to guinea pigs or monkeys, the ovalbumin sensitised Bal/c mice model of asthma/airway hypersensitivity as used by Hamelman et al. 1997) will be used.

If, however, the effect of IL5 on B-cells in the murine model turns out to be a problem, the use of other suitable animal models known in the art will be applied.

Example 17

Preparation of DNA Constructs Encoding Murine IL5 and Variants Thereof.

Construction of Variants in pcDNA3.1+:

Insertion of P2 and P30 epitopes into wildtype mIL5 was done by SOE-PCR with overlapping primers containing the epitope sequences. Wildtype mIL5 gene including leader sequence (SEQ ID NO: 63), cloned into pcDNA3.1+ with consensus Kozak sequence (obtaining plasmid p815), was used as template for the PCR reactions. The resulting fragments were digested with NheI and NotI, purified and cloned into p815 was used as template for the PCR.

Cloning of Variants into pMT Drosophila Vector with BiP Leader and UNI-His tag:

Wildtype mIL5 was cloned into the pMT Drosophila expression vector series (Invitrogen) by generating a PCR fragment with mIL5 specific primers containing appropriate restriction sites and, in addition, containing sequences encoding a Drosophila Kozak like sequence followed by the Drosophila BiP leader sequence followed by a sequence encoding a UNI-HIS tag (SEQ ID NO: 25) fused to the 5' end of the sequence encoding mature mIL5. Wildtype mIL5 cDNa sequence was used as template. The resulting fragment was digested with EcoRI and NotI and was subsequently cloned into the pMT/V5-HisA vector (Invitrogen). The resulting plasmid (p818) was used for cloning of epitope containing variants into pMT. These were cloned by digesting the variants made in pcDNA3.1+ with SacI and NotI and cloning the resulting fragments into p818.

Cloning of Variants Into pAC5:

Wildtype and variants of mIL5 were cloned into the pAC5 constitutive Drosophila expression vector by digestion of variants in pMT with EcoRI and NotI and cloning the resulting fragments into the pAC5.1/V5-HisA vector (Invitrogen).

Example 18

Preparation of DNA Constructs Encoding Human IL5 and Variants Thereof.

Five lines of plasmids are contemplated containing unmodified IL5 and all or some of the nine IL5 variants. The lines include: 1) human IL5 for DNA vaccination in the pCI vector suited for expression in human cells, 2) human IL5 with the BiP leader sequence and a 15 aa His tag (SEQ ID NO: 25, obtained from UNIZYME in Horsholm, Denmark. The tag is termed "UNI" or "UNI-His tag" herein) in the pMT/V5/HIS vector for inducible expression in *Drosophila,* 3) as in 2 but without the His tag, 4) as in 3 but with murine IL5 and 5) human IL5 with the DAP1 leader sequence and the 15 aa HIS tag in the vector pVL1393 for expression in the baculo-virus system.

Plasmids for DNA-vaccination in the pCI vector:

| Name | ref # | Strain # | Epitope |
|---|---|---|---|
| hIL5 (pCI) | p888 | MR#1237 | none |
| hIL5.1 (pCI) | p889 | MR#1238 | P2, Loop 3 |
| hIL5.2 (pCI) | p890 | MR#1239 | P30, Loop 1 |
| hIL5.3 (pCI) | p891 | MR#1240 | P30, Loop 2 |
| hIL5.4 (pCI) | p892 | MR#1241 | P2, Loop 2 |
| hIL5.5 (pCI) | p893 | MR#1242 | P2, Loop 1 |
| hIL5.6 (pCI) | p894 | MR#1243 | P2, Loop 3 |
| hIL5.7 (pCI) | p895 | MR#1244 | P30, Loop 3 |
| hIL5.12 (pCI) | p896 | MR#1245 | P30, Loop 3 |
| hIL5.13 (pCI) | p897 | MR#1246 | P2 and P30, Loop 3 |

Plasmids for human IL5 expression in *Drosophila* with the UNIHIS tag and BiP leader sequence in pMT/V5/HIS

| Name | Ref # | Strain # | Epitope |
|---|---|---|---|
| hIL5m-UNI-BiP (pMT/V5-HisA) | p899 | MR#1247 | none |
| hIL5.1m-UNI-BiP (pMT/V5-HisA) | p900 | MR#1248 | P2, Loop 3 |
| hIL5.2m-UNI-BiP (pMT/V5-HisA) | p901 | MR#1249 | P30, Loop 1 |
| hIL5.3m-UNI-BiP (pMT/V5-HisA) | p929 | MR#1277 | P30, Loop 2 |
| hIL5.4m-UNI-BiP (pMT/V5-HisA) | p902 | MR#1250 | P2, Loop 2 |
| hIL5.5m-UNI-BiP (pMT/V5-HisA) | p903 | MR#1251 | P2, Loop 1 |
| hIL5.6m-UNI-BiP (pMT/V5-HisA) | p904 | MR#1252 | P2, Loop 3 |
| hIL5.7m-UNI-BiP (pMT/V5-HisA) | p905 | MR#1253 | P30, Loop 3 |
| hIL5.12m-UNI-BiP (pMT/V5-HisA) | p906 | MR#1254 | P30, Loop 3 |
| hIL5.13m-UNI-BiP (pMT/V5-HisA) | p907 | MR#1255 | P2 and P30, Loop 3 |

Plasmids for human IL5 expression in *Drosophila* with the BiP leader sequence, but without the UNI-HIS tag in pMT/V5/HIS:

| Name | Ref # | Strain # | Epitope |
|---|---|---|---|
| hIL5m-BiP (pMT/V5-HisA) | p908 | MR#1256 | none |
| hIL5.1m-BiP (pMT/V5-HisA) | p909 | MR#1257 | P2, Loop 3 |
| hIL5.2m-BiP (pMT/V5-HisA) | p921 | MR#1269 | P30, Loop 1 |
| hIL5.3m-BiP (pMT/V5-HisA) | p922 | MR#1270 | P30, Loop 2 |
| hIL5.4m-BiP (pMT/V5-HisA) | p923 | MR#1271 | P2, Loop 2 |
| hIL5.5m-BiP (pMT/V5-HisA) | p924 | MR#1272 | P2, Loop 1 |
| hIL5.6m-BiP (pMT/V5-HisA) | p925 | MR#1273 | P2, Loop 3 |

-continued

| Name | Ref # | Strain # | Epitope |
| --- | --- | --- | --- |
| hIL5.7m-BiP (pMT/V5-HisA) | p926 | MR#1274 | P30, Loop 3 |
| hIL5.12m-BiP (pMT/V5-HisA) | p927 | MR#1275 | P30, Loop 3 |
| hIL5.13m-BiP (pMT/V5-HisA) | p928 | MR#1276 | P2 and P30, Loop 3 |

Plasmids for murine IL5 expression in *Drosophila* with the BiP leader sequence, but without the 15 aa His tag in pMT/V5/HIS:

| Name | ref # | Strain # | Epitope |
| --- | --- | --- | --- |
| mIL5m-BiP (pMT/V5-HisA) | p918 | MR#1266 | none |
| mIL5.1m-BiP (pMT/V5-HisA) | p919 | MR#1267 | P2, Loop 3 |
| mIL5.2m-BiP (pMT/V5-HisA) | p920 | MR#1268 | P30, Loop 1 |

Plasmids for human IL-5 expression in the baculo-virus system with the UNI-HIS tag and DAP1 leader sequence pVL1393 in pVL1393:

| Name | Ref # | Strain # | Epitope |
| --- | --- | --- | --- |
| hIL5m-UNI-DAP1 (pVL1393) | p916 | MR#1264 | none |
| hIL5.1m-UNI-DAP1 (pVL1393) | p917 | MR#1265 | P2, Loop 3 |

Example 19

DNA Immunization Studies

Generation of Vectors Encoding mIL5Wt, mIL5.1 and mIL5.5 with Kozak Sequences for DNA Vaccination Experiments:

DNA fragments encoding mIL5wt, mIL5.1 and mIL5.5 including the natural leader sequence (SEQ ID NO: 63) were inserted into pcDNA3.1 thus yielding new plasmids p521, 522, and p523. In order to enhance expression of cDNA in mammalian cells, Kozak concensus sequences were inserted upstream of the coding sequences using PCR technology. PCR reactions were performed using p521, p522 and p523 as templates and a forward primer encoding the Kozak sequence immediately upstream of the mIL5 leader start codon. Purified PCR products were cloned into pcDNA3.1+ vector using restriction endonucleases BamHI and NotI. The resulting plasmids p815, p816 and p817, respectively, were verified by DNA sequencing. All other plasmids used for DNA vaccination experiments were constructed using the p521 plasmid as starting material.

In Vitro Translation of DNA Vaccination Plasmids Using Promega Kit:

A commercial kit using rabbit reticulocyte extract to generate in vitro translated protein product plasmid DNA, has previously been successfully used in our lab to monitor protein expression from pcDNA plasmid encoding e.g ovalbumin cDNA. Murine IL5 DNA vaccination plasmids were added to the kit reagents according to the standard procedure. However, several attempts to detect expressed mIL5 material on autoradiograms failed whereas positive controls worked. Results from COS cell transfections and DNA vaccination shows that the gene products are expressed, so we did not investigate these technical problems further.

Transient Transfection of COS Cells with DNA Vaccination Plasmids to Determine Expression Levels:

In order to monitor the transfection/expression efficiency of the plasmids used for DNA vaccination experiments, a transient transfection assay using COS cells was established. COS cells were trypsinized and plated in DMEM medium supplemented with 10% FCS in T25 culture flasks. The cells were transfected at day 2 using the Dotap kit (Roche Diagnostics) and harvested at day 5. Culture supernatant, whole cell lysate and membrane enriched preparations were tested in Western blotting to detect anti-mIL5 reactive expression product. The anti-mIL5 reactive product in the cell preparations consistently migrated as 2-3 separate bands of 21-28 kD in SDS-PAGE, whereas the MW of the mIL5 monomer used as standard (expressed in bacculovirus, R&D Systems) is only 15-18 kD. Using non-denaturating circumstances, the 21-28 kD substances form diners so we believe the material is mIL5, possibly in several differently glycosylated forms. DNA vaccination results (see below) clearly support this conclusion.

DNA Vaccination of Mice Using Murine IL5 AutoVac Constructs:

A DNA vaccination study was performed in order to investigate whether antibody responses specific for murine IL5 can be induced by immunising mice with naked plasmid DNA encoding 8 different murine IL5 mutants. Since IL5 previously has been reported to play a role in B cell differentiation, it is essential to demonstrate that anti-mIL5 autoantibodies can be generated in mice and B cell tolerance to mIL5 can be broken.

The general setup of the DNA vaccination experiments use either C3H/Hen mice (H-$2^k$) or Balb/cA mice (H-2d), 6-8 weeks old divided into groups of 5 mice each. At days 0, 14, 28, 42, 62 and 76 the mice were anaestesized using hypnorm/dormicum s.c. and injected with expression plasmids encoding ovalbumin (control), mIL5wt (wild type), or the mIL5 variants to be tested. The DNA material was prepared using endofree GigaPrep kits (Qiagen) and dissolved at 1 µg/ml in 0.15 M NaCl or 0.15 M NaCl containing 0.1% bupivacaine. 100 µl material was injected i.d. in each mouse at the lower back distributed at two injection sites. Prebleeds were obtained at day minus 2, and the test bleedings were obtained at weeks 3, 5, 8 and 11. Sera were isolated by centrifugation and stored at −20° C. until testing in ELISA for reactivity against purified ovalbumin and mIL5 proteins.

Figure 4:
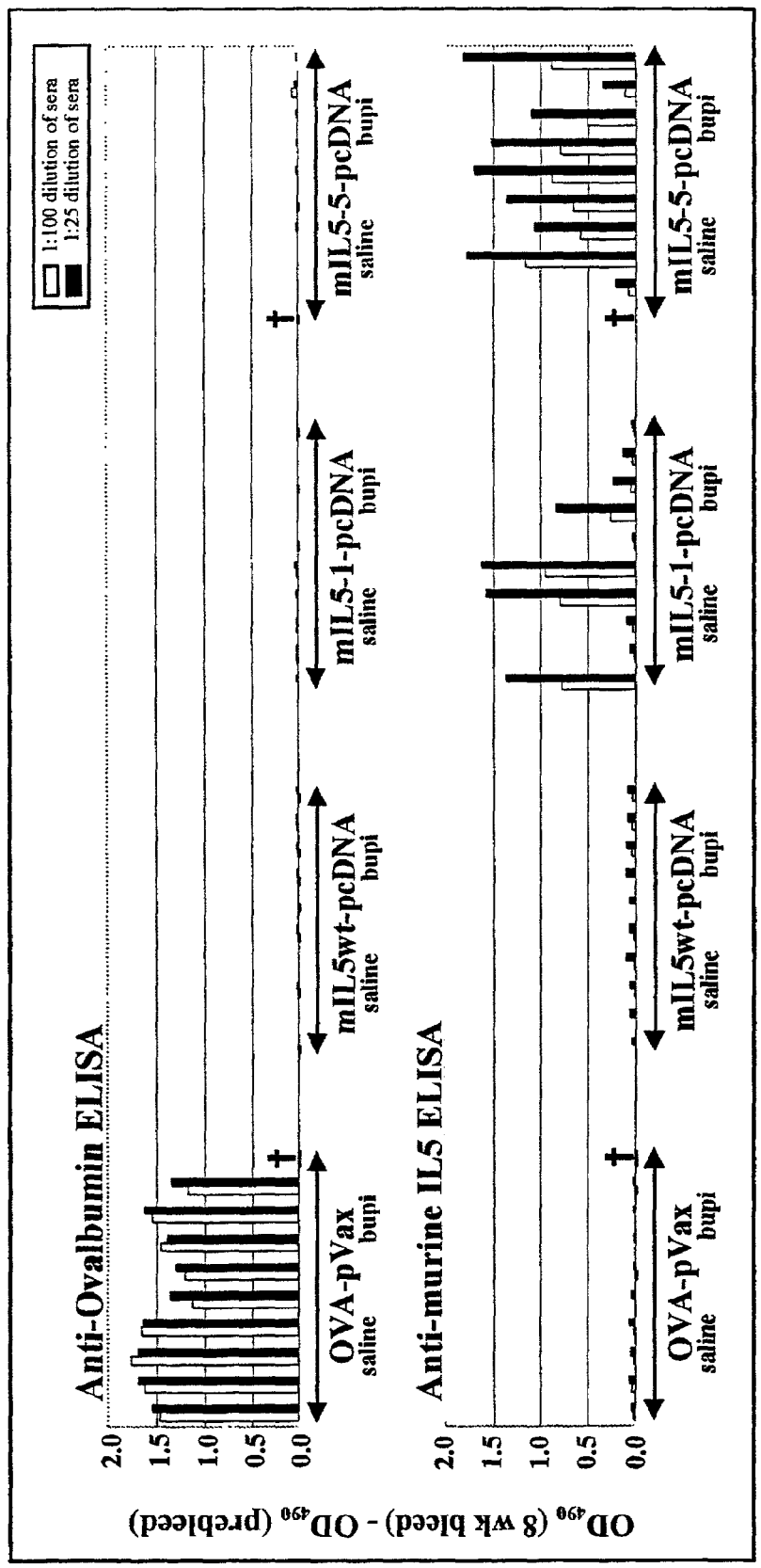
Figure 5:
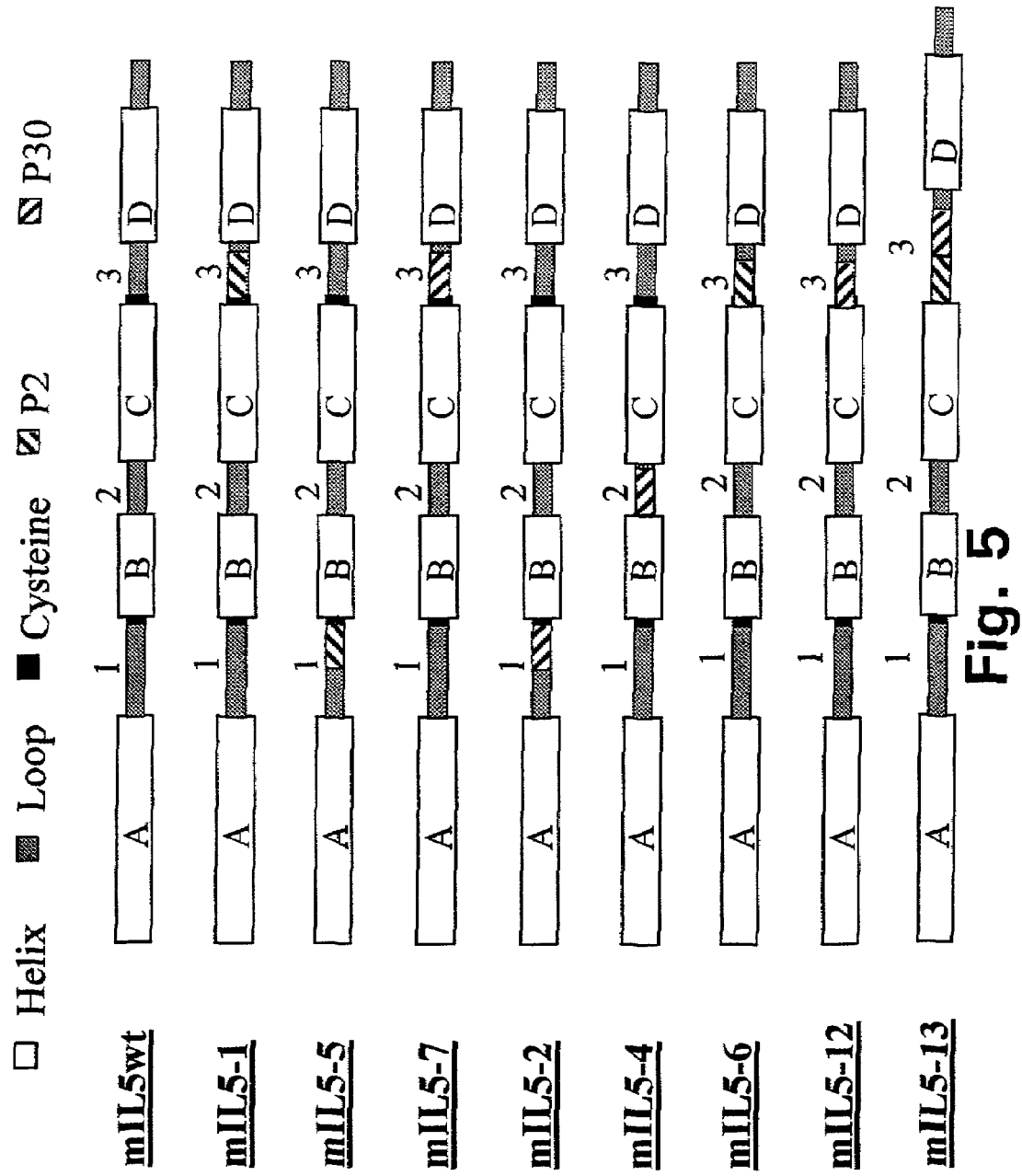

A Typical result of a DNA vaccination experiment is shown in FIG. 4. According to the general setup described above, 40 Balb/cA mice were immunized with ovalbumin control plasmid, mIL5wt encoding plasmid or plasmids encoding the mIL5 AutoVac variants mIL5.1 or mIL5.5. In this experiment, 9 out of 9 mice immunized with ovalbumin encoding plasmid developed anti-ovalbumin antibodies, whereas no anti-ovalbumin response was induced in mice receiving the mIL5 wild type or mIL5 variant encoding DNA. Injection of mIL5wt encoding plasmid did not give raise to an anti-mIL5 response, whereas the B cell tolerance to mIL5 was broken in 4 out of 10 mice immunized with mIL5.1 plasmid and 7 out of 9 mice immunized with mIL5.5 encoding plasmid DNA.

The main result of the whole series of DNA vaccination experiments is summarized in the table below. The number of responders within an immunisation group differs between the different mIL5 AutoVac constructs and is dependent on the mouse strain. Clearly, the mIL5.2 AutoVac construct is superior to the other variants, being able to induce anti-mIL5 antibody responses in both mouse strains with a penetrance of 100%. This plasmid (p820) also gave the highest expression levels in the COS transfection assay.

Another example to emphasize is the apparent MHC restriction seen when using mIL5.4 encoding plasmid DNA as immunogen. Whereas only 1/10 C3H/Hen mice responds to the DNA vaccine, 9 out of 10 Balb/cA mice are responders. The opposite phenomenon (although not quite as pronounced) is seen with the mIL5.6 construct. The mIL5.2 DNA vaccine, however, seem to be promiscuously immunogenic.

(which was not absorbed by the antisera) was next visualised using layers of biotinylated TRFK4 and subsequently horse radish peroxidase labeled streptavidin. Not all the anti-mIL5 positive antisera induced by DNA vaccination could inhibit the interaction between soluble mIL5 and TRFK4 or TRFK5. The antiserum with the highest TRFK4/5 inhibiting capability was from C3H/Hen mice immunized with mIL5.2 encoding DNA. It has not been tested whether the observed differences in inhibition is a direct measure of titer differences or it is connected to the fine specificity of the different antisera. Most likely, it is a combination of these two factors.

|  | OVAwt-pVax | mIL5wt-pcDNA | mIL5.1-pcDNA | mIL5.2-pcDNA | mIL5.4-pcDNA |
| --- | --- | --- | --- | --- | --- |
| Balb/cA | 28/28 | 0/28 | 4/10 | 9/10 | 9/10 |
| C3H/Hen | 29/29 | 0/30 | 3/10 | 10/10 | 1/10 |

|  | mIL5.5-pcDNA | mIL5.6-pcDNA | mIL5.7-pcDNA | mIL5.12-pcDNA | mIL5.13-pcDNA |
| --- | --- | --- | --- | --- | --- |
| Balb/cA | 7/9 | 0/10 | 2/10 | 0/10 | 0/10* |
| C3H/Hen | 5/10 | 6/10 | 2/10 | 2/10 | 2/10* |

Summary of the result of DNA vaccination of 280 mice. 6 mice died during the experiment for reasons not connected to the effects of the DNA vaccination. The number of responders (with high or intermediate anti-mIL5 titers) is shown in relation to the total number of mice within each immunization group. *) bleedings obtained at day 55. All the other bleedings were obtained at day 77.

Another feature to mention is the tendency of mIL5 variants with the foreign T helper epitope inserted in mIL5 loop1 to be stronger DNA vaccination immunogens than variants with the T helper epitope inserted in loop 3. This could be due to the relatively high expression levels. The only loop 2 variant tested, mIL5,4-pcDNA is only a strong immunogen in the Balb/cA strain, as mentioned above.

Further Characterization of the Antibody Responses Induced by DNA Vaccination:

ELISA experiments were set up in order to determine whether antibodies specific for the inserted T helper epitope could be detected in anti-mIL5 positive mice. For each immunisation group, sera from anti-mIL5 positive mice were pooled and tested for reactivity against P2 or P30 peptides which had been immobilised in AquaBind microtiter plates. Antisera induced by DNA vaccination against mIL5.2 in both mouse strains clearly contained reactivity against the inserted P30, whereas none of the other antisera were reactive with P2 or P30. This is probably connected to the higher antibody titers and penetrance that is generally observed with the mIL5.2 DNA vaccination construct. It should be mentioned that using this ELISA setup we were able to detect anti-P2 reactivity in antisera induced against mIL5.1.

The positive anti-mIL5 antiserum pools from the DNA vaccinated mice were also tested in a competive ELISA for their ability to inhibit the interaction between soluble native murine IL5 and monoclonal antibodies TRFK4 or TRFK5, which are both neutralizing antibodies. Dilution series of anti-mIL5 antiserum pools were preincubated with soluble native mIL5 and the sample was added to ELISA plates coated with catching antibody TRFK5. Bound murine IL5

Animal Model of Eosinophilia in mIL5 Autovac DNA Immunized Mice:

40 DNA vaccinated mice were chosen for testing in an animal model of eosinophilia: 10 Balb/cA mice immunized with mIL5 wt DNA, 10 Balb/cA mice immunized with mIL5.2 DNA, 10 C3H/Hen mice immunized with mIL5 wt DNA and 10 C3H/Hen mice immunized with mIL5.2 DNA. A sensitization/challenging regimen with ovalbumin to induce eosinophilia was given to in each of these mice. The mice were sensitized with subcutaneous injections of 50 μg ovalbumin (OVA) in 0.9% saline mixed 1:1 with Adjuphos once per week for three weeks. Four days after the last OVA sensitization the mice were challenged intranasally with 12.5 μg OVA in 0.9% saline every other day for a total of 3 challenges. Bronchoalveolar lavage fluid (BALF) was collected one day after the last sensitization by cannulating the tracheae and washing the airway lumina with 1 ml PBS.

Approximately 30,000-60,000 BALF cells were spun unto slides at 1,500 rpm for 20 minutes. The slides were dried overnight and stained for 2.5 minutes with May-Grunwald stain (Sigma), washed for 4 minutes in tris buffered saline, stained for 20-30 minutes with Geimsa stain (1:20 with dd$H_2O$; Sigma) and briefly rinsed with dd$H_2O$. Stained slides were dried overnight and cell types were identified using light microscopy. Approximately 100-200 cells were counted per slide and 3 slides were counted per mouse. The eosinophil counts were expressed as the number of eosinophils per 100 cells counted. In mIL5.2 DNA vaccinated C3H/Hen mice, the induction of lung eosinophilia was significantly down-regulated compared to the wild type mIL5 wt DNA vaccinated group (mIL5.2 DNA: 14.6±8.9 eosinophils per 100 cells; mIL5 wt DNA: 51.1±9.9 eosinophils per 100 cells). However, in the Balb/cA strain, there was no significant difference in eosinophil counts between the immunization groups (mIL5.2 DNA: 23.3±6.8 eosinophils per 100 cells; mIL5 wt DNA: 27.7±9.3 eosinophils per 100 cells). A possible explanation is that Balb/cA mice are only weakly susceptible to the model. This is supported by anti-ovalbumin ELISA data showing that one week before the BALF collection the anti-ovalbumin titers in serum from the Balb/cA mice were lower than in serum from C3H/Hen. The Balb/cJ substrain is reported to be susceptible to the OVA sensitization/challenge model.

Example 20

Protein Vaccination Study

Balb/c J mice were immunized with murine IL5 (mIL5) protein and subjected to an ovalbumin intranasal model that induces eosinophils in the lungs of treated mice. Both the UniHis-mIL5 and the UniHis-mIL5.1 proteins induced antibodies that cross-react with mIL-5 made in sf9 cells from R&D Systems. The eosinophilia model induced high numbers of eosinophils in the OVA control group and the UniHis-mIL5.1 groups, while the numbers of eosinophils were reduced in both the PBS group and the UniHis-mIL5 group. This result led us to believe that the groups may have been mixed.

Materials & Methods

| | |
|---|---|
| UniHis-mIL-5 | E1320 & E01397 |
| UniHis-mIL-5.1 | E01337 & E01396 |

Immunizations:

6-8 week old female Balb/c J (M&B) mice were immunized with either 1) nothing, 2) PBS, 3) UniHis-mILS, or 4) UniHis-mIL-5.1 in Complete Freund's Ajuvant (CFA; Sigma) and boosted 3 times at three week intervals with antigen in Incomplete Freund's Adjuvant (IFA; Sigma). Sera was collected and tested in an ELISA 10 days after each boost.

ELISAs:

Anti-UniHis-mIL5 ELISA:

Sera were obtained at days 32 (bleed 1) and 54 (bleed 2) after 2 and 3 immunizations, respectively. Polystyrene microtiter plates (Maxisorp, Nunc) were coated with purified HIS-mILSwt (0.1 µg/well, E1320). The reactivities of diluted sera added to the wells were visualised using a goat anti-mouse secondary antibody. OD490 readings of control sera from mice immunized with PBS in Freunds adjuvans were subtracted from the OD490 readings of the test samples.

Anti-mIL5 ELISA:

Sera were obtained at day 75 (bleed 3). Polystyrene microtiter plates (Maxisorp, Nunc) were coated with purchased mIL5 (0.1 µg/well, R&D cat. no. 405-ML). The reactivities of 1:1000 diluted sera added to the wells were visualised using a goat anti-mouse secondary antibody. The reactivity of TRFK5 (2 µg/ml) was visualised using a rabbit anti-rat secondary antibody.

Competitive ELISA:

Dilutions of antisera were preincubated with soluble IL5 for 1 hour and added to polystyrene microtiter plates (Maxisorp, Nunc) which were coated with catching antibody TRFK5. Bound mL5 was visualised using biotinylated TRFK4 and a HRP la-belled goat anti-mouse secondary antibody.

Anti-P2 ELISA:

Pools of antisera from HIS-mIL5wt, HIS-mIL5.1 or PBS immunised mice were tested for reactivity against P2 peptide in ELISA. Specialized microtiter plates (Aquabind, M&E Biotech) were coated with 0.5 µg/well synthetic P2 peptide. The reactivities of diluted sera added to the wells were visualised using a HRP labelled goat anti-mouse secondary antibody (1:2000, Dako).

Anti-UniHis ELISA:

Pools of antisera from HIS-mIL5wt, HIS-mIL5.1 or PBS immunised mice were tested for reactivity against HIS-tag peptide (UNIZYME) in ELISA. Specialized microtiter plates (AquaBind, M&E Biotech) were coated with 0.5 µg/well synthetic HIS-tag peptide. The reactivities of diluted sera added to the wells were visualised using a HRP labelled goat anti-mouse secondary antibody (1:2000, Dako)

Anti-S2 Background Protein ELISA:

Pools of antisera from HIS-mIL5wt, HIS-mIL5.1 or PBS immunised mice were tested for reactivity against S2 background preparation in ELISA. Polystyrene microtiter plates (Maxisorp, Nunc) were coated with 0.1 µg/well S2 background preparation. The reactivities of diluted sera added to the wells were visualised using a HRP labelled goat anti-mouse secondary antibody (1:2000, Dako).

Anti-BSA ELISA:

Pools of antisera from HIS-mIL5 wt, HIS-mIL5.1 or PBS immunised mice were tested for reactivity against BSA in ELISA. Polystyrene microtiter plates (Maxisorp, Nunc) were coated with 10 µg/well BSA (Intergen). The reactivities of diluted sera added to the wells were visualised using a HRP labelled goat anti-mouse secondary antibody (1:2000, Dako).

Eosinophilia Model:

Balb/c J mice were sensitized with subcutaneous injections of 50 µg ovalbumin (OVA) in 0.9% saline mixed 1:1 with Adjuphos as alum adjuvant. OVA immunizations were repeated once per week for four weeks. One week after the last OVA sensitization, the mice were challenged with 12.5 µg OVA in 0.9% saline intranasal every other day for a total of 3 challenges. Bronchoalveolar lavage fluid (BALF) was collected one day after the last sensitization by cannulating the tracheae and washing the airway lumina with 1 ml 0.9% saline, or PBS.

BAL Staining:

Approximately 30,000-60,000 BALF cells were spun unto slides at 1,500 rpm for 20 minutes. The slides were dried overnight and stained for 2.5 minutes with May-Grunwald stain (Sigma), washed for 4 minutes in TBS, stained for 20-30 minutes with Giemsa stain (1:20 with ddH$_2$O; Sigma) and briefly rinsed with ddH$_2$O. Stained slides were dried overnight and cell types were identified using light microscopy. Approximately 100-200 cells were counted per slide and 3 slides were counted per mouse.

Results

Detection of Anti-mIL5 Antibodies:

A series of ELISA experiments were performed in order to investigate whether antibody responses specific for murine IL5 were induced in mice immunized with HIS-mIL5wt and HIS-mIL5.1 protein material. First, it was determined if antibodies against the HIS-mIL5wt immunization material were elicited by testing dilutions of antisera from individual mice on ELISA plates coated with the HIS-mIL5wt material. It was found that already by bleed one, all mice had developed high-titered antibody responses against the HIS-mIL5 wt material (E1320, expressed from *Drosophila* S2 cells and purified) which was estimated to be approximately 95% pure.

This result is not a firm confirmation that the antisera cross-reacts with murine IL5. In this setup, reactivities would also be detected against impurities from the *Drosophila* S2 cells, the S2 medium (which contain e.g. BSA from fetal calf serum, the HIS-tag as well as denatured mIL5 B cell epitopes. To demonstrate, that the antibodies induced contain reactivities against native murine IL5, the sera were tested in ELISA plates coated with mIL5 purchased from R&D systems. This material (R&D cat. no. 405-ML) is biologically active, contains no HIS-tag, is expressed in the bacculovirus Sf21 system, is also very pure (97%), and can be purchased free of carrier-protein (BSA) Pooled sera from both immunisation groups reacted with the purchased mIL5 coated on ELISA plates, whereas sera from PBS immunised mice did not. This was shown when testing sera from bleed 3 obtained at day 75, 11 days after the 4$^{th}$ immunization, but also sera from bleed 1 and 2 reacts with the purchased mIL5 in a similar setup. In order to exclude signals from cross-reaction with the BSA carrier, the experiments were repeated for bleeds 1 and 2 using carrierfree versions of the purchased mIL5 material and BSA-free ELISA buffers, and still high anti-mIL5 responses are seen.

To further confirm that the induced antisera cross-react with native mIL5, a competitive ELISA was set up. This ELISA tests the ability of the different antisera to inhibit the interaction between soluble native murine IL5 and monoclonal antibodies TRFK4 or TRFK5, which are both neutralizing antibodies.

Dilution series of antiserum pools were preincubated with soluble native mIL5 and the samples were added to ELISA plates coated with catching antibody TRFK5. Bound murine IL5 (which was not absorbed by the antisera) was next visualised using layers of biotinylated TRFK4 and subsequently horseradish peroxidase labeled streptavidin. An anti-mIL5 positive and an anti-mIL5 negative antiserum from DNA vaccinated mice were included as controls. It was demonstrated that antisera from both HIS-mIL5wt and HIS-mIL5.1 immunized mice could inhibit the interaction between soluble mIL5 and TRFK4 or TRFK5.

Based on the above-referenced it is concluded that mIL5 specific autoantibodies are induced in mice immunized with either the HIS-mIL5 wt or the HIS-mIL5.1 protein preparations (in 100% of the mice tested). In other words, B cell tolerance to mIL5 can be broken using recombinant HIS-tagged versions of both wild type and AutoVac murine IL5. A plausible explanation for the observation that B cell tolerance is broken to the wild type protein is that the HIS-tag in these mice functions as a 'foreign' immunogenic T helper epitope. Another explanation could be that the administration of Complete Freund's Adjuvant breaks B cell tolerance to mIL5. These hypotheses can be tested using non-HIS tagged antigens and/or alternative, less strong adjuvants such as AdjuPhos.

Further Characterization of the Antibody Responses in Mice Immunized with mIL5 AutoVac Proteins:

ELISA experiments were set up in order to determine whether antibodies specific for the inserted T helper epitope could be detected in sera from mIL5 protein immunised mice. For each immunisation group, antisera (bleed 2) were pooled and tested for reactivity against synthetic P2 peptide which had been immobilised in AquaBind microtiter plates. Anti-HIS-mIL5.1 antiserum contained reactivity against the inserted P2 peptide, whereas neither anti-HIS-mIL5wt or anti-PBS/CFA reacted with the peptide.

It was also tested whether the anti-HIS-mILwt and anti-HIS-mIL5.1 antisera contained reactivity against the 15-mer HIS-tag (UNIZYME HIS-tag, SEQ ID NO: 25) that is fused to the N-terminal of both the wild type and AutoVac mIL5 proteins. The peptide was synthesized and covalently immobilized in AquaBind microtiter plates, and pooled antisera from each immunization group (bleeds 1, 2 and 3) were tested for reactivity against the bound peptide. Antisera from all protein immunized mice reacted with the synthetic HIS-tag peptide.

It was also tested whether the anti-HIS-mIL5wt and anti-HIS-mIL5.1 antisera was reactive with components from the S2 Drosophila cells or culture medium. ELISA plates coated with BSA (a major medium component) or S2-background preparation (generated by subjecting culture supernatant from Her2 expressing *Drosophila* S2 cells to a purification scheme similar to that of the mIL5 purification procedure). The results of these analyses demonstrated that whereas the anti-BSA responses were very low, the reactions with the S2-background material were pronounced.

Eosinophil Counts in BALF:

To determine if the anti-IL5 antibodies in vaccinated mice could down-regulate the in vivo activity of IL5, we induced IL5-dependent eosinophilia in the lungs of the vaccinated mice. Eosinophils were induced by challenging sensitized mice with OVA intranasally. High numbers of eosinophils were induced in control OVA mice and mice vaccinated with UniHis-mIL5.1, but not in Uni-His-mIL5 or PBS vaccinated mice. The discrepancy of eosinophil numbers between control groups (OVA and PBS) and experimental groups (Uni-His-mIL5 and UniHis-mIL5.1), and the positive results from the DNA vaccinated mice reported above, led us to believe that the groups may have been switched. However, no attempts to demonstrate a switch supported this interpretation. The protein vaccinations are being repeated in an identical setup to clarify this controversy.

Discussion

The ability of both the UniHis-mIL5 and UniHis-mIL5.1 proteins to induce antibodies that cross-react with wildtype murine IL5 was clearly demonstrated. Whether the ability of the UniHis-mIL5 protein to bypass immunological tolerance is due to the UniHis-tag, or some other reason (e.g. CFA adjuvant) remains to be clarified. It was surprising to see that only the Uni-His-mIL5 construct was able to down-regulate the endogenous in vivo activity of mIL5 in an eosinophilia model. This inability of antisera generated from UniHis-mIL5.1 protein vaccination to inhibit eosinophilia, and its ability to inhibit eosinophilia via DNA vaccinations suggests that a technical mistake may have occurred in this experiment. This is also supported by the unusual finding of PBS vaccination inhibiting eosinophilia. This most likely explanation is that these two groups (PBS and UniHis-mIL5.1) were switched.

LIST OF REFERENCES

Akutsu I. et al., 1995, Immunol. Lett., 45: 109-116. Alexander A. G. et al., 1994, Thorax, 49(12): 1231-1233.
Azuma C. et al., 1986, Nucleic Acid Res. 1986, 14(22): 9149-9158.
Barata L. T. et al., 1998, J. Allergy and Clin. Immunol, 101: 222-230.
Baumann M. A. et al., 1997, Methods, 11: 88-97
Callard R. E. & Gearing A. J. H., 'IL-5', Cytokine Facts Book 1994, Academic Press.
Campbell H. D. et al., 1988, Eur. J. Biochem., 174: 345-352.
Chand N. et al., 1992, Eur. J. Immunol., 211: 121-123.
Coeffier E. et al., 1994, Br. J. Pharmacol., 113(3): 749-56.

Coffman R. L. et al., 1989, Science, 245: 308-310.
Corrigan C. J. & Kay A. B., 1996, Eur. Resp. J., 9, suppl. 22: 72s-78s.
Cousins D. J. et al., 1994, Am. J. Resp. Crit. Care. Med., 150: S50-S53.
Danzig M. et al., 1997, Allergy, 52(8): 787-794.
Dickason R. R. et al., 1994, Cytokine, 6(6): 647-656.
Dickason R. R. et al., 1996a, Nature, 379: 652-655.
Dickason R. R. et al., 1996b, J. Mol. Med., 74(9), 535-546
Egan R. W. et al., 1995, Int. Arch. Allergy Immunol., 107: 321-322.
Foster P. S. et al., 1996, J. Exp. Med., 183: 195-201.
Graber P. et al., 1993, Eur. J. Biochem., 212(3): 751-755.
Graber P. et al., 1995, J. Biol. Chem., 270(26): 15762-15769.
Hamelmann E. et al., 1997, Am. J. Crit. Care Med., 155 (3): 819-825.
Huston M. M. et al., 1996, J. Immunol., 156(4): 1392-1401.
Karlen S. et al., 1998, Int. Rev. Immunol., 16(3-4): 227-247.
Kodama S. et al., 1993, Eur. J. Biochem., 211(3): 903-908.
Kopf M. et al., 1996, Immunity, 4: 15-24.
Kung T. T. et al., 1995, Am. J. Respir. Cell. Mol. Biol., 13: 360-365.
Lee N. A. et al., 1997a, J. Immunol., 158: 1332-1344.
Lee J. J. et al., 1997b, J. Exp. Med. 1997b, 185 (12): 2143-2156.
Lopez A. F. et al., 1992, Immunology Today, 13: 495-500.
Mauser P. J. et al., 1993, Am. Rev. Respir. Dis., 148: 1623-1627.
Mauser P. J. et al., 1995, Am. J. Respir. Crit. Care Med., 152(2): 467-472.
Milburn M. V. et al., 1993, Nature, 363: 172-176.
Mori A. et al., 1997, J. Allergy Clin. Immunol., 100(6) Pt 2: S56-64.
Moxham J. & Costello J. F., 'Respiratory diseases', chapt. 14, Textbook of Medicine, Churchill Livingstone 1990, Ed. Souhami R. L. and Moxham J.
Nagai H. et al., 1993a, Ann. N.Y. Acad.Sci., 91-96.
Nagai H. et al., 1993b, Life Sciences, 53: μL 243-247.
Ohashi Y. et al., 1998, Scand. J. Immunol., 47: 596-602.
Ortega D. & Busse W. W., 'Asthma: Pathogenesis and treatment', chapt. 28, Allergy, W.B. Saunders Company 1997, Ed. Kaplan A. P.
Proudfoot A. E. et al., 1990, Biochem J., 270(2): 357-361.
Proudfoot A. E. et al., 1996, J. Protein Chem., 15(5): 491-499.
Rose K. et al., 1992, Biochem J, 286(Pt 3): 825-828.
Sanderson C. J., 1992, Blood, 79 (12): 3101-3109.
Sher A. et al., 1990, J. Immunol., 145: 3911-3916.
Takatsu K. et al., Interleukin-5, Growth Factors and Cytokines in Health and Disease 1997, vol. 2A, JAI Press Inc., Ed. Leroith D. & Bondy C.
Tanabe T. et al., 1987, J. Biol. Chem., 262: 16580-16584.
Tavernier J. et al., 1989, DNA, 8(7), 491-501.
Tominaga A. et al., 1990, J. Immunol., 144(4): 1345-1352.
Tominaga A. et al., 1991, J. Exp. Med., 173(2): 429-437.
Underwood D. C. et al., 1996, Am. J. Resp. Crit. Care Med., 154: 850-857.
van Oosterhout A. J. M. et al., 1993, Am. Rev. Resp. Dis., 147: 548-552.
van Oosterhout A. J. M. et al., 1995, Am. J. Respir. Crit. Care Med., 151: 177-183.
Villinger F. et al., 1995, J. Immunol., 155: 3946-3954.
Wang P. et al., 1998, J. Immunol., 160: 4427-4432.
Yamaguchi Y. et al., 1991, Blood, 78(10): 2542-2547.

The invention claimed is:

1. A method of in vivo down-regulation of interleukin 5 (IL5) activity in an animal, including a human being, the method comprising administering an immunogenically effective amount of at least one $T_H$ epitope-containing IL5 polypeptide wherein said $T_H$ epitope-containing IL5 polypeptide differs from the animal's autologous IL5 polypeptide in that the $T_H$ epitope-containing IL5 polypeptide comprises at least one foreign $T_H$ epitope introduced into the amino acid sequence of the animal's autologous IL5 polypeptide, whereby immunization of the animal with the $T_H$ epitope-containing IL5 polypeptide produces antibodies against the animal's autologous IL5 polypeptide and whereby said $T_H$ epitope-containing IL5 polypeptide reacts to the same extent with an atiserum raised against the animal's autologous IL5 as does the autologous IL5 and wherein the $T_H$ epitope-containing IL5 polypeptide comprises a foreign $T_H$ epitope in at least one of loops 1-3 or in the amino acid residues C-terminal to helix D, said loops and said helix D corresponding to those shown in FIG. 3 for human and murine IL5, SEQ ID NO: 1, SEQ ID NO: 12, respectively.

2. The method according to claim 1, wherein the foreign $T_H$ epitope is immunodominant in the animal.

3. The method according to claim 1, wherein the foreign $T_H$ epitope is promiscuous.

4. The method according to claim 3, wherein the at least one foreign $T_H$ epitope is selected from a natural promiscuous T-cell epitope and an artificial MHC-II binding peptide sequence.

5. The method according to claim 4, wherein the natural $T_H$ epitope is selected from the group consisting of a Tetanus toxoid epitope, a diphtheria toxoid epitope, an influenza virus hemagluttinin epitope, and a *P. faciparum* CS epitope.

6. The method according to claim 5, wherein said Tetanus toxoid epitope is P2 or P30.

7. The method according to claim 1, wherein the IL5 polypeptide is a human IL5 polypeptide.

8. The method according to claim 7, wherein the human IL5 polypeptide has been modified by substituting at least one amino acid sequence in SEQ ID NO: 1 with at least one amino acid sequence of equal or different length thereby giving rise to a foreign $T_H$ epitope, wherein substitute amino acid residues are selected from the group consisting of residues 87-90, residues 88-91, residues 32-43, residues 33-43, residues 59-64, residues 86-91, and residues 110-113.

9. The method according to claim 1, wherein the $T_H$ epitope-containing IL5 polypeptide is administered together with an adjuvant which facilitates breaking of autotolerance to autoantigens.

10. The method according to claim 9, wherein the adjuvant is selected from the group consisting of an immune targeting adjuvant; an immune modulating adjuvant; an oil formulation; a polymer; a micelle forming adjuvant; a saponin; an immunostimulating complex matrix (as ISCOM matrix); DDA; aluminum adjuvants; DNA adjuvants; γ-inulin; and an encapsulating adjuvant.

11. The method according to claim 1, wherein an effective amount of the $T_H$ epitope-containing IL5 polypeptide is administered to the animal via a route selected from the parenteral route; the peritoneal route; the oral route; the buccal route; the sublingual route; the epidural route; the spinal route; the anal route; and the intracranial route.

12. The method according to claim 11, wherein said potential route is a member selected from the group consisting of the intradermal, the subdermal, the intracutaneous, the subcutaneous, and the intramuscular routes.

13. The method according to claim 11, wherein the effective amount is between 0.5 μg and 2,000 μg of the IL5 polypeptide.

14. The method according to claim 11, which includes at least one administration of the IL5 polypeptide per year.

15. The method according to claim 11, wherein the IL5 polypeptide is contained in a virtual lymph node (VLN) device.

16. The method according to claim 10, wherein said immune modulating adjuvant is a member selected from the group consisting of a toxin, a cytokine and a mycobacterial derivative.

17. A method for treating asthma or other chronic allergic conditions characterized by eosinophilia, the method comprising administering to a patient in need thereof an immunogenically effective amount of at least one $T_H$ epitope-containing IL5 polypeptide wherein said $T_H$ epitope-containing IL5 polypeptide differs from the animal's autologous IL5 polypeptide in that the $T_H$ epitope-containing IL5 polypeptide comprises at least one foreign $T_H$ epitope inserted into the amino acid sequence of the animal's autologous IL5 polypeptide, whereby immunization of the animal with the $T_H$ epitope-containing IL5 polypeptide produces antibodies against the animal's autologous IL5 polypeptide whereby said $T_H$ epitope-containing IL5 polypeptide reacts to the same extent with an antiserum raised against the animal's autologous IL5 as does the autologous IL5 and wherein the $T_H$ epitope-containing IL5 polypeptide comprises a foreign $T_H$ epitope in at least one of loops 1-3 or in the amino acid residues C-terminal to helix-D, said loops and said helix D corresponding to those shown in FIG. 3 for human and murine IL5, SEQ ID NO: 1 and SEQ ID NO: 12, respectively.

* * * * *

UNITED STATES PATENT AND TRADEMARK OFFICE
CERTIFICATE OF CORRECTION

PATENT NO. : 7,285,273 B1
APPLICATION NO. : 09/980916
DATED : October 23, 2007
INVENTOR(S) : Steen Klysner Page 1 of 1

It is certified that error appears in the above-identified patent and that said Letters Patent is hereby corrected as shown below:

In Claim 1, Col. 121 line 56, "atiserum" should read --antiserum--.

In Claim 5, Col. 122 line 47, "*P. faciparum*" should read --*P. falciparum*--.

In Claim 12, Col. 123 line 11, "potential" should read --parenteral--.

Signed and Sealed this

Twentieth Day of May, 2008

JON W. DUDAS
*Director of the United States Patent and Trademark Office*

SEQUENCE LISTING

```
<160> NUMBER OF SEQ ID NOS: 65

<210> SEQ ID NO 1
<211> LENGTH: 115
<212> TYPE: PRT
<213> ORGANISM: Homo sapiens
<220> FEATURE:
<221> NAME/KEY: DISULFID
<222> LOCATION: (44)
<223> OTHER INFORMATION: Interchain disulphide bond to Cys-86 in SEQ ID
      NO:1
<221> NAME/KEY: DISULFID
<222> LOCATION: (86)
<223> OTHER INFORMATION: Interchain disulphide bond to Cys-44 in SEQ ID
      NO:1

<400> SEQUENCE: 1

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
                20                  25                  30

Ile Pro Val Pro Val His Lys Asn His Gln Leu Cys Thr Glu Glu Ile
            35                  40                  45

Phe Gln Gly Ile Gly Thr Leu Glu Ser Gln Thr Val Gln Gly Gly Thr
        50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Glu Arg Arg Arg Val Asn Gln Phe
```

```
                    85                  90                  95
Leu Asp Tyr Leu Gln Glu Phe Leu Gly Val Met Asn Thr Glu Trp Ile
            100                 105                 110

Ile Glu Ser
        115

<210> SEQ ID NO 2
<211> LENGTH: 126
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      epitope
<221> NAME/KEY: MUTAGEN
<222> LOCATION: (32)..(46)
<223> OTHER INFORMATION: Tetanus toxoid P2 epitope (SEQ ID NO: 23)
<221> NAME/KEY: SIMILAR
<222> LOCATION: (1)..(86)
<223> OTHER INFORMATION: Identical to residues 1-86 in SEQ ID NO: 1
<221> NAME/KEY: SIMILAR
<222> LOCATION: (102)..(126)
<223> OTHER INFORMATION: Identical to residues 91-115 in SEQ ID NO: 1

<400> SEQUENCE: 2

Ile Pro Thr Glu Ile Pro Thr Ser Ala Leu Val Lys Glu Thr Leu Ala
  1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
 65                  70                  75                  80

Gly Gln Lys Lys Lys Cys Gln Tyr Ile Lys Ala Asn Ser Lys Phe Ile
                85                  90                  95

Gly Ile Thr Glu Leu Arg Arg Val Asn Gln Phe Leu Asp Tyr Leu Gln
            100                 105                 110

Glu Phe Leu Gly Val Met Asn Thr Glu Trp Ile Ile Glu Ser
        115                 120                 125

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      epitope
<221> NAME/KEY: MUTAGEN
<222> LOCATION: (32)..(46)
<223> OTHER INFORMATION: Tetanus toxoid P2 epitope (SEQ ID NO: 23)
<221> NAME/KEY: SIMILAR
<222> LOCATION: (1)..(31)
<223> OTHER INFORMATION: Identical to residues 1-31 in SEQ ID NO: 1
<221> NAME/KEY: SIMILAR
<222> LOCATION: (47)..(118)
<223> OTHER INFORMATION: Identical to residues 44-115 in SEQ ID NO: 1

<400> SEQUENCE: 3

Ile Pro Thr Glu Ile Pro Thr Ser Ala Leu Val Lys Glu Thr Leu Ala
  1               5                  10                  15

Leu Leu Ser Thr His Arg Thr Leu Leu Ile Ala Asn Glu Thr Leu Gln
            20                  25                  30
```

```
Tyr Ile Lys Ala Asn Ser Lys Phe Ile Gly Ile Thr Glu Leu Cys Thr
            35                  40                  45

Glu Glu Ile Phe Gln Gly Ile Gly Thr Leu Glu Ser Gln Thr Val Gln
        50                  55                  60

Gly Gly Thr Val Glu Arg Leu Phe Lys Asn Leu Ser Leu Ile Lys Lys
 65                  70                  75                  80

Tyr Ile Asp Gly Gln Lys Lys Cys Gly Glu Arg Arg Arg Val
                85                  90                  95

Asn Gln Phe Leu Asp Tyr Leu Gln Glu Phe Leu Gly Val Met Asn Thr
            100                 105                 110

Glu Trp Ile Ile Glu Ser
            115

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      epitope
<221> NAME/KEY: MUTAGEN
<222> LOCATION: (59)..(73)
<223> OTHER INFORMATION: Tetanus toxoid P2 epitope (SEQ ID NO:23)
<221> NAME/KEY: SIMILAR
<222> LOCATION: (1)..(58)
<223> OTHER INFORMATION: Identical to residues 1-58 in SEQ ID NO: 1
<221> NAME/KEY: SIMILAR
<222> LOCATION: (74)..(124)
<223> OTHER INFORMATION: Identical to residues 65-115 in SEQ ID NO: 1

<400> SEQUENCE: 4

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Gln Tyr Ile Lys Ala Asn
     50                  55                  60

Ser Lys Phe Ile Gly Ile Thr Glu Leu Val Glu Arg Leu Phe Lys Asn
 65                  70                  75                  80

Leu Ser Leu Ile Lys Lys Tyr Ile Asp Gly Gln Lys Lys Lys Cys Gly
            85                  90                  95

Glu Glu Arg Arg Arg Val Asn Gln Phe Leu Asp Tyr Leu Gln Glu Phe
        100                 105                 110

Leu Gly Val Met Asn Thr Glu Trp Ile Ile Glu Ser
        115                 120

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      epitope
<221> NAME/KEY: MUTAGEN
<222> LOCATION: (86)..(100)
<223> OTHER INFORMATION: Tetanus toxoid P2 epitope (SEQ ID NO: 23)
<221> NAME/KEY: SIMILAR
<222> LOCATION: (1)..(85)
<223> OTHER INFORMATION: Identical to residues 1-85 in SEQ ID NO: 1
```

-continued

```
<221> NAME/KEY: SIMILAR
<222> LOCATION: (101)..(124)
<223> OTHER INFORMATION: Identical to residues 90-115 in SEQ ID NO: 1

<400> SEQUENCE: 5

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
         35                  40                  45

Phe Gln Gly Ile Gly Thr Leu Glu Ser Gln Thr Val Gln Gly Gly Thr
     50                  55                  60

Val Glu Arg Leu Phe Lys Asn Leu Ser Leu Ile Lys Lys Tyr Ile Asp
 65                  70                  75                  80

Gly Gln Lys Lys Lys Gln Tyr Ile Lys Ala Asn Ser Lys Phe Ile Gly
                 85                  90                  95

Ile Thr Glu Leu Arg Val Asn Gln Phe Leu Asp Tyr Leu Gln Glu Phe
            100                 105                 110

Leu Gly Val Met Asn Thr Glu Trp Ile Ile Glu Ser
        115                 120

<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      epitope
<221> NAME/KEY: MUTAGEN
<222> LOCATION: (110)..(124)
<223> OTHER INFORMATION: Tetanus toxoid P2 epitope (SEQ ID NO: 23)
<221> NAME/KEY: SIMILAR
<222> LOCATION: (1)..(109)
<223> OTHER INFORMATION: Identical to residues 1-109 in SEQ ID NO: 1
<221> NAME/KEY: SIMILAR
<222> LOCATION: (125)..(126)
<223> OTHER INFORMATION: Identical to residues 114-115 in SEQ ID NO: 1

<400> SEQUENCE: 6

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
         35                  40                  45

Phe Gln Gly Ile Gly Thr Leu Glu Ser Gln Thr Val Gln Gly Gly Thr
     50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Arg Arg Val Asn Gln Phe
                 85                  90                  95

Leu Asp Tyr Leu Gln Glu Phe Leu Gly Val Met Asn Thr Gln Tyr Ile
            100                 105                 110

Lys Ala Asn Ser Lys Phe Ile Gly Ile Thr Glu Leu Glu Ser
        115                 120                 125

<210> SEQ ID NO 7
<211> LENGTH: 132
<212> TYPE: PRT
```

```
<213> ORGANISM: Artificial Sequence
<220> FEATURE:
<223> OTHER INFORMATION: Description of Artificial Sequence:Human IL5
      modified by substitution with tetanus toxoid P30
      epitope
<221> NAME/KEY: MUTAGEN
<222> LOCATION: (87)..(107)
<223> OTHER INFORMATION: Tetanus toxoid P30 epitope (SEQ ID NO: 24)
<221> NAME/KEY: SIMILAR
<222> LOCATION: (1)..(86)
<223> OTHER INFORMATION: Identical to residues 1-86 in SEQ ID NO: 1
<221> NAME/KEY: SIMILAR
<222> LOCATION: (108)..(132)
<223> OTHER INFORMATION: Identical to residues 91-115 in SEQ ID NO: 1

<400> SEQUENCE: 7

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Phe Asn Asn Phe Thr Val Ser Phe Trp Leu
                85                  90                  95

Arg Val Pro Lys Val Ser Ala Ser His Leu Glu Arg Arg Val Asn Gln
            100                 105                 110

Phe Leu Asp Tyr Leu Gln Glu Phe Leu Gly Val Met Asn Thr Glu Trp
        115                 120                 125

Ile Ile Glu Ser
        130

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P30
      epitope
<221> NAME/KEY: MUTAGEN
<222> LOCATION: (32)..(52)
<223> OTHER INFORMATION: Tetanus toxoid P30 epitope (SEQ ID NO: 24)
<221> NAME/KEY: SIMILAR
<222> LOCATION: (1)..(31)
<223> OTHER INFORMATION: Identical to residues 1-31 in SEQ ID NO: 1
<221> NAME/KEY: SIMILAR
<222> LOCATION: (53)..(124)
<223> OTHER INFORMATION: Identical to residues 44-115 in SEQ ID NO: 1

<400> SEQUENCE: 8

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Phe
            20                  25                  30

Asn Asn Phe Thr Val Ser Phe Trp Leu Arg Val Pro Lys Val Ser Ala
        35                  40                  45

Ser His Leu Glu Cys Thr Glu Glu Ile Phe Gln Gly Ile Gly Thr Leu
    50                  55                  60

Glu Ser Gln Thr Val Gln Gly Gly Thr Val Glu Arg Leu Phe Lys Asn
65                  70                  75                  80
```

```
Leu Ser Leu Ile Lys Lys Tyr Ile Asp Gly Gln Lys Lys Cys Gly
            85                  90                  95

Glu Glu Arg Arg Arg Val Asn Gln Phe Leu Asp Tyr Leu Gln Glu Phe
            100                 105                 110

Leu Gly Val Met Asn Thr Glu Trp Ile Ile Glu Ser
            115                 120

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P30
      epitope
<221> NAME/KEY: MUTAGEN
<222> LOCATION: (59)..(79)
<223> OTHER INFORMATION: Tetanus toxoid P30 epitope (SEQ ID NO: 24)
<221> NAME/KEY: SIMILAR
<222> LOCATION: (1)..(58)
<223> OTHER INFORMATION: Identical to residues 1-58 in SEQ ID NO: 1
<221> NAME/KEY: SIMILAR
<222> LOCATION: (80)..(130)
<223> OTHER INFORMATION: Identical to residues 65-115 in SEQ ID NO: 1

<400> SEQUENCE: 9

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
            35                  40                  45

Phe Gln Gly Ile Gly Thr Leu Glu Ser Gln Phe Asn Asn Phe Thr Val
        50                  55                  60

Ser Phe Trp Leu Arg Val Pro Lys Val Ser Ala Ser His Leu Glu Val
65                  70                  75                  80

Glu Arg Leu Phe Lys Asn Leu Ser Leu Ile Lys Lys Tyr Ile Asp Gly
            85                  90                  95

Gln Lys Lys Lys Cys Gly Glu Glu Arg Arg Arg Val Asn Gln Phe Leu
            100                 105                 110

Asp Tyr Leu Gln Glu Phe Leu Gly Val Met Asn Thr Glu Trp Ile Ile
            115                 120                 125

Glu Ser
    130

<210> SEQ ID NO 10
<211> LENGTH: 132
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P30
      epitope
<221> NAME/KEY: MUTAGEN
<222> LOCATION: (110)..(130)
<223> OTHER INFORMATION: Tetanus toxoid P30 epitope (SEQ ID NO: 24)
<221> NAME/KEY: SIMILAR
<222> LOCATION: (1)..(129)
<223> OTHER INFORMATION: Identical to residues 1-129 in SEQ ID NO: 1
<221> NAME/KEY: SIMILAR
<222> LOCATION: (131)..(132)
<223> OTHER INFORMATION: Identical to residues 114-115 in SEQ ID NO: 1

<400> SEQUENCE: 10
```

```
Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Val Asn Gln Phe
                85                  90                  95

Leu Asp Tyr Leu Gln Glu Phe Leu Gly Val Met Asn Thr Phe Asn Asn
                100                 105                 110

Phe Thr Val Ser Phe Trp Leu Arg Val Pro Lys Val Ser Ala Ser His
            115                 120                 125

Leu Glu Glu Ser
    130
```

<210> SEQ ID NO 11
<211> LENGTH: 141
<212> TYPE: PRT
<213> ORGANISM: Artificial Sequence
<220> FEATURE:
<223> OTHER INFORMATION: Description of Artificial Sequence:Human IL5
      modified by substitution with tetanus toxoid P2
      and P30 epitopes
<221> NAME/KEY: MUTAGEN
<222> LOCATION: (86)..(100)
<223> OTHER INFORMATION: Tetanus toxoid P2 epitope (SEQ ID NO: 23)
<221> NAME/KEY: MUTAGEN
<222> LOCATION: (119)..(139)
<223> OTHER INFORMATION: Tetanus toxoid P30 epitope (SEQ ID NO: 24)
<221> NAME/KEY: SIMILAR
<222> LOCATION: (1)..(85)
<223> OTHER INFORMATION: Identical to residues 1-85 in SEQ ID NO: 1
<221> NAME/KEY: SIMILAR
<222> LOCATION: (101)..(118)
<223> OTHER INFORMATION: Identical to residues 92-109 in SEQ ID NO: 1
<221> NAME/KEY: SIMILAR
<222> LOCATION: (140)..(141)
<223> OTHER INFORMATION: Identical to residues 114-115 in SEQ ID NO: 1

<400> SEQUENCE: 11

```
Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Gln Tyr Ile Lys Ala Asn Ser Lys Phe Ile Gly
                85                  90                  95

Ile Thr Glu Leu Arg Val Asn Gln Phe Leu Asp Tyr Leu Gln Glu Phe
                100                 105                 110

Leu Gly Val Met Asn Thr Phe Asn Asn Phe Thr Val Ser Phe Trp Leu
            115                 120                 125

Arg Val Pro Lys Val Ser Ala Ser His Leu Glu Glu Ser
```

```
                130                 135                 140

<210> SEQ ID NO 12
<211> LENGTH: 113
<212> TYPE: PRT
<213> ORGANISM: Mus musculus
<220> FEATURE:
<221> NAME/KEY: DISULFID
<222> LOCATION: (42)
<223> OTHER INFORMATION: Interchain disulphide bond to Cys-84 in SEQ ID
      NO:12
<221> NAME/KEY: DISULFID
<222> LOCATION: (84)
<223> OTHER INFORMATION: Interchain disulphide bond to Cys-42 in SEQ ID
      NO:12

<400> SEQUENCE: 12

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
            35                  40                  45

Gly Leu Asp Ile Leu Lys Asp Gln Thr Val Arg Gly Gly Thr Val Met
 50                  55                  60

Arg Leu Phe Gln Asn Leu Ser Leu Ile Lys Lys Tyr Ile Asp Arg Gln
 65                  70                  75                  80

Glu Lys Lys Cys Gly Glu Glu Arg Arg Arg Thr Arg Gln Phe Leu Asp
                85                  90                  95

Tyr Leu Gln Glu Phe Leu Gly Ser Met Asn Thr Ala Ala Ile Ile Glu
            100                 105                 110

Gly

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      epitope
<221> NAME/KEY: MUTAGEN
<222> LOCATION: (85)..(99)
<223> OTHER INFORMATION: Tetanus toxoid P2 epitope (SEQ ID NO: 23)
<221> NAME/KEY: SIMILAR
<222> LOCATION: (1)..(84)
<223> OTHER INFORMATION: Identical to residues 1-84 in SEQ ID NO: 12
<221> NAME/KEY: SIMILAR
<222> LOCATION: (100)..(124)
<223> OTHER INFORMATION: Identical to residues 89-113 in SEQ ID NO: 12

<400> SEQUENCE: 13

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
            35                  40                  45

Gly Leu Asp Ile Leu Lys Asp Gln Thr Val Arg Gly Gly Thr Val Met
 50                  55                  60

Arg Leu Phe Gln Asn Leu Ser Leu Ile Lys Lys Tyr Ile Asp Arg Gln
 65                  70                  75                  80

Glu Lys Lys Cys Gln Tyr Ile Lys Ala Asn Ser Lys Phe Ile Gly Ile
```

-continued

```
                85                  90                  95
Thr Glu Leu Arg Arg Thr Arg Gln Phe Leu Asp Tyr Leu Gln Glu Phe
            100                 105                 110

Leu Gly Ser Met Asn Thr Ala Ala Ile Ile Glu Gly
        115                 120

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      epitope
<221> NAME/KEY: MUTAGEN
<222> LOCATION: (30)..(44)
<223> OTHER INFORMATION: Tetanus toxoid P2 epitope (SEQ ID NO: 23)
<221> NAME/KEY: SIMILAR
<222> LOCATION: (1)..(29)
<223> OTHER INFORMATION: Identical to residues 1-29 in SEQ ID NO: 12
<221> NAME/KEY: SIMILAR
<222> LOCATION: (45)..(116)
<223> OTHER INFORMATION: Identical to residues 42-113 in SEQ ID NO: 12

<400> SEQUENCE: 14

Met Glu Ile Pro Met Ser Thr Val Val Lys Glu Thr Leu Ala Leu Leu
  1               5                  10                  15

Ser Ala His Arg Ala Leu Leu Thr Ser Asn Glu Thr Met Gln Tyr Ile
             20                  25                  30

Lys Ala Asn Ser Lys Phe Ile Gly Ile Thr Glu Leu Cys Ile Gly Glu
         35                  40                  45

Ile Phe Gln Gly Leu Asp Ile Leu Lys Asp Gln Thr Val Arg Gly Gly
     50                  55                  60

Thr Val Met Arg Leu Phe Gln Asn Leu Ser Leu Ile Lys Lys Tyr Ile
 65                  70                  75                  80

Asp Arg Gln Glu Lys Lys Cys Gly Glu Glu Arg Arg Arg Thr Arg Gln
                 85                  90                  95

Phe Leu Asp Tyr Leu Gln Glu Phe Leu Gly Ser Met Asn Thr Ala Ala
            100                 105                 110

Ile Ile Glu Gly
        115

<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      epitope
<221> NAME/KEY: MUTAGEN
<222> LOCATION: (57)..(71)
<223> OTHER INFORMATION: Tetanus toxoid P2 epitope (SEQ ID NO: 23)
<221> NAME/KEY: SIMILAR
<222> LOCATION: (1)..(56)
<223> OTHER INFORMATION: Identical to residues 1-56 in SEQ ID NO: 12
<221> NAME/KEY: SIMILAR
<222> LOCATION: (72)..(122)
<223> OTHER INFORMATION: Identical to residues 63-113 in SEQ ID NO: 12

<400> SEQUENCE: 15

Met Glu Ile Pro Met Ser Thr Val Val Lys Glu Thr Leu Ala Leu Leu
  1               5                  10                  15

Ser Ala His Arg Ala Leu Leu Thr Ser Asn Glu Thr Met Arg Leu Pro
             20                  25                  30
```

```
Val Pro Thr His Lys Asn His Gln Leu Cys Ile Gly Glu Ile Phe Gln
        35                  40                  45

Gly Leu Asp Ile Leu Lys Asp Gln Gln Tyr Ile Lys Ala Asn Ser Lys
    50                  55                  60

Phe Ile Gly Ile Thr Glu Leu Val Met Arg Leu Phe Gln Asn Leu Ser
65                  70                  75                  80

Leu Ile Lys Lys Tyr Ile Asp Arg Gln Glu Lys Lys Cys Gly Glu Glu
                85                  90                  95

Arg Arg Arg Thr Arg Gln Phe Leu Asp Tyr Leu Gln Glu Phe Leu Gly
            100                 105                 110

Ser Met Asn Thr Ala Ala Ile Ile Glu Gly
            115                 120

<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      epitope
<221> NAME/KEY: MUTAGEN
<222> LOCATION: (84)..(98)
<223> OTHER INFORMATION: Tetanus toxoid P2 epitope (SEQ ID NO: 23)
<221> NAME/KEY: SIMILAR
<222> LOCATION: (1)..(83)
<223> OTHER INFORMATION: Identical to residues 1-83 in SEQ ID NO: 12
<221> NAME/KEY: SIMILAR
<222> LOCATION: (99)..(122)
<223> OTHER INFORMATION: Identical to residues 90-113 in SEQ ID NO: 12

<400> SEQUENCE: 16

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
        35                  40                  45

Gly Leu Asp Ile Leu Lys Asp Gln Thr Val Arg Gly Thr Val Met
    50                  55                  60

Arg Leu Phe Gln Asn Leu Ser Leu Ile Lys Lys Tyr Ile Asp Arg Gln
65                  70                  75                  80

Glu Lys Lys Gln Tyr Ile Lys Ala Asn Ser Lys Phe Ile Gly Ile Thr
                85                  90                  95

Glu Leu Arg Thr Arg Gln Phe Leu Asp Tyr Leu Gln Glu Phe Leu Gly
            100                 105                 110

Ser Met Asn Thr Ala Ala Ile Ile Glu Gly
            115                 120

<210> SEQ ID NO 17
<211> LENGTH: 124
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      epitope
<221> NAME/KEY: MUTAGEN
<222> LOCATION: (108)..(122)
<223> OTHER INFORMATION: Tetanus toxoid P2 epitope (SEQ ID NO: 23)
<221> NAME/KEY: SIMILAR
<222> LOCATION: (1)..(107)
<223> OTHER INFORMATION: Identical to residues 1-107 in SEQ ID NO: 12
```

```
<221> NAME/KEY: SIMILAR
<222> LOCATION: (123)..(124)
<223> OTHER INFORMATION: Identical to residues 112-113 in SEQ ID NO: 12

<400> SEQUENCE: 17
```

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
            35                  40                  45

Gly Leu Asp Ile Leu Lys Asp Gln Thr Val Arg Gly Gly Thr Val Met
    50                  55                  60

Arg Leu Phe Gln Asn Leu Ser Leu Ile Lys Lys Tyr Ile Asp Arg Gln
65                  70                  75                  80

Glu Lys Lys Cys Gly Glu Glu Arg Arg Arg Thr Arg Gln Phe Leu Asp
                85                  90                  95

Tyr Leu Gln Glu Phe Leu Gly Ser Met Asn Thr Gln Tyr Ile Lys Ala
            100                 105                 110

Asn Ser Lys Phe Ile Gly Ile Thr Glu Leu Glu Gly
        115                 120

```
<210> SEQ ID NO 18
<211> LENGTH: 130
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P30
      epitope
<221> NAME/KEY: MUTAGEN
<222> LOCATION: (85)..(105)
<223> OTHER INFORMATION: Tetanus toxoid P2 epitope (SEQ ID NO: 24)
<221> NAME/KEY: SIMILAR
<222> LOCATION: (1)..(84)
<223> OTHER INFORMATION: Identical to residues 1-84 in SEQ ID NO: 12
<221> NAME/KEY: SIMILAR
<222> LOCATION: (106)..(130)
<223> OTHER INFORMATION: Identical to residues 89-113 in SEQ ID NO: 12

<400> SEQUENCE: 18
```

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
            35                  40                  45

Gly Leu Asp Ile Leu Lys Asp Gln Thr Val Arg Gly Gly Thr Val Met
    50                  55                  60

Arg Leu Phe Gln Asn Leu Ser Leu Ile Lys Lys Tyr Ile Asp Arg Gln
65                  70                  75                  80

Glu Lys Lys Cys Phe Asn Asn Phe Thr Val Ser Phe Trp Leu Arg Val
                85                  90                  95

Pro Lys Val Ser Ala Ser His Leu Glu Arg Arg Thr Arg Gln Phe Leu
            100                 105                 110

Asp Tyr Leu Gln Glu Phe Leu Gly Ser Met Asn Thr Ala Ala Ile Ile
        115                 120                 125

Glu Gly
130

```
<210> SEQ ID NO 19
<211> LENGTH: 122
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P30
      epitope
<221> NAME/KEY: MUTAGEN
<222> LOCATION: (30)..(50)
<223> OTHER INFORMATION: Tetanus toxoid P30 epitope (SEQ ID NO: 24)
<221> NAME/KEY: SIMILAR
<222> LOCATION: (1)..(29)
<223> OTHER INFORMATION: Identical to residues 1-29 in SEQ ID NO: 12
<221> NAME/KEY: SIGNAL
<222> LOCATION: (51)..(122)
<223> OTHER INFORMATION: Identical to residues 42-113 in SEQ ID NO: 12

<400> SEQUENCE: 19

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Phe Asn Asn
                20                  25                  30

Phe Thr Val Ser Phe Trp Leu Arg Val Pro Lys Val Ser Ala Ser His
            35                  40                  45

Leu Glu Cys Ile Gly Glu Ile Phe Gln Gly Leu Asp Ile Leu Lys Asp
        50                  55                  60

Gln Thr Val Arg Gly Gly Thr Val Met Arg Leu Phe Gln Asn Leu Ser
 65                  70                  75                  80

Leu Ile Lys Lys Tyr Ile Asp Arg Gln Glu Lys Lys Cys Gly Glu Glu
                85                  90                  95

Arg Arg Arg Thr Arg Gln Phe Leu Asp Tyr Leu Gln Glu Phe Leu Gly
               100                 105                 110

Ser Met Asn Thr Ala Ala Ile Ile Glu Gly
           115                 120

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P30
      epitope
<221> NAME/KEY: MUTAGEN
<222> LOCATION: (57)..(77)
<223> OTHER INFORMATION: Tetanus toxoid P30 epitope (SEQ ID NO: 24)
<221> NAME/KEY: SIMILAR
<222> LOCATION: (1)..(56)
<223> OTHER INFORMATION: Identical to residues 1-56 in SEQ ID NO: 12
<221> NAME/KEY: SIMILAR
<222> LOCATION: (78)..(128)
<223> OTHER INFORMATION: Identical to residues 63-113 in SEQ ID NO: 12

<400> SEQUENCE: 20

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
                20                  25                  30

Val Pro Thr His Lys Asn His Gln Leu Cys Ile Gly Glu Ile Phe Gln
            35                  40                  45

Gly Leu Asp Ile Leu Lys Asp Gln Phe Asn Asn Phe Thr Val Ser Phe
        50                  55                  60

Trp Leu Arg Val Pro Lys Val Ser Ala Ser His Leu Glu Val Met Arg
 65                  70                  75                  80
```

Leu Phe Gln Asn Leu Ser Leu Ile Lys Lys Tyr Ile Asp Arg Gln Glu
                85                  90                  95

Lys Lys Cys Gly Glu Glu Arg Arg Thr Arg Gln Phe Leu Asp Tyr
        100                 105                 110

Leu Gln Glu Phe Leu Gly Ser Met Asn Thr Ala Ala Ile Ile Glu Gly
        115                 120                 125

<210> SEQ ID NO 21
<211> LENGTH: 130
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P30
      epitope
<221> NAME/KEY: MUTAGEN
<222> LOCATION: (108)..(128)
<223> OTHER INFORMATION: Tetanus toxoid P30 epitope (SEQ ID NO: 24)
<221> NAME/KEY: SIMILAR
<222> LOCATION: (1)..(107)
<223> OTHER INFORMATION: Identical to residues 1-107 in SEQ ID NO: 12
<221> NAME/KEY: SIMILAR
<222> LOCATION: (129)..(130)
<223> OTHER INFORMATION: Identical to residues 112-113 in SEQ ID NO: 12

<400> SEQUENCE: 21

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asp Gln Thr Val Arg Gly Gly Thr Val Met
    50                  55                  60

Arg Leu Phe Gln Asn Leu Ser Leu Ile Lys Lys Tyr Ile Asp Arg Gln
65                  70                  75                  80

Glu Lys Lys Cys Gly Glu Glu Arg Arg Arg Thr Arg Gln Phe Leu Asp
                85                  90                  95

Tyr Leu Gln Glu Phe Leu Gly Ser Met Asn Thr Phe Asn Asn Phe Thr
            100                 105                 110

Val Ser Phe Trp Leu Arg Val Pro Lys Val Ser Ala Ser His Leu Glu
        115                 120                 125

Glu Gly
    130

<210> SEQ ID NO 22
<211> LENGTH: 139
<212> TYPE: PRT
<213> ORGANISM: Artificial Sequence
<220> FEATURE:
<223> OTHER INFORMATION: Description of Artificial Sequence:Murine IL5
      modified by substitution with tetanus toxoid P2
      and P30 epitopes
<221> NAME/KEY: MUTAGEN
<222> LOCATION: (84)..(98)
<223> OTHER INFORMATION: Tetanus toxoid P2 epitope (SEQ ID NO: 23)
<221> NAME/KEY: MUTAGEN
<222> LOCATION: (117)..(137)
<223> OTHER INFORMATION: Tetanus toxoid P30 epitope (SEQ ID NO: 24)
<221> NAME/KEY: SIMILAR
<222> LOCATION: (1)..(83)
<223> OTHER INFORMATION: Identical to residues 1-83 in SEQ ID NO: 12
<221> NAME/KEY: SIMILAR
<222> LOCATION: (99)..(116)
<223> OTHER INFORMATION: Identical to residues 90-109 in SEQ ID NO: 12

```
<221> NAME/KEY: SIMILAR
<222> LOCATION: (138)..(139)
<223> OTHER INFORMATION: Identical to residues 112-113 in SEQ ID NO: 12

<400> SEQUENCE: 22

Met Glu Ile Pro Met Ser Thr Val Val Lys Glu Thr Leu Ala Leu Leu
 1               5                  10                  15

Ser Ala His Arg Ala Leu Leu Thr Ser Asn Glu Thr Met Arg Leu Pro
             20                  25                  30

Val Pro Thr His Lys Asn His Gln Leu Cys Ile Gly Glu Ile Phe Gln
         35                  40                  45

Gly Leu Asp Ile Leu Lys Asp Gln Thr Val Arg Gly Gly Thr Val Met
     50                  55                  60

Arg Leu Phe Gln Asn Leu Ser Leu Ile Lys Lys Tyr Ile Asp Arg Gln
 65                  70                  75                  80

Glu Lys Lys Gln Tyr Ile Lys Ala Asn Ser Lys Phe Ile Gly Ile Thr
                 85                  90                  95

Glu Leu Arg Thr Arg Gln Phe Leu Asp Tyr Leu Gln Glu Phe Leu Gly
            100                 105                 110

Ser Met Asn Thr Phe Asn Asn Phe Thr Val Ser Phe Trp Leu Arg Val
            115                 120                 125

Pro Lys Val Ser Ala Ser His Leu Glu Glu Gly
        130                 135

<210> SEQ ID NO 23
<211> LENGTH: 15
<212> TYPE: PRT
<213> ORGANISM: Clostridium tetani

<400> SEQUENCE: 23

Gln Tyr Ile Lys Ala Asn Ser Lys Phe Ile Gly Ile Thr Glu Leu
 1               5                  10                  15

<210> SEQ ID NO 24
<211> LENGTH: 21
<212> TYPE: PRT
<213> ORGANISM: Clostridium tetani

<400> SEQUENCE: 24

Phe Asn Asn Phe Thr Val Ser Phe Trp Leu Arg Val Pro Lys Val Ser
 1               5                  10                  15

Ala Ser His Leu Glu
             20

<210> SEQ ID NO 25
<211> LENGTH: 45
<212> TYPE: DNA
<213> ORGANISM: Artificial Sequence
<220> FEATURE:
<221> NAME/KEY: CDS
<222> LOCATION: (1)..(45)
<223> OTHER INFORMATION: Description of Artificial sequence: DNA
      encoding His tag

<400> SEQUENCE: 25 atg aaa cac caa cac caa cat caa cat caa cat caa cat caa caa      45
Met Lys His Gln His Gln His Gln His Gln His Gln His Gln Gln
 1               5                  10                  15

<210> SEQ ID NO 26
<211> LENGTH: 15
<212> TYPE: PRT
```

<213> ORGANISM: Artificial Sequence
<220> FEATURE:
<223> OTHER INFORMATION: Artificial Sequence

<400> SEQUENCE: 26

```
Met Lys His Gln His Gln His Gln His Gln His Gln His Gln Gln
 1               5                  10                  15
```

<210> SEQ ID NO 27
<211> LENGTH: 381
<212> TYPE: DNA
<213> ORGANISM: Artificial Sequence
<220> FEATURE:
<223> OTHER INFORMATION: Description of Artificial Sequence: Human Il-5 modified by substitution with tetanus toxoid epitope
<221> NAME/KEY: CDS
<222> LOCATION: (1)..(381)
<221> NAME/KEY: mutation
<222> LOCATION: (262)..(306)
<223> OTHER INFORMATION: Tetanus toxoid P2 epitope
<221> NAME/KEY: misc_feature
<222> LOCATION: (1)..(261)
<223> OTHER INFORMATION: DNA encoding amino acids 1-87 of human IL5
<221> NAME/KEY: misc_feature
<222> LOCATION: (307)..(378)
<223> OTHER INFORMATION: DNA encoding amino acids 92-115 of human IL5

<400> SEQUENCE: 27

```
atc ccc aca gaa att ccc aca agt gca ttg gtg aaa gag acc ttg gca      48
Ile Pro Thr Glu Ile Pro Thr Ser Ala Leu Val Lys Glu Thr Leu Ala
 1               5                  10                  15 ctg ctt tct act cat cga act ctg ctg ata gcc aat gag act ctc cgg      96
Leu Leu Ser Thr His Arg Thr Leu Leu Ile Ala Asn Glu Thr Leu Arg
                20                  25                  30 att cct gtt cct gta cat aaa aat cac caa ctg tgc act gaa gaa atc    144
Ile Pro Val Pro Val His Lys Asn His Gln Leu Cys Thr Glu Glu Ile
         35                  40                  45 ttt cag gga ata ggc aca ctc gag agt caa act gtg caa ggg ggt act    192
Phe Gln Gly Ile Gly Thr Leu Glu Ser Gln Thr Val Gln Gly Gly Thr
 50                  55                  60 gtg gaa aga cta ttc aaa aac ttg tcc tta ata aag aaa tac atc gat    240
Val Glu Arg Leu Phe Lys Asn Leu Ser Leu Ile Lys Lys Tyr Ile Asp
 65                  70                  75                  80 ggc caa aaa aaa aag tgt gga cag tac atc aag gcc aac tcc aag ttc    288
Gly Gln Lys Lys Lys Cys Gly Gln Tyr Ile Lys Ala Asn Ser Lys Phe
                 85                  90                  95 atc ggc atc acc gag ctg aga gta aac caa ttc cta gac tat ctg cag    336
Ile Gly Ile Thr Glu Leu Arg Val Asn Gln Phe Leu Asp Tyr Leu Gln
            100                 105                 110 gag ttt ctt ggt gta atg aac acc gag tgg ata ata gaa agt tga        381
Glu Phe Leu Gly Val Met Asn Thr Glu Trp Ile Ile Glu Ser
        115                 120                 125
```

<210> SEQ ID NO 28
<211> LENGTH: 126
<212> TYPE: PRT
<213> ORGANISM: Artificial Sequence
<220> FEATURE:
<223> OTHER INFORMATION: Description of Artificial Sequence: Human Il-5 modified by substitution with tetanus toxoid epitope

<400> SEQUENCE: 28

```
Ile Pro Thr Glu Ile Pro Thr Ser Ala Leu Val Lys Glu Thr Leu Ala
 1               5                  10                  15
```

```
Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
             35                  40                  45

Phe Gln Gly Ile Gly Thr Leu Glu Ser Gln Thr Val Gln Gly Gly Thr
         50                  55                  60

Val Glu Arg Leu Phe Lys Asn Leu Ser Leu Ile Lys Lys Tyr Ile Asp
 65              70                  75                  80

Gly Gln Lys Lys Lys Cys Gly Gln Tyr Ile Lys Ala Asn Ser Lys Phe
                 85                  90                  95

Ile Gly Ile Thr Glu Leu Arg Val Asn Gln Phe Leu Asp Tyr Leu Gln
            100                 105                 110

Glu Phe Leu Gly Val Met Asn Thr Glu Trp Ile Ile Glu Ser
            115                 120                 125

<210> SEQ ID NO 29
<211> LENGTH: 375
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(375)
<221> NAME/KEY: mutation
<222> LOCATION: (94)..(156)
<223> OTHER INFORMATION: Tetanus toxoid P30 epitope
<221> NAME/KEY: misc_feature
<222> LOCATION: (1)..(93)
<223> OTHER INFORMATION: DNA encoding amino acids 1-31 of human IL5
<221> NAME/KEY: misc_feature
<222> LOCATION: (157)..(372)
<223> OTHER INFORMATION: DNA encoding amino acids 44-115 of human IL5

<400> SEQUENCE: 29 atc ccc aca gaa att ccc aca agt gca ttg gtg aaa gag acc ttg gca        48
Ile Pro Thr Glu Ile Pro Thr Ser Ala Leu Val Lys Glu Thr Leu Ala
 1               5                  10                  15 ctg ctt tct act cat cga act ctg ctg ata gcc aat gag act ctc ttc        96
Leu Leu Ser Thr His Arg Thr Leu Leu Ile Ala Asn Glu Thr Leu Phe
             20                  25                  30 aac aac ttc acc gtg agc ttc tgg ctg cgc gtg cct aag gtg agc gcc       144
Asn Asn Phe Thr Val Ser Phe Trp Leu Arg Val Pro Lys Val Ser Ala
         35                  40                  45 agc cac ctg gag tgc act gaa gaa atc ttt cag gga ata ggc aca ctc       192
Ser His Leu Glu Cys Thr Glu Glu Ile Phe Gln Gly Ile Gly Thr Leu
 50                  55                  60 gag agt caa act gtg caa ggg ggt act gtg gaa aga cta ttc aaa aac       240
Glu Ser Gln Thr Val Gln Gly Gly Thr Val Glu Arg Leu Phe Lys Asn
 65                  70                  75                  80 ttg tcc tta ata aag aaa tac atc gat ggc caa aaa aaa aag tgt gga       288
Leu Ser Leu Ile Lys Lys Tyr Ile Asp Gly Gln Lys Lys Lys Cys Gly
                 85                  90                  95 gaa gaa aga cgg aga gta aac caa ttc cta gac tat ctg cag gag ttt       336
Glu Glu Arg Arg Arg Val Asn Gln Phe Leu Asp Tyr Leu Gln Glu Phe
            100                 105                 110 ctt ggt gta atg aac acc gag tgg ata ata gaa agt tga                   375
Leu Gly Val Met Asn Thr Glu Trp Ile Ile Glu Ser
            115                 120

<210> SEQ ID NO 30
<211> LENGTH: 124
```

```
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 30

Ile Pro Thr Glu Ile Pro Thr Ser Ala Leu Val Lys Glu Thr Leu Ala
  1               5                  10                  15

Leu Leu Ser Thr His Arg Thr Leu Leu Ile Ala Asn Glu Thr Leu Phe
             20                  25                  30

Asn Asn Phe Thr Val Ser Phe Trp Leu Arg Val Pro Lys Val Ser Ala
         35                  40                  45

Ser His Leu Glu Cys Thr Glu Ile Phe Gln Gly Ile Gly Thr Leu
     50                  55                  60

Glu Ser Gln Thr Val Gln Gly Gly Thr Val Glu Arg Leu Phe Lys Asn
 65                  70                  75                  80

Leu Ser Leu Ile Lys Lys Tyr Ile Asp Gly Gln Lys Lys Lys Cys Gly
                 85                  90                  95

Glu Glu Arg Arg Arg Val Asn Gln Phe Leu Asp Tyr Leu Gln Glu Phe
            100                 105                 110

Leu Gly Val Met Asn Thr Glu Trp Ile Ile Glu Ser
        115                 120

<210> SEQ ID NO 31
<211> LENGTH: 393
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(393)
<221> NAME/KEY: mutation
<222> LOCATION: (175)..(237)
<223> OTHER INFORMATION: Tetanus toxoid P30 epitope
<221> NAME/KEY: misc_feature
<222> LOCATION: (1)..(174)
<223> OTHER INFORMATION: DNA encoding amino acids 1-58 of human IL5
<221> NAME/KEY: misc_feature
<222> LOCATION: (238)..(390)
<223> OTHER INFORMATION: DNA encoding amino acids 65-115 of human IL5

<400> SEQUENCE: 31 atc ccc aca gaa att ccc aca agt gca ttg gtg aaa gag acc ttg gca      48
Ile Pro Thr Glu Ile Pro Thr Ser Ala Leu Val Lys Glu Thr Leu Ala
  1               5                  10                  15 ctg ctt tct act cat cga act ctg ctg ata gcc aat gag act ctc cgg     96
Leu Leu Ser Thr His Arg Thr Leu Leu Ile Ala Asn Glu Thr Leu Arg
             20                  25                  30 att cct gtt cct gta cat aaa aat cac caa ctg tgc act gaa gaa atc    144
Ile Pro Val Pro Val His Lys Asn His Gln Leu Cys Thr Glu Glu Ile
         35                  40                  45 ttt cag gga ata ggc aca ctc gag agt caa ttc aac aac ttc acc gtg    192
Phe Gln Gly Ile Gly Thr Leu Glu Ser Gln Phe Asn Asn Phe Thr Val
     50                  55                  60 agc ttc tgg ctg cgc gtg cct aag gtg agc gcc agc cac ctg gag gtg    240
Ser Phe Trp Leu Arg Val Pro Lys Val Ser Ala Ser His Leu Glu Val
 65                  70                  75                  80 gaa aga cta ttc aaa aac ttg tcc tta ata aag aaa tac atc gat ggc    288
Glu Arg Leu Phe Lys Asn Leu Ser Leu Ile Lys Lys Tyr Ile Asp Gly
                 85                  90                  95
```

```
caa aaa aaa aag tgt gga gaa gaa aga cgg aga gta aac caa ttc cta    336
Gln Lys Lys Lys Cys Gly Glu Glu Arg Arg Arg Val Asn Gln Phe Leu
            100                 105                 110 gac tat ctg cag gag ttt ctt ggt gta atg aac acc gag tgg ata ata    384
Asp Tyr Leu Gln Glu Phe Leu Gly Val Met Asn Thr Glu Trp Ile Ile
        115                 120                 125 gaa agt tga                                                         393
Glu Ser
    130
```

<210> SEQ ID NO 32
<211> LENGTH: 130
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 32

```
Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Phe Asn Asn Phe Thr Val
    50                  55                  60

Ser Phe Trp Leu Arg Val Pro Lys Val Ser Ala Ser His Leu Glu Val
65                  70                  75                  80

Glu Arg Leu Phe Lys Asn Leu Ser Leu Ile Lys Lys Tyr Ile Asp Gly
                85                  90                  95

Gln Lys Lys Lys Cys Gly Glu Glu Arg Arg Arg Val Asn Gln Phe Leu
            100                 105                 110

Asp Tyr Leu Gln Glu Phe Leu Gly Val Met Asn Thr Glu Trp Ile Ile
        115                 120                 125

Glu Ser
    130
```

<210> SEQ ID NO 33
<211> LENGTH: 375
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(375)
<221> NAME/KEY: mutation
<222> LOCATION: (175)..(219)
<223> OTHER INFORMATION: Tetanus toxoid P2 epitope
<221> NAME/KEY: misc_feature
<222> LOCATION: (1)..(174)
<223> OTHER INFORMATION: DNA encoding amino acids 1-58 of human IL5
<221> NAME/KEY: misc_feature
<222> LOCATION: (220)..(372)
<223> OTHER INFORMATION: DNA encoding amino acids 65-115 of human IL5

<400> SEQUENCE: 33

```
atc ccc aca gaa att ccc aca agt gca ttg gtg aaa gag acc ttg gca    48
Ile Pro Thr Glu Ile Pro Thr Ser Ala Leu Val Lys Glu Thr Leu Ala
 1               5                  10                  15
```

```
ctg ctt tct act cat cga act ctg ctg ata gcc aat gag act ctc cgg    96
Leu Leu Ser Thr His Arg Thr Leu Leu Ile Ala Asn Glu Thr Leu Arg
            20                  25                  30 att cct gtt cct gta cat aaa aat cac caa ctg tgc act gaa gaa atc   144
Ile Pro Val Pro Val His Lys Asn His Gln Leu Cys Thr Glu Glu Ile
        35                  40                  45 ttt cag gga ata ggc aca ctc gag agt caa cag tac atc aag gcc aac   192
Phe Gln Gly Ile Gly Thr Leu Glu Ser Gln Gln Tyr Ile Lys Ala Asn
    50                  55                  60 tcc aag ttc atc ggc atc acc gag ctg gtg gaa aga cta ttc aaa aac   240
Ser Lys Phe Ile Gly Ile Thr Glu Leu Val Glu Arg Leu Phe Lys Asn
65                  70                  75                  80 ttg tcc tta ata aag aaa tac atc gat ggc caa aaa aag tgt gga        288
Leu Ser Leu Ile Lys Lys Tyr Ile Asp Gly Gln Lys Lys Cys Gly
                85                  90                  95 gaa gaa aga cgg aga gta aac caa ttc cta gac tat ctg cag gag ttt   336
Glu Glu Arg Arg Arg Val Asn Gln Phe Leu Asp Tyr Leu Gln Glu Phe
                100                 105                 110 ctt ggt gta atg aac acc gag tgg ata ata gaa agt tga                375
Leu Gly Val Met Asn Thr Glu Trp Ile Ile Glu Ser
            115                 120
```

<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 34

```
Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Gln Tyr Ile Lys Ala Asn
    50                  55                  60

Ser Lys Phe Ile Gly Ile Thr Glu Leu Val Glu Arg Leu Phe Lys Asn
65                  70                  75                  80

Leu Ser Leu Ile Lys Lys Tyr Ile Asp Gly Gln Lys Lys Cys Gly
                85                  90                  95

Glu Glu Arg Arg Arg Val Asn Gln Phe Leu Asp Tyr Leu Gln Glu Phe
                100                 105                 110

Leu Gly Val Met Asn Thr Glu Trp Ile Ile Glu Ser
            115                 120
```

<210> SEQ ID NO 35
<211> LENGTH: 357
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(357)
<221> NAME/KEY: mutation
<222> LOCATION: (94)..(138)
<223> OTHER INFORMATION: Tetanus toxoid P2 epitope
<221> NAME/KEY: misc_feature

```
<222> LOCATION: (1)..(93)
<223> OTHER INFORMATION: DNA encoding amino acids 1-31 of human IL5
<221> NAME/KEY: misc_feature
<222> LOCATION: (139)..(354)
<223> OTHER INFORMATION: DNA encoding amino acids 44-115 of human IL5

<400> SEQUENCE: 35 atc ccc aca gaa att ccc aca agt gca ttg gtg aaa gag acc ttg gca      48
Ile Pro Thr Glu Ile Pro Thr Ser Ala Leu Val Lys Glu Thr Leu Ala
 1               5                  10                  15 ctg ctt tct act cat cga act ctg ctg ata gcc aat gag act ctc cag      96
Leu Leu Ser Thr His Arg Thr Leu Leu Ile Ala Asn Glu Thr Leu Gln
             20                  25                  30 tac atc aag gcc aac tcc aag ttc atc ggc atc acc gag ctg tgc act     144
Tyr Ile Lys Ala Asn Ser Lys Phe Ile Gly Ile Thr Glu Leu Cys Thr
         35                  40                  45 gaa gaa atc ttt cag gga ata ggc aca ctc gag agt caa act gtg caa     192
Glu Glu Ile Phe Gln Gly Ile Gly Thr Leu Glu Ser Gln Thr Val Gln
     50                  55                  60 ggg ggt act gtg gaa aga cta ttc aaa aac ttg tcc tta ata aag aaa     240
Gly Gly Thr Val Glu Arg Leu Phe Lys Asn Leu Ser Leu Ile Lys Lys
 65                  70                  75                  80 tac atc gat ggc caa aaa aaa aag tgt gga gaa gaa aga cgg aga gta     288
Tyr Ile Asp Gly Gln Lys Lys Lys Cys Gly Glu Glu Arg Arg Arg Val
                 85                  90                  95 aac caa ttc cta gac tat ctg cag gag ttt ctt ggt gta atg aac acc     336
Asn Gln Phe Leu Asp Tyr Leu Gln Glu Phe Leu Gly Val Met Asn Thr
            100                 105                 110 gag tgg ata ata gaa agt tga                                         357
Glu Trp Ile Ile Glu Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 36

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Gln
             20                  25                  30

Tyr Ile Lys Ala Asn Ser Lys Phe Ile Gly Ile Thr Glu Leu Cys Thr
         35                  40                  45

Glu Glu Ile Phe Gln Gly Ile Gly Thr Leu Glu Ser Gln Thr Val Gln
     50                  55                  60

Gly Gly Thr Val Glu Arg Leu Phe Lys Asn Leu Ser Leu Ile Lys Lys
 65                  70                  75                  80

Tyr Ile Asp Gly Gln Lys Lys Lys Cys Gly Glu Glu Arg Arg Arg Val
                 85                  90                  95

Asn Gln Phe Leu Asp Tyr Leu Gln Glu Phe Leu Gly Val Met Asn Thr
            100                 105                 110

Glu Trp Ile Ile Glu Ser
        115

<210> SEQ ID NO 37
<211> LENGTH: 375
```

```
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(375)
<221> NAME/KEY: mutation
<222> LOCATION: (256)..(300)
<223> OTHER INFORMATION: Tetanus toxoid P2 epitope
<221> NAME/KEY: misc_feature
<222> LOCATION: (1)..(255)
<223> OTHER INFORMATION: DNA encoding amino acids 1-85 of human IL5
<221> NAME/KEY: misc_feature
<222> LOCATION: (301)..(372)
<223> OTHER INFORMATION: DNA encoding amino acids 92-115 of human IL5

<400> SEQUENCE: 37
```

| | | | | | | | | | | | | | | | | |
|---|---|---|---|---|---|---|---|---|---|---|---|---|---|---|---|---|
| atc | ccc | aca | gaa | att | ccc | aca | agt | gca | ttg | gtg | aaa | gag | acc | ttg | gca | 48 |
| Ile | Pro | Thr | Glu | Ile | Pro | Thr | Ser | Ala | Leu | Val | Lys | Glu | Thr | Leu | Ala | |
| 1 | | | | 5 | | | | | 10 | | | | | 15 | | |
| ctg | ctt | tct | act | cat | cga | act | ctg | ctg | ata | gcc | aat | gag | act | ctc | cgg | 96 |
| Leu | Leu | Ser | Thr | His | Arg | Thr | Leu | Leu | Ile | Ala | Asn | Glu | Thr | Leu | Arg | |
| | | | 20 | | | | | 25 | | | | | 30 | | | |
| att | cct | gtt | cct | gta | cat | aaa | aat | cac | caa | ctg | tgc | act | gaa | gaa | atc | 144 |
| Ile | Pro | Val | Pro | Val | His | Lys | Asn | His | Gln | Leu | Cys | Thr | Glu | Glu | Ile | |
| | | | 35 | | | | | 40 | | | | | 45 | | | |
| ttt | cag | gga | ata | ggc | aca | ctc | gag | agt | caa | act | gtg | caa | ggg | ggt | act | 192 |
| Phe | Gln | Gly | Ile | Gly | Thr | Leu | Glu | Ser | Gln | Thr | Val | Gln | Gly | Gly | Thr | |
| | 50 | | | | | 55 | | | | | 60 | | | | | |
| gtg | gaa | aga | cta | ttc | aaa | aac | ttg | tcc | tta | ata | aag | aaa | tac | atc | gat | 240 |
| Val | Glu | Arg | Leu | Phe | Lys | Asn | Leu | Ser | Leu | Ile | Lys | Lys | Tyr | Ile | Asp | |
| 65 | | | | | 70 | | | | | 75 | | | | | 80 | |
| ggc | caa | aaa | aaa | aag | cag | tac | atc | aag | gcc | aac | tcc | aag | ttc | atc | ggc | 288 |
| Gly | Gln | Lys | Lys | Lys | Gln | Tyr | Ile | Lys | Ala | Asn | Ser | Lys | Phe | Ile | Gly | |
| | | | | 85 | | | | | 90 | | | | | 95 | | |
| atc | acc | gag | ctg | aga | gta | aac | caa | ttc | cta | gac | tat | ctg | cag | gag | ttt | 336 |
| Ile | Thr | Glu | Leu | Arg | Val | Asn | Gln | Phe | Leu | Asp | Tyr | Leu | Gln | Glu | Phe | |
| | | | 100 | | | | | 105 | | | | | 110 | | | |
| ctt | ggt | gta | atg | aac | acc | gag | tgg | ata | ata | gaa | agt | tga | | | | 375 |
| Leu | Gly | Val | Met | Asn | Thr | Glu | Trp | Ile | Ile | Glu | Ser | | | | | |
| | | | 115 | | | | | 120 | | | | | | | | |

```
<210> SEQ ID NO 38
<211> LENGTH: 124
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 38
```

Ile Pro Thr Glu Ile Pro Thr Ser Ala Leu Val Lys Glu Thr Leu Ala
  1               5                  10                  15

Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
         35                  40                  45

Phe Gln Gly Ile Gly Thr Leu Glu Ser Gln Thr Val Gln Gly Gly Thr
     50                  55                  60

Val Glu Arg Leu Phe Lys Asn Leu Ser Leu Ile Lys Lys Tyr Ile Asp
 65                  70                  75                  80

```
Gly Gln Lys Lys Lys Gln Tyr Ile Lys Ala Asn Ser Lys Phe Ile Gly
                85                  90                  95

Ile Thr Glu Leu Arg Val Asn Gln Phe Leu Asp Tyr Leu Gln Glu Phe
            100                 105                 110

Leu Gly Val Met Asn Thr Glu Trp Ile Ile Glu Ser
        115                 120
```

<210> SEQ ID NO 39
<211> LENGTH: 399
<212> TYPE: DNA
<213> ORGANISM: Artificial Sequence
<220> FEATURE:
<223> OTHER INFORMATION: Description of Artificial Sequence: Human Il-5 modified by substitution with tetanus toxoid epitope
<221> NAME/KEY: CDS
<222> LOCATION: (1)..(399)
<221> NAME/KEY: mutation
<222> LOCATION: (262)..(324)
<223> OTHER INFORMATION: Tetanus toxoid P30 epitope
<221> NAME/KEY: misc_feature
<222> LOCATION: (1)..(261)
<223> OTHER INFORMATION: DNA encoding amino acids 1-87 of human IL5
<221> NAME/KEY: misc_feature
<222> LOCATION: (325)..(396)
<223> OTHER INFORMATION: DNA encoding amino acids 92-115 of human IL5

<400> SEQUENCE: 39

```
atc ccc aca gaa att ccc aca agt gca ttg gtg aaa gag acc ttg gca      48
Ile Pro Thr Glu Ile Pro Thr Ser Ala Leu Val Lys Glu Thr Leu Ala
 1               5                  10                  15 ctg ctt tct act cat cga act ctg ctg ata gcc aat gag act ctc cgg     96
Leu Leu Ser Thr His Arg Thr Leu Leu Ile Ala Asn Glu Thr Leu Arg
            20                  25                  30 att cct gtt cct gta cat aaa aat cac caa ctg tgc act gaa gaa atc    144
Ile Pro Val Pro Val His Lys Asn His Gln Leu Cys Thr Glu Glu Ile
        35                  40                  45 ttt cag gga ata ggc aca ctc gag agt caa act gtg caa ggg ggt act    192
Phe Gln Gly Ile Gly Thr Leu Glu Ser Gln Thr Val Gln Gly Gly Thr
    50                  55                  60 gtg gaa aga cta ttc aaa aac ttg tcc tta ata aag aaa tac atc gat    240
Val Glu Arg Leu Phe Lys Asn Leu Ser Leu Ile Lys Lys Tyr Ile Asp
65                  70                  75                  80 ggc caa aaa aaa aag tgt gga ttc aac aac ttc acc gtg agc ttc tgg    288
Gly Gln Lys Lys Lys Cys Gly Phe Asn Asn Phe Thr Val Ser Phe Trp
                85                  90                  95 ctg cgc gtg cct aag gtg agc gcc agc cac ctg gag aga gta aac caa    336
Leu Arg Val Pro Lys Val Ser Ala Ser His Leu Glu Arg Val Asn Gln
            100                 105                 110 ttc cta gac tat ctg cag gag ttt ctt ggt gta atg aac acc gag tgg    384
Phe Leu Asp Tyr Leu Gln Glu Phe Leu Gly Val Met Asn Thr Glu Trp
        115                 120                 125 ata ata gaa agt tga                                                 399
Ile Ile Glu Ser
        130
```

<210> SEQ ID NO 40
<211> LENGTH: 132
<212> TYPE: PRT
<213> ORGANISM: Artificial Sequence
<220> FEATURE:
<223> OTHER INFORMATION: Description of Artificial Sequence: Human Il-5 modified by substitution with tetanus toxoid epitope

<400> SEQUENCE: 40

```
Ile Pro Thr Glu Ile Pro Thr Ser Ala Leu Val Lys Glu Thr Leu Ala
  1               5                  10                  15

Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
         35                  40                  45

Phe Gln Gly Ile Gly Thr Leu Glu Ser Gln Thr Val Gln Gly Gly Thr
     50                  55                  60

Val Glu Arg Leu Phe Lys Asn Leu Ser Leu Ile Lys Lys Tyr Ile Asp
 65              70                  75                  80

Gly Gln Lys Lys Lys Cys Gly Phe Asn Asn Phe Thr Val Ser Phe Trp
                 85                  90                  95

Leu Arg Val Pro Lys Val Ser Ala Ser His Leu Glu Arg Val Asn Gln
                100                 105                 110

Phe Leu Asp Tyr Leu Gln Glu Phe Leu Gly Val Met Asn Thr Glu Trp
            115                 120                 125

Ile Ile Glu Ser
        130
```

```
<210> SEQ ID NO 41
<211> LENGTH: 393
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitope
<221> NAME/KEY: CDS
<222> LOCATION: (1)..(393)
<221> NAME/KEY: mutation
<222> LOCATION: (256)..(318)
<223> OTHER INFORMATION: Tetanus toxoid P30 epitope
<221> NAME/KEY: misc_feature
<222> LOCATION: (1)..(255)
<223> OTHER INFORMATION: DNA encoding amino acids 1-85 of human IL5
<221> NAME/KEY: misc_feature
<222> LOCATION: (319)..(390)
<223> OTHER INFORMATION: DNA encoding amino acids 92-115 of human IL5

<400> SEQUENCE: 41
```

```
atc ccc aca gaa att ccc aca agt gca ttg gtg aaa gag acc ttg gca      48
Ile Pro Thr Glu Ile Pro Thr Ser Ala Leu Val Lys Glu Thr Leu Ala
  1               5                  10                  15 ctg ctt tct act cat cga act ctg ctg ata gcc aat gag act ctc cgg     96
Leu Leu Ser Thr His Arg Thr Leu Leu Ile Ala Asn Glu Thr Leu Arg
             20                  25                  30 att cct gtt cct gta cat aaa aat cac caa ctg tgc act gaa gaa atc    144
Ile Pro Val Pro Val His Lys Asn His Gln Leu Cys Thr Glu Glu Ile
         35                  40                  45 ttt cag gga ata ggc aca ctc gag agt caa act gtg caa ggg ggt act    192
Phe Gln Gly Ile Gly Thr Leu Glu Ser Gln Thr Val Gln Gly Gly Thr
     50                  55                  60 gtg gaa aga cta ttc aaa aac ttg tcc tta ata aag aaa tac atc gat    240
Val Glu Arg Leu Phe Lys Asn Leu Ser Leu Ile Lys Lys Tyr Ile Asp
 65              70                  75                  80 ggc caa aaa aag aag ttc aac aac ttc acc gtg agc ttc tgg ctg cgc    288
Gly Gln Lys Lys Lys Phe Asn Asn Phe Thr Val Ser Phe Trp Leu Arg
                 85                  90                  95 gtg cct aag gtg agc gcc agc cac ctg gag aga gta aac caa ttc cta    336
Val Pro Lys Val Ser Ala Ser His Leu Glu Arg Val Asn Gln Phe Leu
                100                 105                 110
```

-continued

```
gac tat ctg cag gag ttt ctt ggt gta atg aac acc gag tgg ata ata      384
Asp Tyr Leu Gln Glu Phe Leu Gly Val Met Asn Thr Glu Trp Ile Ile
        115                 120                 125 gaa agt tga                                                           393
Glu Ser
    130
```

<210> SEQ ID NO 42
<211> LENGTH: 130
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitope

<400> SEQUENCE: 42

```
Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Phe Asn Asn Phe Thr Val Ser Phe Trp Leu Arg
                85                  90                  95

Val Pro Lys Val Ser Ala Ser His Leu Glu Arg Val Asn Gln Phe Leu
            100                 105                 110

Asp Tyr Leu Gln Glu Phe Leu Gly Val Met Asn Thr Glu Trp Ile Ile
        115                 120                 125

Glu Ser
    130
```

<210> SEQ ID NO 43
<211> LENGTH: 444
<212> TYPE: DNA
<213> ORGANISM: Artificial Sequence
<220> FEATURE:
<223> OTHER INFORMATION: Description of Artificial Sequence: Human Il-5
      modified by substitution with tetanus toxoid
      epitopes
<221> NAME/KEY: CDS
<222> LOCATION: (1)..(444)
<221> NAME/KEY: mutation
<222> LOCATION: (262)..(306)
<223> OTHER INFORMATION: Tetanus toxoid P2 epitope
<221> NAME/KEY: mutation
<222> LOCATION: (307)..(369)
<223> OTHER INFORMATION: Tetanus toxoid P30 epitope
<221> NAME/KEY: misc_feature
<222> LOCATION: (1)..(261)
<223> OTHER INFORMATION: DNA encoding amino acids 1-87 of human IL5
<221> NAME/KEY: misc_feature
<222> LOCATION: (370)..(441)
<223> OTHER INFORMATION: DNA encoding amino acids 92-115 of human IL5

<400> SEQUENCE: 43

```
atc ccc aca gaa att ccc aca agt gca ttg gtg aaa gag acc ttg gca       48
Ile Pro Thr Glu Ile Pro Thr Ser Ala Leu Val Lys Glu Thr Leu Ala
 1               5                  10                  15 ctg ctt tct act cat cga act ctg ctg ata gcc aat gag act ctc cgg      96
Leu Leu Ser Thr His Arg Thr Leu Leu Ile Ala Asn Glu Thr Leu Arg
```

```
                    20                  25                  30
att cct gtt cct gta cat aaa aat cac caa ctg tgc act gaa gaa atc      144
Ile Pro Val Pro Val His Lys Asn His Gln Leu Cys Thr Glu Glu Ile
            35                  40                  45 ttt cag gga ata ggc aca ctc gag agt caa act gtg caa ggg ggt act      192
Phe Gln Gly Ile Gly Thr Leu Glu Ser Gln Thr Val Gln Gly Gly Thr
        50                  55                  60 gtg gaa aga cta ttc aaa aac ttg tcc tta ata aag aaa tac atc gat      240
Val Glu Arg Leu Phe Lys Asn Leu Ser Leu Ile Lys Lys Tyr Ile Asp
 65                 70                  75                  80 ggc caa aaa aaa aag tgt gga cag tac atc aag gcc aac tcc aag ttc      288
Gly Gln Lys Lys Lys Cys Gly Gln Tyr Ile Lys Ala Asn Ser Lys Phe
                85                  90                  95 atc ggc atc acc gag ctg ttc aac aac ttc acc gtg agc ttc tgg ctg      336
Ile Gly Ile Thr Glu Leu Phe Asn Asn Phe Thr Val Ser Phe Trp Leu
            100                 105                 110 cgc gtg cct aag gtg agc gcc agc cac ctg gag aga gta aac caa ttc      384
Arg Val Pro Lys Val Ser Ala Ser His Leu Glu Arg Val Asn Gln Phe
        115                 120                 125 cta gac tat ctg cag gag ttt ctt ggt gta atg aac acc gag tgg ata      432
Leu Asp Tyr Leu Gln Glu Phe Leu Gly Val Met Asn Thr Glu Trp Ile
    130                 135                 140 ata gaa agt tga                                                      444
Ile Glu Ser
145

<210> SEQ ID NO 44
<211> LENGTH: 147
<212> TYPE: PRT
<213> ORGANISM: Artificial Sequence
<220> FEATURE:
<223> OTHER INFORMATION: Description of Artificial Sequence: Human Il-5
      modified by substitution with tetanus toxoid
      epitopes

<400> SEQUENCE: 44

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
 65                 70                  75                  80

Gly Gln Lys Lys Lys Cys Gly Gln Tyr Ile Lys Ala Asn Ser Lys Phe
                85                  90                  95

Ile Gly Ile Thr Glu Leu Phe Asn Asn Phe Thr Val Ser Phe Trp Leu
            100                 105                 110

Arg Val Pro Lys Val Ser Ala Ser His Leu Glu Arg Val Asn Gln Phe
        115                 120                 125

Leu Asp Tyr Leu Gln Glu Phe Leu Gly Val Met Asn Thr Glu Trp Ile
    130                 135                 140

Ile Glu Ser
145

<210> SEQ ID NO 45
<211> LENGTH: 375
```

```
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(375)
<221> NAME/KEY: mutation
<222> LOCATION: (256)..(300)
<223> OTHER INFORMATION: Tetanus toxoid P2 epitope
<221> NAME/KEY: misc_feature
<222> LOCATION: (1)..(255)
<223> OTHER INFORMATION: DNA encoding amino acids 1-85 in murine IL5
<221> NAME/KEY: misc_feature
<222> LOCATION: (301)..(375)
<223> OTHER INFORMATION: DNA encoding amino acids 90-113 of murine IL5

<400> SEQUENCE: 45 atg gag att ccc atg agc aca gtg gtg aaa gag acc ttg aca cag ctg        48
Met Glu Ile Pro Met Ser Thr Val Val Lys Glu Thr Leu Thr Gln Leu
 1               5                  10                  15 tcc gct cac cga gct ctg ttg aca agc aat gag acg atg agg ctt cct        96
Ser Ala His Arg Ala Leu Leu Thr Ser Asn Glu Thr Met Arg Leu Pro
             20                  25                  30 gtc cct act cat aaa aat cac cag cta tgc att gga gag atc ttt cag       144
Val Pro Thr His Lys Asn His Gln Leu Cys Ile Gly Glu Ile Phe Gln
         35                  40                  45 ggg cta gac ata ctg aag aat caa act gtc cgt ggg ggt acc gtg gaa       192
Gly Leu Asp Ile Leu Lys Asn Gln Thr Val Arg Gly Gly Thr Val Glu
     50                  55                  60 atg cta ttc caa aac ctg tca tta ata aag aaa tac atc gat aga caa       240
Met Leu Phe Gln Asn Leu Ser Leu Ile Lys Lys Tyr Ile Asp Arg Gln
 65                  70                  75                  80 aaa gag aag tgt ggc cag tac atc aaa gct aac tcc aaa ttc atc ggt       288
Lys Glu Lys Cys Gly Gln Tyr Ile Lys Ala Asn Ser Lys Phe Ile Gly
                 85                  90                  95 atc acc gag ctg agg acg agg cag ttc ctg gat tat ctg cag gag ttc       336
Ile Thr Glu Leu Arg Thr Arg Gln Phe Leu Asp Tyr Leu Gln Glu Phe
            100                 105                 110 ctt ggt gtg atg agt aca gag tgg gca atg gaa ggc taa                   375
Leu Gly Val Met Ser Thr Glu Trp Ala Met Glu Gly
        115                 120

<210> SEQ ID NO 46
<211> LENGTH: 124
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 46

Met Glu Ile Pro Met Ser Thr Val Val Lys Glu Thr Leu Thr Gln Leu
 1               5                  10                  15

Ser Ala His Arg Ala Leu Leu Thr Ser Asn Glu Thr Met Arg Leu Pro
             20                  25                  30

Val Pro Thr His Lys Asn His Gln Leu Cys Ile Gly Glu Ile Phe Gln
         35                  40                  45

Gly Leu Asp Ile Leu Lys Asn Gln Thr Val Arg Gly Gly Thr Val Glu
     50                  55                  60

Met Leu Phe Gln Asn Leu Ser Leu Ile Lys Lys Tyr Ile Asp Arg Gln
 65                  70                  75                  80
```

```
Lys Glu Lys Cys Gly Gln Tyr Ile Lys Ala Asn Ser Lys Phe Ile Gly
            85                  90                  95

Ile Thr Glu Leu Arg Thr Arg Gln Phe Leu Asp Tyr Leu Gln Glu Phe
            100                 105                 110

Leu Gly Val Met Ser Thr Glu Trp Ala Met Glu Gly
            115                 120

<210> SEQ ID NO 47
<211> LENGTH: 369
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(369)
<221> NAME/KEY: mutation
<222> LOCATION: (88)..(150)
<223> OTHER INFORMATION: Tetanus toxoid P30 epitope
<221> NAME/KEY: misc_feature
<222> LOCATION: (1)..(87)
<223> OTHER INFORMATION: DNA encoding amino acids 1-29 of murine IL5
<221> NAME/KEY: misc_feature
<222> LOCATION: (151)..(366)
<223> OTHER INFORMATION: DNA encoding amino acids 42-113 of murine IL5

<400> SEQUENCE: 47 atg gag att ccc atg agc aca gtg gtg aaa gag acc ttg aca cag ctg      48
Met Glu Ile Pro Met Ser Thr Val Val Lys Glu Thr Leu Thr Gln Leu
 1               5                  10                  15 tcc gct cac cga gct ctg ttg aca agc aat gag acg atg ttc aac aac      96
Ser Ala His Arg Ala Leu Leu Thr Ser Asn Glu Thr Met Phe Asn Asn
                20                  25                  30 ttc acc gtg agc ttc tgg ctg cgc gtg ccc aag gtg agc gcc agc cac     144
Phe Thr Val Ser Phe Trp Leu Arg Val Pro Lys Val Ser Ala Ser His
            35                  40                  45 ctg gag tgc att gga gag atc ttt cag ggg cta gac ata ctg aag aat     192
Leu Glu Cys Ile Gly Glu Ile Phe Gln Gly Leu Asp Ile Leu Lys Asn
        50                  55                  60 caa act gtc cgt ggg ggt acc gtg gaa atg cta ttc caa aac ctg tca     240
Gln Thr Val Arg Gly Gly Thr Val Glu Met Leu Phe Gln Asn Leu Ser
 65                 70                  75                  80 tta ata aag aaa tac atc gat aga caa aaa gag aag tgt ggc gag gag     288
Leu Ile Lys Lys Tyr Ile Asp Arg Gln Lys Glu Lys Cys Gly Glu Glu
                85                  90                  95 aga cgg agg acg agg cag ttc ctg gat tat ctg cag gag ttc ctt ggt     336
Arg Arg Arg Thr Arg Gln Phe Leu Asp Tyr Leu Gln Glu Phe Leu Gly
            100                 105                 110 gtg atg agt aca gag tgg gca atg gaa ggc taa                         369
Val Met Ser Thr Glu Trp Ala Met Glu Gly
            115                 120

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 48

Met Glu Ile Pro Met Ser Thr Val Val Lys Glu Thr Leu Thr Gln Leu
 1               5                  10                  15
```

```
Ser Ala His Arg Ala Leu Leu Thr Ser Asn Glu Thr Met Phe Asn Asn
             20                  25                  30

Phe Thr Val Ser Phe Trp Leu Arg Val Pro Lys Val Ser Ala Ser His
         35                  40                  45

Leu Glu Cys Ile Gly Glu Ile Phe Gln Gly Leu Asp Ile Leu Lys Asn
     50                  55                  60

Gln Thr Val Arg Gly Gly Thr Val Glu Met Leu Phe Gln Asn Leu Ser
 65                  70                  75                  80

Leu Ile Lys Lys Tyr Ile Asp Arg Gln Lys Glu Lys Cys Gly Glu Glu
                 85                  90                  95

Arg Arg Arg Thr Arg Gln Phe Leu Asp Tyr Leu Gln Glu Phe Leu Gly
            100                 105                 110

Val Met Ser Thr Glu Trp Ala Met Glu Gly
        115                 120
```

<210> SEQ ID NO 49
<211> LENGTH: 387
<212> TYPE: DNA
<213> ORGANISM: Artificial Sequence
<220> FEATURE:
<223> OTHER INFORMATION: Description of Artificial Sequence: Murine Il-5
    modified by substitution with tetanus toxoid
    epitope
<221> NAME/KEY: CDS
<222> LOCATION: (1)..(387)
<221> NAME/KEY: mutation
<222> LOCATION: (169)..(231)
<223> OTHER INFORMATION: Tetanus toxoid P2 epitope
<221> NAME/KEY: misc_feature
<222> LOCATION: (1)..(168)
<223> OTHER INFORMATION: DNA encoding amino acids 1-56 of murine IL5
<221> NAME/KEY: misc_feature
<222> LOCATION: (232)..(384)
<223> OTHER INFORMATION: DNA encoding amino acids 63-113 of murine IL5

<400> SEQUENCE: 49

```
atg gag att ccc atg agc aca gtg gtg aaa gag acc ttg aca cag ctg     48
Met Glu Ile Pro Met Ser Thr Val Val Lys Glu Thr Leu Thr Gln Leu
  1               5                  10                  15 tcc gct cac cga gct ctg ttg aca agc aat gag acg atg agg ctt cct     96
Ser Ala His Arg Ala Leu Leu Thr Ser Asn Glu Thr Met Arg Leu Pro
             20                  25                  30 gtc cct act cat aaa aat cac cag cta tgc att gga gag atc ttt cag    144
Val Pro Thr His Lys Asn His Gln Leu Cys Ile Gly Glu Ile Phe Gln
         35                  40                  45 ggg cta gac ata ctg aag aat caa ttc aac aac ttc acc gtg agc ttc    192
Gly Leu Asp Ile Leu Lys Asn Gln Phe Asn Asn Phe Thr Val Ser Phe
     50                  55                  60 tgg ctg cgc gtg ccc aag gtg agc gcc agc cac ctg gag gtg gaa atg    240
Trp Leu Arg Val Pro Lys Val Ser Ala Ser His Leu Glu Val Glu Met
 65                  70                  75                  80 cta ttc caa aac ctg tca tta ata aag aaa tac atc gat aga caa aaa    288
Leu Phe Gln Asn Leu Ser Leu Ile Lys Lys Tyr Ile Asp Arg Gln Lys
                 85                  90                  95 gag aag tgt ggc gag gag aga cgg agg acg agg cag ttc ctg gat tat    336
Glu Lys Cys Gly Glu Glu Arg Arg Arg Thr Arg Gln Phe Leu Asp Tyr
            100                 105                 110 ctg cag gag ttc ctt ggt gtg atg agt aca gag tgg gca atg gaa ggc    384
Leu Gln Glu Phe Leu Gly Val Met Ser Thr Glu Trp Ala Met Glu Gly
        115                 120                 125 taa                                                                387
```

-continued

```
<210> SEQ ID NO 50
<211> LENGTH: 128
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 50

Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Phe Asn Asn Phe Thr Val Ser Phe
    50                  55                  60

Trp Leu Arg Val Pro Lys Val Ser Ala Ser His Leu Glu Val Glu Met
65                  70                  75                  80

Leu Phe Gln Asn Leu Ser Leu Ile Lys Lys Tyr Ile Asp Arg Gln Lys
                85                  90                  95

Glu Lys Cys Gly Glu Glu Arg Arg Thr Arg Gln Phe Leu Asp Tyr
            100                 105                 110

Leu Gln Glu Phe Leu Gly Val Met Ser Thr Glu Trp Ala Met Glu Gly
        115                 120                 125

<210> SEQ ID NO 51
<211> LENGTH: 351
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(351)
<221> NAME/KEY: mutation
<222> LOCATION: (88)..(132)
<223> OTHER INFORMATION: Tetanus toxoid P2 epitope
<221> NAME/KEY: misc_feature
<222> LOCATION: (1)..(87)
<223> OTHER INFORMATION: DNA encoding amino acids 1-29 of murine IL5
<221> NAME/KEY: misc_feature
<222> LOCATION: (133)..(348)
<223> OTHER INFORMATION: DNA encoding amino acids 42-113 of murine IL5

<400> SEQUENCE: 51 atg gag att ccc atg agc aca gtg gtg aaa gag acc ttg aca cag ctg      48
Met Glu Ile Pro Met Ser Thr Val Val Lys Glu Thr Leu Thr Gln Leu
1               5                   10                  15 tcc gct cac cga gct ctg ttg aca agc aat gag acg atg cag tac atc      96
Ser Ala His Arg Ala Leu Leu Thr Ser Asn Glu Thr Met Gln Tyr Ile
            20                  25                  30 aaa gct aac tcc aaa ttc atc ggt atc acc gag ctg tgc att gga gag     144
Lys Ala Asn Ser Lys Phe Ile Gly Ile Thr Glu Leu Cys Ile Gly Glu
        35                  40                  45 atc ttt cag ggg cta gac ata ctg aag aat caa act gtc cgt ggg ggt     192
Ile Phe Gln Gly Leu Asp Ile Leu Lys Asn Gln Thr Val Arg Gly Gly
    50                  55                  60 acc gtg gaa atg cta ttc caa aac ctg tca tta ata aag aaa tac atc     240
Thr Val Glu Met Leu Phe Gln Asn Leu Ser Leu Ile Lys Lys Tyr Ile
65                  70                  75                  80 gat aga caa aaa gag aag tgt ggc gag gag aga cgg agg acg agg cag     288
```

```
                Asp Arg Gln Lys Glu Lys Cys Gly Glu Glu Arg Arg Thr Arg Gln
                                85                  90                  95 ttc ctg gat tat ctg cag gag ttc ctt ggt gtg atg agt aca gag tgg              336
Phe Leu Asp Tyr Leu Gln Glu Phe Leu Gly Val Met Ser Thr Glu Trp
            100                 105                 110 gca atg gaa ggc taa                                                          351
Ala Met Glu Gly
        115

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 52

Met Glu Ile Pro Met Ser Thr Val Val Lys Glu Thr Leu Thr Gln Leu
 1               5                  10                  15

Ser Ala His Arg Ala Leu Leu Thr Ser Asn Glu Thr Met Gln Tyr Ile
            20                  25                  30

Lys Ala Asn Ser Lys Phe Ile Gly Ile Thr Glu Leu Cys Ile Gly Glu
        35                  40                  45

Ile Phe Gln Gly Leu Asp Ile Leu Lys Asn Gln Thr Val Arg Gly Gly
    50                  55                  60

Thr Val Glu Met Leu Phe Gln Asn Leu Ser Leu Ile Lys Lys Tyr Ile
65                  70                  75                  80

Asp Arg Gln Lys Glu Lys Cys Gly Glu Glu Arg Arg Arg Thr Arg Gln
                85                  90                  95

Phe Leu Asp Tyr Leu Gln Glu Phe Leu Gly Val Met Ser Thr Glu Trp
            100                 105                 110

Ala Met Glu Gly
        115

<210> SEQ ID NO 53
<211> LENGTH: 369
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(369)
<221> NAME/KEY: mutation
<222> LOCATION: (250)..(294)
<223> OTHER INFORMATION: Tetanus toxoid P2 epitope
<221> NAME/KEY: misc_feature
<222> LOCATION: (1)..(249)
<223> OTHER INFORMATION: DNA encoding amino acids 1-83 of murine IL5
<221> NAME/KEY: misc_feature
<222> LOCATION: (295)..(366)
<223> OTHER INFORMATION: DNA encoding amino acids 90-113 of murine IL5

<400> SEQUENCE: 53 atg gag att ccc atg agc aca gtg gtg aaa gag acc ttg aca cag ctg              48
Met Glu Ile Pro Met Ser Thr Val Val Lys Glu Thr Leu Thr Gln Leu
 1               5                  10                  15 tcc gct cac cga gct ctg ttg aca agc aat gag acg atg agg ctt cct              96
Ser Ala His Arg Ala Leu Leu Thr Ser Asn Glu Thr Met Arg Leu Pro
            20                  25                  30 gtc cct act cat aaa aat cac cag cta tgc att gga gag atc ttt cag             144
```

```
Val Pro Thr His Lys Asn His Gln Leu Cys Ile Gly Glu Ile Phe Gln
        35                  40                  45 ggg cta gac ata ctg aag aat caa act gtc cgt ggg ggt acc gtg gaa     192
Gly Leu Asp Ile Leu Lys Asn Gln Thr Val Arg Gly Gly Thr Val Glu
 50                  55                  60 atg cta ttc caa aac ctg tca tta ata aag aaa tac atc gat aga caa     240
Met Leu Phe Gln Asn Leu Ser Leu Ile Lys Lys Tyr Ile Asp Arg Gln
 65                  70                  75                  80 aaa gag aag cag tac atc aag gcc aac tcc aag ttc atc ggc atc acc     288
Lys Glu Lys Gln Tyr Ile Lys Ala Asn Ser Lys Phe Ile Gly Ile Thr
                 85                  90                  95 gag ctg agg acg agg cag ttc ctg gat tat ctg cag gag ttc ctt ggt     336
Glu Leu Arg Thr Arg Gln Phe Leu Asp Tyr Leu Gln Glu Phe Leu Gly
                100                 105                 110 gtg atg agt aca gag tgg gca atg gaa ggc taa                         369
Val Met Ser Thr Glu Trp Ala Met Glu Gly
        115                 120
```

<210> SEQ ID NO 54
<211> LENGTH: 122
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 54

```
Met Glu Ile Pro Met Ser Thr Val Val Lys Glu Thr Leu Thr Gln Leu
  1               5                  10                  15

Ser Ala His Arg Ala Leu Leu Thr Ser Asn Glu Thr Met Arg Leu Pro
                 20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Gly Thr Val Glu
 50                  55                  60

Met Leu Phe Gln Asn Leu Ser Leu Ile Lys Lys Tyr Ile Asp Arg Gln
 65                  70                  75                  80

Lys Glu Lys Gln Tyr Ile Lys Ala Asn Ser Lys Phe Ile Gly Ile Thr
                 85                  90                  95

Glu Leu Arg Thr Arg Gln Phe Leu Asp Tyr Leu Gln Glu Phe Leu Gly
                100                 105                 110

Val Met Ser Thr Glu Trp Ala Met Glu Gly
        115                 120
```

<210> SEQ ID NO 55
<211> LENGTH: 393
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(393)
<221> NAME/KEY: mutation
<222> LOCATION: (256)..(318)
<223> OTHER INFORMATION: Tetanus toxoid P30 epitope
<221> NAME/KEY: misc_feature
<222> LOCATION: (1)..(255)
<223> OTHER INFORMATION: DNA encoding amino acids 1-85 of murine IL5
<221> NAME/KEY: misc_feature
<222> LOCATION: (319)..(390)
<223> OTHER INFORMATION: DNA encoding amino acids 90-113 of murine IL5

```
<400> SEQUENCE: 55 atg gag att ccc atg agc aca gtg gtg aaa gag acc ttg aca cag ctg      48
Met Glu Ile Pro Met Ser Thr Val Val Lys Glu Thr Leu Thr Gln Leu
  1               5                  10                  15 tcc gct cac cga gct ctg ttg aca agc aat gag acg atg agg ctt cct      96
Ser Ala His Arg Ala Leu Leu Thr Ser Asn Glu Thr Met Arg Leu Pro
             20                  25                  30 gtc cct act cat aaa aat cac cag cta tgc att gga gag atc ttt cag     144
Val Pro Thr His Lys Asn His Gln Leu Cys Ile Gly Glu Ile Phe Gln
         35                  40                  45 ggg cta gac ata ctg aag aat caa act gtc cgt ggg ggt acc gtg gaa     192
Gly Leu Asp Ile Leu Lys Asn Gln Thr Val Arg Gly Gly Thr Val Glu
     50                  55                  60 atg cta ttc caa aac ctg tca tta ata aag aaa tac atc gat aga caa     240
Met Leu Phe Gln Asn Leu Ser Leu Ile Lys Lys Tyr Ile Asp Arg Gln
 65                  70                  75                  80 aaa gag aag tgt ggc ttc aac aac ttc acc gtg agc ttc tgg ctg cgc     288
Lys Glu Lys Cys Gly Phe Asn Asn Phe Thr Val Ser Phe Trp Leu Arg
                 85                  90                  95 gtg ccc aag gtg agc gcc agc cac ctg gag agg acg agg cag ttc ctg     336
Val Pro Lys Val Ser Ala Ser His Leu Glu Arg Thr Arg Gln Phe Leu
            100                 105                 110 gat tat ctg cag gag ttc ctt ggt gtg atg agt aca gag tgg gca atg     384
Asp Tyr Leu Gln Glu Phe Leu Gly Val Met Ser Thr Glu Trp Ala Met
        115                 120                 125 gaa ggc taa                                                         393
Glu Gly
    130

<210> SEQ ID NO 56
<211> LENGTH: 130
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 56

Met

```
<210> SEQ ID NO 57
<211> LENGTH: 387
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitope
<221> NAME/KEY: CDS
<222> LOCATION: (1)..(387)
<221> NAME/KEY: mutation
<222> LOCATION: (250)..(312)
<223> OTHER INFORMATION: Tetanus toxoid P30 epitope
<221> NAME/KEY: misc_feature
<222> LOCATION: (1)..(249)
<223> OTHER INFORMATION: DNA encoding amino acids 1-83 of murine IL5
<221> NAME/KEY: misc_feature
<222> LOCATION: (313)..(384)
<223> OTHER INFORMATION: DNA encoding amino acids 90-113 of murine IL5

<400> SEQUENCE: 57 atg gag att ccc atg agc aca gtg gtg aaa gag acc ttg aca cag ctg      48
Met Glu Ile Pro Met Ser Thr Val Val Lys Glu Thr Leu Thr Gln Leu
 1               5                  10                  15 tcc gct cac cga gct ctg ttg aca agc aat gag acg atg agg ctt cct      96
Ser Ala His Arg Ala Leu Leu Thr Ser Asn Glu Thr Met Arg Leu Pro
             20                  25                  30 gtc cct act cat aaa aat cac cag cta tgc att gga gag atc ttt cag     144
Val Pro Thr His Lys Asn His Gln Leu Cys Ile Gly Glu Ile Phe Gln
         35                  40                  45 ggg cta gac ata ctg aag aat caa act gtc cgt ggg ggt acc gtg gaa     192
Gly Leu Asp Ile Leu Lys Asn Gln Thr Val Arg Gly Gly Thr Val Glu
     50                  55                  60 atg cta ttc caa aac ctg tca tta ata aag aaa tac atc gat aga caa     240
Met Leu Phe Gln Asn Leu Ser Leu Ile Lys Lys Tyr Ile Asp Arg Gln
 65                  70                  75                  80 aaa gag aag ttc aac aac ttc acc gtg agc ttc tgg ctg cgc gtg ccc     288
Lys Glu Lys Phe Asn Asn Phe Thr Val Ser Phe Trp Leu Arg Val Pro
                 85                  90                  95 aag gtg agc gcc agc cac ctg gag agg acg agg cag ttc ctg gat tat     336
Lys Val Ser Ala Ser His Leu Glu Arg Thr Arg Gln Phe Leu Asp Tyr
            100                 105                 110 ctg cag gag ttc ctt ggt gtg atg agt aca gag tgg gca atg gaa ggc     384
Leu Gln Glu Phe Leu Gly Val Met Ser Thr Glu Trp Ala Met Glu Gly
        115                 120                 125 taa                                                                 387

<210> SEQ ID NO 58
<211> LENGTH: 128
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitope

<400> SEQUENCE: 58

Met Glu Ile Pro Met Ser Thr Val Val Lys Glu Thr Leu Thr Gln Leu
 1               5                  10                  15

Ser Ala His Arg Ala Leu Leu Thr Ser Asn Glu Thr Met Arg Leu Pro
             20                  25                  30

Val Pro Thr His Lys Asn His Gln Leu Cys Ile Gly Glu Ile Phe Gln
         35                  40                  45

Gly Leu Asp Ile Leu Lys Asn Gln Thr Val Arg Gly Gly Thr Val Glu
     50                  55                  60
```

```
Met Leu Phe Gln Asn Leu Ser Leu Ile Lys Lys Tyr Ile Asp Arg Gln
 65                  70                  75                  80

Lys Glu Lys Phe Asn Asn Phe Thr Val Ser Phe Trp Leu Arg Val Pro
                 85                  90                  95

Lys Val Ser Ala Ser His Leu Glu Arg Thr Arg Gln Phe Leu Asp Tyr
             100                 105                 110

Leu Gln Glu Phe Leu Gly Val Met Ser Thr Glu Trp Ala Met Glu Gly
         115                 120                 125

<210> SEQ ID NO 59
<211> LENGTH: 438
<212> TYPE: DNA
<213> ORGANISM: Artificial Sequence
<220> FEATURE:
<223> OTHER INFORMATION: Description of Artificial Sequence: Murine Il-5
      modified by substitution with tetanus toxoid
      epitopes
<221> NAME/KEY: CDS
<222> LOCATION: (1)..(438)
<221> NAME/KEY: mutation
<222> LOCATION: (256)..(300)
<223> OTHER INFORMATION: Tetanus toxoid P2 epitope
<221> NAME/KEY: mutation
<222> LOCATION: (301)..(363)
<223> OTHER INFORMATION: Tetanus toxoid P30 epitope
<221> NAME/KEY: misc_feature
<222> LOCATION: (1)..(255)
<223> OTHER INFORMATION: DNA encoding amino acids 1-85 of murine IL5
<221> NAME/KEY: misc_feature
<222> LOCATION: (364)..(435)
<223> OTHER INFORMATION: DNA encoding amino acids 90-113 of murine IL5

<400> SEQUENCE: 59 atg gag att ccc atg agc aca gtg gtg aaa gag acc ttg aca cag ctg      48
Met Glu Ile Pro Met Ser Thr Val Val Lys Glu Thr Leu Thr Gln Leu
  1               5                  10                  15 tcc gct cac cga gct ctg ttg aca agc aat gag acg atg agg ctt cct      96
Ser Ala His Arg Ala Leu Leu Thr Ser Asn Glu Thr Met Arg Leu Pro
             20                  25                  30 gtc cct act cat aaa aat cac cag cta tgc att gga gag atc ttt cag     144
Val Pro Thr His Lys Asn His Gln Leu Cys Ile Gly Glu Ile Phe Gln
         35                  40                  45 ggg cta gac ata ctg aag aat caa act gtc cgt ggg ggt acc gtg gaa     192
Gly Leu Asp Ile Leu Lys Asn Gln Thr Val Arg Gly Gly Thr Val Glu
     50                  55                  60 atg cta ttc caa aac ctg tca tta ata aag aaa tac atc gat aga caa     240
Met Leu Phe Gln Asn Leu Ser Leu Ile Lys Lys Tyr Ile Asp Arg Gln
 65                  70                  75                  80 aaa gag aag tgt ggc cag tac atc aag gcc aac tcc aag ttc atc ggc     288
Lys Glu Lys Cys Gly Gln Tyr Ile Lys Ala Asn Ser Lys Phe Ile Gly
                 85                  90                  95 atc acc gag ctg ttc aac aac ttc acc gtg agc ttc tgg ctg cgc gtg     336
Ile Thr Glu Leu Phe Asn Asn Phe Thr Val Ser Phe Trp Leu Arg Val
            100                 105                 110 ccc aag gtg agc gcc agc cac ctg gag agg acg agg cag ttc ctg gat     384
Pro Lys Val Ser Ala Ser His Leu Glu Arg Thr Arg Gln Phe Leu Asp
            115                 120                 125 tat ctg cag gag ttc ctt ggt gtg atg agt aca gag tgg gca atg gaa     432
Tyr Leu Gln Glu Phe Leu Gly Val Met Ser Thr Glu Trp Ala Met Glu
        130                 135                 140 ggc taa                                                             438
Gly
145
```

```
<210> SEQ ID NO 60
<211> LENGTH: 145
<212> TYPE: PRT
<213> ORGANISM: Artificial Sequence
<220> FEATURE:
<223> OTHER INFORMATION: Description of Artificial Sequence: Murine Il-5
      modified by substitution with tetanus toxoid
      epitopes

<400> SEQUENCE: 60

Met Glu Ile Pro Met Ser Thr Val Val Lys Glu Thr Leu Thr Gln Leu
  1               5                  10                  15

Ser Ala His Arg Ala Leu Leu Thr Ser Asn Glu Thr Met Arg Leu Pro
                 20                  25                  30

Val Pro Thr His Lys Asn His Gln Leu Cys Ile Gly Glu Ile Phe Gln
             35                  40                  45

Gly Leu Asp Ile Leu Lys Asn Gln Thr Val Arg Gly Gly Thr Val Glu
 50                  55                  60

Met Leu Phe Gln Asn Leu Ser Leu Ile Lys Lys Tyr Ile Asp Arg Gln
 65                  70                  75                  80

Lys Glu Lys Cys Gly Gln Tyr Ile Lys Ala Asn Ser Lys Phe Ile Gly
                 85                  90                  95

Ile Thr Glu Leu Phe Asn Asn Phe Thr Val Ser Phe Trp Leu Arg Val
            100                 105                 110

Pro Lys Val Ser Ala Ser His Leu Glu Arg Thr Arg Gln Phe Leu Asp
        115                 120                 125

Tyr Leu Gln Glu Phe Leu Gly Val Met Ser Thr Glu Trp Ala Met Glu
    130                 135                 140

Gly
145

<210> SEQ ID NO 61
<211> LENGTH: 57
<212> TYPE: DNA
<213> ORGANISM: Homo sapiens
<220> FEATURE:
<221> NAME/KEY: CDS
<222> LOCATION: (1)..(57)
<223> OTHER INFORMATION: DNA encoding natural human IL5 leader sequence

<400> SEQUENCE: 61 atg agg atg ctt ctg cat ttg agt ttg ctg gct ctt gga gct gcc tac      48
Met Arg Met Leu Leu His Leu Ser Leu Leu Ala Leu Gly Ala Ala Tyr
  1               5                  10                  15 gtg tat gcc                                                          57
Val Tyr Ala <210> SEQ ID NO 62
<211> LENGTH: 19
<212> TYPE: PRT
<213> ORGANISM: Homo sapiens

<400> SEQUENCE: 62

Met Arg Met Leu Leu His Leu Ser Leu Leu Ala Leu Gly Ala Ala Tyr
  1               5                  10                  15

Val Tyr Ala

<210> SEQ ID NO 63
<211> LENGTH: 60
<212> TYPE: DNA
<213> ORGANISM: Mus musculus
```

-continued

```
<220> FEATURE:
<221> NAME/KEY: CDS
<222> LOCATION: (1)..(60)
<223> OTHER INFORMATION: DNA encoding natural murine IL5 leader sequence

<400> SEQUENCE: 63 atg aga agg atg ctt ctg cac ttg agt gtt ctg act ctc agc tgt gtc        48
Met Arg Arg Met Leu Leu His Leu Ser Val Leu Thr Leu Ser Cys Val
 1               5                  10                  15 tgg gcc act gcc                                                        60
Trp Ala Thr Ala
            20

<210> SEQ ID NO 64
<211> LENGTH: 20
<212> TYPE: PRT
<213> ORGANISM: Mus musculus

<400> SEQUENCE: 64

Met Arg Arg Met Leu Leu His Leu Ser Val Leu Thr Leu Ser Cys Val
 1               5                  10                  15

Trp Ala Thr Ala
            20

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence:
      Promiscuous T helper epitope

<400> SEQUENCE: 65

Ala Lys Phe Val Ala Ala Trp Thr Leu Lys Ala Ala Ala
 1               5                  10
```